US008865904B2

(12) United States Patent
Bradford et al.

(10) Patent No.: US 8,865,904 B2
(45) Date of Patent: Oct. 21, 2014

(54) FLUORESCENT CHEMICAL COMPOUNDS HAVING HIGH SELECTIVITY FOR DOUBLE STRANDED DNA, AND METHODS FOR THEIR USE

(71) Applicant: Life Technologies Corporation, Carlsbad, CA (US)

(72) Inventors: Jolene Bradford, Eugene, OR (US); Ching-Ying Cheung, San Ramon, CA (US); Shih-Jung Huang, Eugene, OR (US); Patrick Pinson, Eugene, OR (US); Stephen Yue, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/861,123

(22) Filed: Apr. 11, 2013

(65) Prior Publication Data
US 2013/0224735 A1 Aug. 29, 2013

Related U.S. Application Data

(63) Continuation of application No. 13/559,300, filed on Jul. 26, 2012, now abandoned, which is a continuation of application No. 13/104,413, filed on May 10, 2011, now abandoned, which is a continuation of application No. 12/573,809, filed on Oct. 5, 2009, now Pat. No. 7,943,777, which is a continuation of application No. 11/432,814, filed on May 11, 2006, now Pat. No. 7,598,390.

(60) Provisional application No. 60/680,243, filed on May 11, 2005.

(51) Int. Cl.
C07D 215/00 (2006.01)
C07D 417/04 (2006.01)
C07D 215/10 (2006.01)
C07D 277/72 (2006.01)
C07D 277/74 (2006.01)
G01N 21/64 (2006.01)
C07D 417/14 (2006.01)
C07D 417/06 (2006.01)
C07D 215/227 (2006.01)

(52) U.S. Cl.
CPC .......... *G01N 21/6486* (2013.01); *C07D 417/04* (2013.01); *C07D 215/10* (2013.01); *C07D 277/72* (2013.01); *C07D 277/74* (2013.01); *C07D 417/14* (2013.01); *C07D 417/06* (2013.01); *C07D 215/227* (2013.01)
USPC .......................................................... 546/165

(58) Field of Classification Search
CPC .............................. C07D 215/10; C07D 215/02
USPC ........................................ 546/157, 162, 165
See application file for complete search history.

(56) References Cited

U.S. PATENT DOCUMENTS

| | | | |
|---|---|---|---|
| 2,269,234 A | 1/1942 | Sprague | |
| 2,646,430 A * | 7/1953 | Brooker et al. | 546/72 |
| 3,326,688 A | 6/1967 | Brooker et al. | |
| 3,458,318 A | 7/1969 | Brooks | |
| 3,490,910 A * | 1/1970 | Krieger et al. | 430/592 |
| 3,623,882 A | 11/1971 | Gotze et al. | |
| 3,840,377 A | 10/1974 | Sato et al. | |
| 3,890,155 A | 6/1975 | Nakamura et al. | |
| 3,988,513 A | 10/1976 | Matsuyama et al. | |
| 4,003,750 A | 1/1977 | Heseltine et al. | |
| 4,126,516 A | 11/1978 | Messing et al. | |
| 4,190,328 A | 2/1980 | Levine et al. | |
| 4,225,669 A | 9/1980 | Melnick et al. | |
| 4,304,908 A | 12/1981 | Frishberg et al. | |
| 4,336,321 A | 6/1982 | Kanada et al. | |
| 4,337,063 A | 6/1982 | Mihara et al. | |
| 4,343,782 A | 8/1982 | Shapiro | |
| 4,386,146 A | 5/1983 | Kishino et al. | |
| 4,424,201 A | 1/1984 | Valinsky et al. | |
| 4,508,821 A | 4/1985 | Mansour et al. | |
| 4,510,235 A | 4/1985 | Ukai et al. | |
| 4,520,110 A | 5/1985 | Stryer et al. | |
| 4,542,104 A | 9/1985 | Stryer et al. | |
| 4,544,546 A | 10/1985 | Wang et al. | |
| 4,554,546 A | 11/1985 | Herbreteau et al. | |
| 4,556,636 A | 12/1985 | Belly et al. | |
| 4,603,209 A | 7/1986 | Tsien et al. | |
| 4,639,421 A | 1/1987 | Sage | |

(Continued)

FOREIGN PATENT DOCUMENTS

| | | |
|---|---|---|
| CA | 2119126 | 4/1993 |
| CA | 2133765 | 11/1999 |

(Continued)

OTHER PUBLICATIONS

Melissa et al. STN Accession No. 1996:448419 Document No. 125:162477 Abstract of Biospectroscopy (1996), 2(3), 173-183.*
Gdajev et al. in Dyes and Pigments 57 (2003) 161-164.*
U.S. Appl. No. 09/557,275, Notice of Allowance, Jun. 4, 2003.
U.S. Appl. No. 09/557,275, Office Action mailed Nov. 20, 2002, Nov. 20, 2002, 1-9.
U.S. Appl. No. 09/557,275, Response to Nov. 20, 2002 Office Action, filed Mar. 13, 2003, Mar. 13, 2003, 1-54.
U.S. Appl. No. 09/557,275, Response to Rest. Req., filed Aug. 21, 2002, Aug. 21, 2002, 1-103.
U.S. Appl. No. 09/557,275, Restriction Req. mailed Jul. 22, 2000, Jul. 22, 2000, 1-6.

(Continued)

*Primary Examiner* — Nizal Chandrakumar
(74) *Attorney, Agent, or Firm* — Life Technologies Corporation

(57) ABSTRACT

Chemical compounds having a high selectivity for double stranded DNA over RNA and single stranded DNA are disclosed. The chemical compounds are stains that become fluorescent upon illumination and interaction with double stranded DNA, but exhibit reduced or no fluorescence in the absence of double stranded DNA. The compounds can be used in a variety of biological applications to qualitatively or quantitatively assay DNA, even in the presence of RNA.

9 Claims, No Drawings

(56) References Cited

U.S. PATENT DOCUMENTS

| | | | |
|---|---|---|---|
| 4,665,024 | A | 5/1987 | Mansour et al. |
| 4,711,955 | A | 12/1987 | Ward et al. |
| 4,737,454 | A | 4/1988 | Dattagupta et al. |
| 4,740,891 | A | 4/1988 | Kirkpatrick et al. |
| 4,762,701 | A | 8/1988 | Horan et al. |
| 4,774,339 | A | 9/1988 | Haugland et al. |
| 4,783,401 | A | 11/1988 | Horan et al. |
| 4,810,636 | A | 3/1989 | Corey et al. |
| 4,812,409 | A | 3/1989 | Babb et al. |
| 4,837,141 | A | 6/1989 | Kohno et al. |
| 4,849,362 | A | 7/1989 | Demarinis et al. |
| 4,859,582 | A | 8/1989 | Stryer et al. |
| 4,859,584 | A | 8/1989 | Horan et al. |
| 4,883,867 | A | 11/1989 | Lee et al. |
| 4,886,744 | A | 12/1989 | Arnost et al. |
| 4,921,805 | A | 5/1990 | Gebeyehu et al. |
| 4,937,198 | A | 6/1990 | Lee et al. |
| 4,945,171 | A | 7/1990 | Haugland et al. |
| 4,957,870 | A | 9/1990 | Lee et al. |
| 4,997,928 | A | 3/1991 | Hobbs |
| 5,041,366 | A | 8/1991 | Asano et al. |
| 5,047,519 | A | 9/1991 | Hobbs et al. |
| 5,049,673 | A | 9/1991 | Tsien et al. |
| 5,055,556 | A | 10/1991 | Stryer et al. |
| 5,057,413 | A | 10/1991 | Terstappen et al. |
| 5,122,602 | A | 6/1992 | Corey et al. |
| 5,132,432 | A | 7/1992 | Haugland et al. |
| 5,137,810 | A | 8/1992 | Sizemore et al. |
| 5,169,788 | A | 12/1992 | Chen et al. |
| 5,171,534 | A | 12/1992 | Smith et al. |
| 5,182,214 | A | 1/1993 | Kessler et al. |
| 5,187,288 | A | 2/1993 | Kang et al. |
| 5,208,148 | A | 5/1993 | Haugland et al. |
| 5,221,518 | A | 6/1993 | Mills |
| 5,227,487 | A | 7/1993 | Haugland et al. |
| 5,242,805 | A | 9/1993 | Naleway et al. |
| 5,248,782 | A | 9/1993 | Haugland et al. |
| 5,264,589 | A | 11/1993 | Corey |
| 5,268,486 | A | 12/1993 | Waggoner et al. |
| 5,274,113 | A | 12/1993 | Kang et al. |
| 5,279,790 | A | 1/1994 | Corey et al. |
| 5,314,805 | A | 5/1994 | Haugland et al. |
| 5,316,906 | A | 5/1994 | Haugland et al. |
| 5,321,130 | A | 6/1994 | Yue et al. |
| 5,326,692 | A | 7/1994 | Brinkley |
| 5,332,666 | A | 7/1994 | Prober |
| 5,352,803 | A | 10/1994 | Mattingly |
| 5,362,628 | A | 11/1994 | Haugland et al. |
| 5,375,606 | A | 12/1994 | Slezak et al. |
| 5,401,469 | A | 3/1995 | Kobayashi et al. |
| 5,401,847 | A | 3/1995 | Glazer |
| 5,405,975 | A | 4/1995 | Kuhn et al. |
| 5,410,030 | A | 4/1995 | Yue et al. |
| 5,426,772 | A | 6/1995 | Brady et al. |
| 5,433,896 | A | 7/1995 | Kang et al. |
| 5,436,134 | A | 7/1995 | Haugland et al. |
| 5,437,980 | A | 8/1995 | Haugland |
| 5,442,045 | A | 8/1995 | Haugland et al. |
| 5,443,986 | A | 8/1995 | Haugland et al. |
| 5,445,946 | A | 8/1995 | Roth et al. |
| 5,451,343 | A | 9/1995 | Neckers et al. |
| 5,453,517 | A | 9/1995 | Kuhn et al. |
| 5,459,268 | A | 10/1995 | Haugland et al. |
| 5,459,276 | A | 10/1995 | Kuhn et al. |
| 5,486,616 | A | 1/1996 | Waggoner et al. |
| 5,491,057 | A * | 2/1996 | Hioki ................... 430/584 |
| 5,501,980 | A | 3/1996 | Katerinopoulos et al. |
| 5,534,416 | A | 7/1996 | Millard et al. |
| 5,545,535 | A | 8/1996 | Roth et al. |
| 5,564,554 | A | 10/1996 | Lawrence |
| 5,565,554 | A | 10/1996 | Glazer et al. |
| 5,569,587 | A | 10/1996 | Waggoner |
| 5,569,766 | A | 10/1996 | Waggoner et al. |
| 5,573,904 | A | 11/1996 | Mattingly |
| 5,573,909 | A | 11/1996 | Singer et al. |
| 5,578,439 | A | 11/1996 | Inagaki |
| 5,582,977 | A | 12/1996 | Yue et al. |
| 5,597,696 | A | 1/1997 | Linn et al. |
| 5,616,502 | A | 4/1997 | Haugland et al. |
| 5,627,027 | A | 5/1997 | Waggoner |
| 5,648,270 | A | 7/1997 | Kuhn et al. |
| 5,656,449 | A | 8/1997 | Yue |
| 5,656,554 | A | 8/1997 | Desai et al. |
| 5,658,735 | A | 8/1997 | Lee |
| 5,658,751 | A * | 8/1997 | Yue et al. ................. 435/34 |
| 5,691,145 | A | 11/1997 | Pitner et al. |
| 5,696,157 | A | 12/1997 | Wang et al. |
| 5,714,327 | A | 2/1998 | Houthoff et al. |
| 5,734,058 | A | 3/1998 | Lee |
| 5,760,201 | A | 6/1998 | Glazer |
| 5,798,276 | A | 8/1998 | Haugland et al. |
| 5,800,996 | A | 9/1998 | Lee et al. |
| 5,830,912 | A | 11/1998 | Gee et al. |
| 5,846,737 | A | 12/1998 | Kang |
| 5,847,162 | A | 12/1998 | Lee et al. |
| 5,853,969 | A | 12/1998 | Harada et al. |
| 5,863,727 | A | 1/1999 | Lee et al. |
| 5,863,753 | A | 1/1999 | Haugland et al. |
| 5,869,689 | A | 2/1999 | Zhang et al. |
| 5,925,517 | A | 7/1999 | Tyagi et al. |
| 5,929,227 | A | 7/1999 | Glazer et al. |
| 5,945,526 | A | 8/1999 | Lee et al. |
| 5,963,753 | A | 10/1999 | Ohtani et al. |
| 6,004,536 | A | 12/1999 | Leung et al. |
| 6,008,373 | A | 12/1999 | Waggoner et al. |
| 6,008,379 | A | 12/1999 | Benson et al. |
| 6,017,712 | A | 1/2000 | Lee et al. |
| 6,025,505 | A | 2/2000 | Lee et al. |
| 6,027,709 | A | 2/2000 | Little et al. |
| 6,048,982 | A | 4/2000 | Waggoner et al. |
| 6,080,852 | A | 6/2000 | Lee et al. |
| 6,083,699 | A | 7/2000 | Leushner et al. |
| 6,103,476 | A | 8/2000 | Tyagi et al. |
| 6,114,350 | A | 9/2000 | Randall et al. |
| 6,130,101 | A | 10/2000 | Mao et al. |
| 6,140,494 | A | 10/2000 | Hamilton et al. |
| 6,146,831 | A | 11/2000 | Davis et al. |
| 6,153,370 | A | 11/2000 | Maruyama et al. |
| 6,162,931 | A | 12/2000 | Gee et al. |
| 6,184,379 | B1 | 2/2001 | Josel et al. |
| 6,197,956 | B1 | 3/2001 | Randall et al. |
| 6,200,752 | B1 | 3/2001 | Lakowicz |
| 6,204,389 | B1 | 3/2001 | Randall et al. |
| 6,221,606 | B1 | 4/2001 | Benson et al. |
| 6,224,644 | B1 | 5/2001 | Randall et al. |
| 6,225,050 | B1 | 5/2001 | Waggoner |
| 6,229,055 | B1 | 5/2001 | Klaubert et al. |
| 6,239,626 | B1 | 5/2001 | Chesavage et al. |
| 6,271,035 | B1 | 8/2001 | Deka et al. |
| 6,291,203 | B1 | 9/2001 | Poot et al. |
| 6,316,276 | B1 | 11/2001 | Gregory et al. |
| 6,323,337 | B1 | 11/2001 | Singer et al. |
| 6,329,205 | B1 | 12/2001 | Diwu et al. |
| 6,339,392 | B1 | 1/2002 | Ashihara et al. |
| 6,342,389 | B1 | 1/2002 | Cubicciotti |
| 6,348,596 | B1 | 2/2002 | Lee et al. |
| 6,348,599 | B1 | 2/2002 | Cummins et al. |
| 6,358,684 | B1 | 3/2002 | Lee |
| 6,365,341 | B1 | 4/2002 | Wu et al. |
| 6,368,801 | B1 | 4/2002 | Faruqi |
| 6,372,445 | B1 | 4/2002 | Davis et al. |
| 6,399,392 | B1 | 6/2002 | Haugland et al. |
| 6,403,807 | B1 | 6/2002 | Singh et al. |
| 6,428,667 | B1 | 8/2002 | Glazer et al. |
| 6,495,692 | B1 * | 12/2002 | Wang et al. ................. 546/145 |
| 6,541,205 | B1 | 4/2003 | Yokoyama et al. |
| 6,562,632 | B1 | 5/2003 | Szalecki et al. |
| 6,579,718 | B1 | 6/2003 | Yue et al. |
| 6,664,047 | B1 | 12/2003 | Haugland et al. |
| 6,716,979 | B2 | 4/2004 | Diwu et al. |
| 6,967,251 | B2 | 11/2005 | Haugland et al. |
| 6,972,326 | B2 | 12/2005 | Haugland et al. |
| 6,974,873 | B2 | 12/2005 | Leung et al. |
| 6,977,305 | B2 | 12/2005 | Leung et al. |

(56) References Cited

U.S. PATENT DOCUMENTS

| | | |
|---|---|---|
| 7,226,740 B2 | 6/2007 | Haugland et al. |
| 7,271,265 B2 | 9/2007 | Haugland et al. |
| 7,446,202 B2 | 11/2008 | Dallwig et al. |
| 7,598,390 B2 | 10/2009 | Bradford et al. |
| 7,943,777 B2 | 5/2011 | Bradford et al. |
| 2005/0208534 A1 | 9/2005 | Dallwig et al. |
| 2005/0214810 A1 | 9/2005 | Dallwig et al. |
| 2005/0244976 A1 | 11/2005 | Gee et al. |
| 2006/0004188 A1 | 1/2006 | Leung et al. |
| 2006/0099638 A1 | 5/2006 | Leung et al. |
| 2006/0263844 A1 | 11/2006 | Bradford et al. |
| 2007/0178511 A1 | 8/2007 | Leung et al. |
| 2007/0178512 A1 | 8/2007 | Leung et al. |
| 2007/0232805 A1 | 10/2007 | Leung et al. |
| 2008/0039630 A1 | 2/2008 | Haugland et al. |
| 2008/0044811 A1 | 2/2008 | Haugland et al. |
| 2008/0199875 A1 | 8/2008 | Yue et al. |
| 2009/0047683 A1 | 2/2009 | Dallwig et al. |
| 2010/0143917 A1 | 6/2010 | Bradford et al. |

FOREIGN PATENT DOCUMENTS

| | | |
|---|---|---|
| DE | 917330 | 7/1954 |
| DE | 1923992 | 11/1970 |
| DE | 2135413 | 1/1972 |
| DE | 3141554 A1 * | 5/1982 |
| EP | 226272 | 6/1987 |
| EP | 0410806 A1 | 1/1991 |
| EP | 0453197 A1 | 10/1991 |
| EP | 0492570 A1 | 7/1992 |
| EP | 0517050 A2 | 12/1992 |
| EP | 0517055 A1 | 12/1992 |
| EP | 605655 | 4/1993 |
| EP | 675924 | 10/1994 |
| EP | 0710668 A2 | 5/1996 |
| EP | 740689 | 5/1996 |
| EP | 0714986 A1 | 6/1996 |
| EP | 0745690 | 12/1996 |
| EP | 0805376 | 11/1997 |
| EP | 0472812 | 3/1998 |
| EP | 870753 | 10/1998 |
| EP | 882983 | 12/1998 |
| EP | 0985964 | 3/2000 |
| FR | 1510234 | 1/1968 |
| GB | 649725 | 1/1951 |
| GB | 870753 | 7/1958 |
| GB | 1324624 | 7/1973 |
| GB | 1529202 | 10/1978 |
| GB | 2074340 | 10/1981 |
| JP | 57-72150 | 5/1982 |
| JP | 63-132688 | 6/1988 |
| JP | 02084383 | 3/1990 |
| JP | 05-287209 | 11/1993 |
| JP | 06-123740 | 5/1994 |
| JP | 07-196930 | 8/1995 |
| JP | 09-507879 | 8/1997 |
| JP | 10-319010 | 12/1998 |
| JP | 11-323173 | 11/1999 |
| JP | 2000-241932 | 9/2000 |
| JP | 2000-319260 | 11/2000 |
| JP | 09-281495 | 11/2001 |
| JP | 2002-501102 | 1/2002 |
| JP | 2004-536900 | 12/2004 |
| JP | 2006-292808 | 10/2006 |
| WO | WO-92/07867 A1 | 5/1992 |
| WO | WO-93/00633 | 1/1993 |
| WO | WO-93/04074 | 3/1993 |
| WO | WO-93/04192 | 3/1993 |
| WO | WO-93/06482 | 4/1993 |
| WO | WO-93/11120 A1 | 6/1993 |
| WO | WO-94/05688 | 3/1994 |
| WO | WO-94/24213 | 10/1994 |
| WO | WO-96/13552 | 5/1996 |
| WO | WO-96/36882 | 11/1996 |
| WO | WO-97/12508 | 4/1997 |
| WO | WO-97/17076 | 5/1997 |
| WO | WO-97/39064 | 10/1997 |
| WO | WO-97/45539 | 12/1997 |
| WO | WO-98/17826 | 4/1998 |
| WO | WO-99/37717 | 7/1999 |
| WO | WO-99/64519 | 12/1999 |
| WO | WO-00/66664 | 11/2000 |
| WO | WO-01/86264 | 11/2001 |
| WO | WO-2004/038038 | 5/2004 |
| WO | WO-2005/012579 | 2/2005 |
| WO | WO-2005/056687 A2 | 6/2005 |
| WO | WO-2006/124816 A1 | 11/2006 |

OTHER PUBLICATIONS

U.S. Appl. No. 09/557,275, Supp. Resp. To Rest. Req., filed Oct. 16, 2002, Oct. 16, 2002, 1-103.

U.S. Appl. No. 10/683,753, Notice of Allowance mailed Jan. 29, 2007, Jan. 29, 2007.

U.S. Appl. No. 10/683,753, Office Action mailed Jun. 9, 2006, Jun. 9, 2006.

U.S. Appl. No. 10/683,753, Office Action mailed Oct. 2, 2006, Oct. 2, 2006.

U.S. Appl. No. 10/683,753, Response to Jun. 9, 2006 Office Action, filed Sep. 11, 2006, Sep. 11, 2006.

U.S. Appl. No. 10/683,753, Response to Oct. 2, 2006 Office Action, filed Jan. 3, 2007, Jan. 3, 2007.

U.S. Appl. No. 10/683,753, Response to Rest. Req., filed Apr. 27, 2006, Apr. 27, 2006.

U.S. Appl. No. 10/683,753, Restriction Req. mailed Mar. 29, 2006, Mar. 29, 2006.

U.S. Appl. No. 10/911,423, Office Action mailed Sep. 17, 2007, Sep. 17, 2007.

U.S. Appl. No. 10/911,423, Office Action mailed Dec. 21, 2007, Dec. 21, 2007.

U.S. Appl. No. 10/911,423, Response to Sep. 17, 2007 Office Action, filed Oct. 17, 2007, Oct. 17, 2007.

U.S. Appl. No. 10/911,423, Response to Rest. Req. filed Jul. 9, 2007, Jul. 9, 2007.

U.S. Appl. No. 10/911,423, Restriction Req. mailed Jun. 8, 2007, Jun. 8, 2007.

U.S. Appl. No. 10/916,822, Advisory Action mailed Aug. 29, 2006, Aug. 29, 2006.

U.S. Appl. No. 10/916,822, Notice of Allowance, May 11, 2007.

U.S. Appl. No. 10/916,822, Office Action mailed Jun. 13, 2006, Jun. 13, 2006.

U.S. Appl. No. 10/916,822, Office Action mailed Nov. 30, 2006, Nov. 30, 2006.

U.S. Appl. No. 10/916,822, Office Action mailed Dec. 9, 2005, Dec. 9, 2005.

U.S. Appl. No. 10/916,822, Response to Jun. 13, 2006 Office Action, filed Aug. 14, 2006, Aug. 14, 2006.

U.S. Appl. No. 10/916,822, Response to Aug. 29, 2006 Advisory Action, filed Sep. 13, 2006, Sep. 13, 2006.

U.S. Appl. No. 10/916,822, Response to Nov. 30, 2006 Office Action, filed Feb. 27, 2007, Feb. 27, 2007.

U.S. Appl. No. 10/916,822, Supp. Response to Nov. 30, 2006 Office Action, filed May 7, 2007, May 7, 2007.

U.S. Appl. No. 11/005,860, Notice of Allowance mailed Jun. 30, 2008, Jun. 30, 2008.

U.S. Appl. No. 11/005,860, Office Action mailed Dec. 28, 2007, Dec. 28, 2007.

U.S. Appl. No. 11/005,860, Response to Dec. 28, 2007 Office Action, filed Mar. 28, 2008, Mar. 28, 2008.

U.S. Appl. No. 11/005,860, Response to Rest. Req., filed Oct. 12, 2007, Oct. 12, 2007.

U.S. Appl. No. 11/005,860, Restriction Req. mailed Sep. 12, 2007, Sep. 12, 2007.

U.S. Appl. No. 11/005,861, Final Office Action mailed Nov. 24, 2006, Nov. 24, 2006.

U.S. Appl. No. 11/005,861, Final Office Action mailed Jul. 10, 2008, Jul. 10, 2008.

U.S. Appl. No. 11/005,861, Non-Final Office Action mailed Apr. 13, 2009, Apr. 13, 2009.

(56) References Cited

OTHER PUBLICATIONS

U.S. Appl. No. 11/005,861, Non-final Office Action mailed Apr. 13, 2007, Apr. 13, 2007.
U.S. Appl. No. 11/005,861, Non-final Office Action mailed Jul. 28, 2006, Jul. 28, 2006.
U.S. Appl. No. 11/005,861, Non-final Office Action mailed Sep. 27, 2007, Sep. 27, 2007.
U.S. Appl. No. 11/005,861, Response to Nov. 24, 2006 Final Office Action, filed Feb. 26, 2007, Feb. 26, 2007.
U.S. Appl. No. 11/005,861, Response to Apr. 13, 2007 Non-final Office Action, filed Jul. 13, 2007, Jul. 13, 2007.
U.S. Appl. No. 11/005,861, Response to Jul. 28, 2006 Non-final Office Action, filed Oct. 30, 2006, Oct. 30, 2006.
U.S. Appl. No. 11/005,861, Response to Sep. 27, 2007 Non-final Office Action, filed Mar. 27, 2008, Mar. 27, 2008.
U.S. Appl. No. 11/005,861, Response to Restriction Requirement, filed Jun. 22, 2006, Jun. 22, 2006.
U.S. Appl. No. 11/005,861, Restriction Requirement mailed May 31, 2006, May 31, 2006.
U.S. Appl. No. 11/063,707, Advisory Action mailed Jan. 19, 2007, Jan. 19, 2007.
U.S. Appl. No. 11/063,707, Office Action mailed Apr. 30, 2007, Apr. 30, 2007.
U.S. Appl. No. 11/063,707, Office Action mailed Jun. 1, 2006, Jun. 1, 2006.
U.S. Appl. No. 11/063,707, Office Action mailed Oct. 12, 2006, Oct. 12, 2006.
U.S. Appl. No. 11/063,707, Response Oct. 12, 2006 Office Action, filed Dec. 8, 2006, Dec. 8, 2006.
U.S. Appl. No. 11/063,707, Response to Jan. 19, 2007 Advisory Action, filed Feb. 12, 2007, Feb. 12, 2007.
U.S. Appl. No. 11/063,707, Response to Jun. 1, 2006 Office Action, filed Oct. 2, 2006, Oct. 2, 2006.
U.S. Appl. No. 11/063,707, Response to Rest. Req., filed Mar. 27, 2006, Mar. 27, 2006.
U.S. Appl. No. 11/063,707, Restriction Req. mailed Mar. 13, 2006, Mar. 13, 2006.
U.S. Appl. No. 11/432,814, Notice of Allowance, Oct. 27, 2008.
U.S. Appl. No. 11/432,814, Notice of Allowance mailed Feb. 27, 2009, 29 pgs.
U.S. Appl. No. 11/432,814, Office Action Mailed Jul. 13, 2009, 9 Pgs.
U.S. Appl. No. 11/432,814, Office Action mailed Mar. 27, 2008, Mar. 27, 2008.
U.S. Appl. No. 11/432,814, Office Action Mailed Jul. 22, 2009, 4 pgs.
U.S. Appl. No. 11/432,814, Office Action Mailed Jul. 16, 2009, 4 pgs.
U.S. Appl. No. 11/432,814, Response to Mar. 27, 2008 Office Action, filed Aug. 26, 2008, Aug. 26, 2008.
U.S. Appl. No. 11/432,814, Supplemental Notice of allowability mailed Apr. 14, 2009.
U.S. Appl. No. 11/756,765, Final Office Action Mailed on Jan. 8, 2009, Jan. 8, 2009, 5 pgs.
U.S. Appl. No. 11/756,765, Office Action mailed Apr. 2, 2008, Apr. 2, 2008.
U.S. Appl. No. 11/756,765, Response to Apr. 2, 2008 Office Action, filed Oct. 2, 2008, Oct. 2, 2008.
U.S. Appl. No. 12/240,218, Office Action Mailed May 29, 2009, May 29, 2009.
U.S. Appl. No. 12/573,809, Notice of Allowance Mailed Jan. 6, 2011, 31.
Abramo, K. H. et al., "Spectroscopic Studies of Single-Standard DNA Ligands and Oxazole Yellow Dyes", *Biospectroscopy*, 4(1), 1998, 27-35.
Allan, R A. et al., "Influence of S-adenosylmethionine on DAPI-induced fluorescence of polyphosphate in the yeast vacuole ", *Canadian Journal of Microbiology*, vol. 26, National Research Council of Canada Apr. 22, 1980, 912-920.
Allmann, et al., "Konformationsanalyse von Polymethinen I, Erstmaliger Nachweis von di-, tri-und all-cis-Konformationen bei sterisch gehinderten Trimethincyaninen (Carbocyaninen) der Indolin- und Benzothiazolreihe", *Angewandte Chemie International Edition in German*, vol. 22, Issue Supplement 11,, Nov. 1983, 1147-1175.
Ausubel, Frederick M. et al., "Short Protocols in Molecular Biology", 2002, 359.
Barlin, Gordon B. et al., "Purine Analogues as Amplifiers of Phleomycin. IX* Some 2- and 6-Substituted Thiazolo [4,5,-b] Pyrazines, 2-Substituted Thiazolo[4,5,-c]- and Thiazolo[5,4,-b]-Pyridines and Related Compunds", *Aust. J. Chem.*, vol. 37, 1984, 1729-1737.
Barlin, Gordon B. et al., "Purine Analogues as Amplifiers of Phleomyein. Some Thiazolo[4,5-g] pyrazines and Related Compounds", *Aust. J. Chem.*, vol. 36, 1983, 983-985.
Barni, Ermanno et al., "Synthesis, Surface Activity and Micelle Formation of Novel Cyanine Dyes", *Helvetica Chimica Acta*, vol. 64, No. 6, 1981, 1943-1948.
Bartnik, Romuald et al., "Synthesis of New Trimethinecy Anine Dyes by Condensation of 2-Formylmethylene-3,3-Dimethylindoline with 2-Cyanomethylbenzimidazoles", *Polish Journal of Applied Chemistry*, vol. 37, No. 1-2, 1993, 119-125.
Beebe, et al., "A continuous fluorimetric assay for tail specific protease", *Analytical Biochemistry*, vol. 263, Issue 1,, Oct. 1, 1998, 51-56.
Beekman, et al., "Highly increased levels of active stromelysin in rheumatoid synovial fluid determined by a selective fluorogenic assay", *FEBS Letters*, vol. 418, Issue 3, Dec. 1, 1997, 305-309.
Beekman, B. et al., "Convenient fluorometric assay for matrix metalloproteinase activity and its application in biological media", *FEBS Letters*, 390(2), 1996, 221-225.
Bengtsson, Martin et al., "A New Minor Groove Binding Asymmetric Cyanine Reporter dye for Real-Time PCR", *Nucleic Acids Research*, vol. 31(8), 2003, e45, 1-5.
Bensimon, A. et al., "Alignment and Sensitive Detection of DNA by Moving Interface", *Science*, vol. 265, 1994, 2096-2098.
Berge, Stephen M. et al., "Pharmaceutical Salts", *Journal of Pharmaceutical Science*, vol. 66, 1977, 1-19.
Bolton, Philip H. et al., "Spectroscopic properties of ethidium monoazide: a fluorescent photoaffinity label for nucleic acids", *Nucleic Acids Research*, vol. 5, 1978, 4891-4904.
Bouizar, Zhor et al., "Purification and Characterization of Calcitonin Receptors in Rat Kidney Membranes by Covalent Cross-Linking Techniques.", *Eur. J. Biochem*, vol. 155, No. 1, 1986, pp. 141-147.
Bradford, M. M. , "A Rapid and Sensitive Method for the Quantitation of Microgram Quantities of Protein Utilizing the Principle of Protein-Dye Binding", *Analytical Biochemistry*, vol. 72, No. 2, 1976, 248-254.
Brinkley, Michael , "A Brief Survey of Methods for Preparing Protein Conjugates with Dyes, Haptens, and Cross-Linking Reagents", *Bioconjugate Chemistry*, vol. 3, Issue 1, 1992, pp. 2-13.
Brooker, L G. et al., "Color and consitution. V. The absorption of unsymmetrical cyanines. Resonance as a basis for a classification of dyes", *Journal of the American Chemical Society*, vol. 64, Communication No. 833 From the Kodak Research Laboratories, Feb. 1942, 199-210.
Brooker, L. G. S. et al., "Color and Constitution. XI.1 Anhydronium Bases of p-Hydroxystyryl Dyes as Solvent Polarity Indicators", *Journal of the American Chemical Society*, vol. 73, No. 11, 1951, 5350-5356.
Brooker, L.G. S. et al., "Studies in the Cyanine Dye Series. XL. The Merocyanines", *Journal of the American Chemical Society*, vol. 73, No. 11, 1951, 5326-5332.
Brooker, L.G.S. et al., "Color and constitution. X. Absorption of the Merocyanines", *Journal of the American Chemical Society*, vol. 73, Communication No. 1397 from the Kodak Research Laboratories., 1951, 5332-5350.
Browning, et al., "Studies on the Differing Effects of the Tumor Necrosis Factor and Lymphotoxin on the Growth of Several Human Tumor Lines", *Journal of Immunology*, vol. 143, Issue 6, 1989, pp. 1859-1867.
Buehler, R. et al., "Charge Translocation by the Sodium, Potassium pump: I. Kinetics of Local Field Changes Studied by Time-Resolved Fluorescence Measurements", *Chemical Abstracts* 115 (9), 1991, 3 pages.

(56) References Cited

OTHER PUBLICATIONS

Buhler, R. et al., "Charge Translocation by the Na, K-Pump: I Kinetics of Local Field Changes Studied by Time-Resolved Fluorescence Measurements", *Journal of Membrane Biology*, vol. 121, No. 2, Apr. 1991, 141-161.
Bunkenborg, Jakob et al., "Concerted intercalation and minor groove recognition of DNA by a homodimeric thiazole orange dye", *Bioconjugate Chemistry*, vol. 11, No. 6, 2000, 861-867.
Carlsson, et al., "Optical and Photophysical Properties of the Oxazole Yellow DNA Probes YO and YOYO", *Abstract of Journal of Physical Chemistry*, 98(40), 10313-21, STN Accession No. 1994:650470, 1994, 2 pgs.
Castro, Alonso et al., "Fluorescence Detection and Size Measurement of Single DNA Molecules", *Anal. Chem.*, 65, 1993, 849-852.
Chu-Moyer, Margaret Y. et al., "Preparation of the Four Regioisomeric 2-(Methylthio)oxazolopyridines: Useful Synthons for Elaboration to 2-(Amino substituted)oxazolopyridines", *Journal of Organic Chemistry*, vol. 60, No. 17, 1995, 5721-5725.
Ci, Yun-Xiang et al., "Fluorimetric Determination of Human Serum Albumin with Eriochrome Cyanine R", *Analyst*, vol. 113, Apr. 1988, 679-681.
Clark, Leslie M. et al., "Reactivity of the Imino-group in 1-Imino-2-methylbenzthiazoline", *Journal of the Chemical Society*, Notes, 1936, 507.
Cohen, R L. et al., "A cyanine dye distinguishes between cycling and non-cycling fibroblasts", *Nature*, vol. 290, Apr. 16, 1981, 593-595.
Coppieters, Kris, "A Cross-Platform Binary Diff", *Dr. Dobb's Journal*, vol. 32: http://www.ddj.com/architect/184409550, May 1, 1995, 35-36.
Couture, Axel et al., "2-ARYL-OXazolo- and Thiazolopyrdines. Synthesis via Cyclization of N-(2 Chloro-3-Pyridinyl) Arylamides and Thiomides", *Heterocycles*, vol. 22, No. 6, 1984, 1383-1385.
Couture, Axel et al., "Nouvelle Methode De Synthese De Thiazolopyridines", *(French Version) J. Heterocyclin Chem.*, vol. 24, 1987, 1765-1769.
Czikkely, V. et al., "Lichtabsorption von Farbstoff-Molekulpaaren in Sandwichsystemen aus Monomolekularen Schichten", *Physikalisch-Chemisches Institut*, 1969, 1821-1831.
Daban, Joan-Ramon et al., "Use of the hydrophobic probe Nile red for the fluorescent staining of protein bands in sodium dodecyl sulfate-polyacrylamide gels", *Analytical Biochemistry*, vol. 199, No. 2, 1991, 169-174.
Davis, Bruce H. et al., "Clinical Flow Cytometric Reticulocyte Analysis", *Diagnostic Flow Cytometry*, Chapter 8, 1990, 103-113.
Dean, P. D. G. et al., "Affinity Chromatography: A Practical Approach", *IRL Press Ltd., Oxford,*, 1986, 34-35.
Diwu, Zhenjun et al., "Novel Site-Selective Fluorescent Probes for Lysosome and Acidic Organelle Staining and Long-Term Tracking", *International Society for Analytical Cytology*, Cytometry supp. 7; Abstract# 426B, 1994, 77.
Dos Remedios, Cristobal G. et al., "Fluorescence Resonance Energy Transfer Spectroscopy is a Reliable "Ruler" for Measuring Structural Changes in Proteins", *Journal of Structural Biology*, vol. 115, 1995, pp. 175-185.
EP 94914173, Examination Report, May 16, 2000.
EP 94914173, Examination Report, Jul. 6, 1999.
EP 95937613, Examination Report, Oct. 21, 1999.
EP 96920325, Examination Report mailed Mar. 24, 2003, 1-4.
EP 96920325, Examination Report mailed Mar. 30, 2000, 1-6.
EP 96920325, Examination Report mailed May 30, 2006, 1-6.
EP 96920325, Examination Report mailed Sep. 14, 2001, 1-5.
Eriksson, Maja et al., "Groove-Binding Unsymmetrical Cyanine Dyes for Staining of DNA: Dissociation Rates in Free Solution and Electrophoresis Gels", *Nucleic Acids Research*, vol. 31(21), 2003, pp. 6235-6242.
Eriksson, Maja et al., "Time-Resolved Electrophoretic Analysis of Mobility Shifts for Dissociating DNA Ligands", *Electrophoresis*, vol. 26, 2005, 524-532.
Ficken, et al., "Diazaines and Their Quarternary Salts Part 2", *CA 55:70677*, abstract only of J of Chem Soc, 1961, 584-588.
Ficken, G E. et al., "Diazaindenes and Their Quaternary Salts Part 1: The preparation of 2,3,3-Trimethyl-3H-1,7-diazaindene, and its Methiodides and Derived Cyanine Dyes", *Journal of Chemical Society*, 1959, 3202-3212.
Figeys, et al., "Use of the fluorescent intercalating dyes POPO-3, YOYO-3 and YOYO-1 for ultrasensitive detection of double-stranded DNA separated by capillary electrophoresis with hydroxypropylmethyl cellulose and non-crosslinked polyacrylamide", *Abstract of Journal of Chromatography, A*, STN Accession No. 1994:453324, 1994, 205-16.
Foye, William O. et al., "Antiradiation compounds XV: Condensations of carbon disulfide with amino, chloro, cyanomethyl, and sulfonamido heterocycles", *Journal of Pharmaceutical Science*, vol. 64, No. 8, Aug. 1975, 1371-1374.
Furniss, Brian S. et al., "Resolution of Racemates", *Vogel's Textbook of Practical Organic Chemistry*, Fifth Ed, Longman Group UK Ltd., Essex, 1989, 809-823.
Gadjev, N. I. et al., "Preparation of monomethine cyanine dyes as noncovalent labels for nucleic acids", *Dyes and Pigments*, vol. 40, 1999, 181-186.
Gadjev, N. I. et al., "Synthesis and Properties of YOYO-1-type Homodimeric Monomethine Cyanine Dyes as Noncovalent Nucleic Acid Labels", *Dyes and Pigments*, vol. 57(2), 2003, 161-164.
Gaffney, David K., "The Role of Serum and Serum Components in the Merocyanine 540-Sensitized Photoinactivation of K562 Leukemia Cells", *Chemical Abstracts 117*, Dec. 21, 1992.
Gaffney, David K. et al., "The role of serum and serum components in the merocyanine 540-sensitized photoinactivation of K562 leukemia cells", *Biochimica et Biophysica Acta*, vol. 1117, Issue 3, Feb. 24, 1992, 321-325.
Gaugain, , "DNA Bifunctional Intercalators 2. Fluorescence Properties and DNA Binding Interaction of an Ethidium Homodimer and an Acridine Ethidium Heterodimer", *Biochemistry*, vol. 17 No. 24, 1978, 5078-5088.
Gaugain, et al., "DNA bifunctional intercalators. 1. Synthesis and conformational properties of an ethidium homodimer and of an acridine ethidium heterodimer", *Biochemistry*, vol. 17, No. 24, 1978, 5071-5078.
Gemahlich, M et al., "Elektrophoretische Studien an fluorochromierten Serum- und Organproteinen", *(German Version) Research in Experimental Medicine*, vol. 130, No. 4, Oct. 1958, 312-318.
Gemahlich, M., "Electrophoretic Studies of Fluorochrome-treated Serum and Organ Proteins", *Chemical Abstracts* 54 (20), Oct. 25, 1960, 21215-21216.
Georgi, Ann et al., "Detection of Individual Fluorescently Labeled Reovirions in Living Cells", *Proceedings of the National Academy of Sciences (PNAS)*, vol. 87, 1990, 6579-6583.
Goodwin, P. et al., "Rapid sizing of individual fluorescently stained DNA fragments by flow cytometry", *Nucleic Acids Research*, 21(4), 1993, pp. 803-806.
Govorunov, I. G., "Study of Permeability of *Escherichia coli* Membrane to Ethidium Bromide", *Plenum Publishing Corp.*, 1983, 587-589.
Griffiths, John, "Colour and Constitution of Organic Molecules", *Academic Press*, 1976, 241-251.
Grinvald, A. et al., "Improved fluorescent probes for the measurement of rapid changes in membrane potential.", *Biophys J.*, 39, 1982, 301-308.
Hahn, Klaus M. et al., "A Calcium-sensitive Fluorescent Analog of Calmodulin Based on a Novel Calmodulin-binding Fluorophore", *The Journal of Biological Chemistry*, vol. 265, No. 33, 1990, 20335-20345.
Hamer, Frances M., "vol. 18: The Cyanine Dyes and Related Compounds", *The Chemistry of Heterocyclic Compounds*, A. Weissberger, Ed., Interscience, New York, 1964, 1-34.
Hamer, Frances M., "Bases of which Methincyanines are Quaternary Salts", *The Journal of the Chemical Society*, 1940, 799-808.
Hassner, A. et al., "Charge-Shift Probes of Membrane Potential", *J. Org. Chem.*, 49(14), 1984, 2546-2551.
Haugland, Richard P., "Handbook of Fluorescent Probes and Research Products", *Ch 1-3.3*, Molecular Probes, Inc/Invitrogen, 2002, 2002, 11-118.

(56) References Cited

OTHER PUBLICATIONS

Haugland, Richard P., "Molecular Probes Handbook of Fluorescent Probes and Research Chemicals", *Sixth Edition*, 1996.

Haugland, Richard P., "Molecular Probes Handbook of Fluorescent Probes and Research Chemicals", Fourth Edition, *Molecular Probes, Inc.*, 1989, 1-234.

Haugland, Richard P., "Molecular Probes Handbook of Fluorescent Probes and Research Chemicals", Sixth Edition (Subsequent Seventh and Eighth Edition updates issued on CD Rom, *Molecular Probes, Inc.*, 1996, Handbook Cover-xii.

Haugland, Richard P., "Molecular Probes Handbook of Fluorescent Probes and Research Chemicals", *Chapters 1-3*, Molecular Probes, Inc, 1996, Sixth Edition, 1996, 7/80.

Haugland, Richard P., "Molecular Probes Handbook of Fluorescent Probes and Research Chemicals", *Set 28: Nuclear Stains*, Molecular Probes, Inc., 1989, 129-130.

Haugland, Richard P., "Molecular Probes Handbook of Fluorescent Probes and Research Chemicals", *Sets 25 & 31*, Molecular Probes, Inc., 1992, 172-180, 221-230.

Haugland, Richard P., "Molecular Probes Handbook of Fluorescent Probes and Research Products", 9th Edition, 2002 (CD-Rom Format), *Molecular Probes*, 2002.

Haugland, Richard P., "Molecular Probes Handbook of Fluorescent Probes and Research Chemicals", *Molecular Probes, Inc.*, Sets 1-7, 1992, pp. 9-41.

Haugland, Rosaria P. et al., "Coupling of Antibodies with Biotin", *The Protein Protocols Handbook*, vol. 418, Humana Press, 1996, 13-23.

Haugland, Rosaria P. et al., "Coupling of Antibodies with Biotin", *The Protein Protocols Handbook*, Humana Press, 1996, 293.

Haugland, Rosaria P. et al., "Coupling of monoclonal antibodies with biotin", *Methods in Molecular Biology*, vol. 45, 1995, 223-233.

Haugland, Rosaria P., "Coupling of monoclonal antibodies with fluorophores", *Methods in Molecular Biology*, Monoclonal Antibody Protocols, vol. 45, 1995, pp. 205-243.

Heller, A., "Electrical Wiring of Redox Enzymes", *Acc. Chem. Res.*, vol. 23, No. 5, 1990, 128-134.

Heravi, M M. et al., "Heterocyclic monoazo dyes derived from 2-(p-aminophenyl)oxazolo-[4,5-b]pyridine and 7-(p-aminophenyl)-4H-[1,3,4]thiadiazolo-[2,3-c][1,2,4]triazin-4-one", *Indian J. Chem.*, 36B, 1997, 1025-1029.

Hickman, David T. et al., "Kinetically selective binding of single stranded RNA over DNA by a pyrrolidine-amide oligonucleotide minic (POM)", *Nucleosides Nucleotides & Nucleic Acids*, vol. 20, No. 4-7, 2001, 1169-1172.

Holskin, B. P. et al., "A continuous fluorescence-based assay of human cytomegalovirus protease using a peptide substrate", *Analytical Biochemistry*, vol. 226, 1995, 148-55.

Hongyo, et al., "Cold SCCP': a simple, rapid, and non-radioactive method for optimized single-strand conformation polymorphism analyses", *Nucleic Acids Research*, vol. 21, Issue 16,, Aug. 11, 1993, 3637-3642.

Honig, Marcia G. et al., "Fluorescent carbocyanine dyes allow living neurons of identified origin to be studied in long-term cultures", *The Journal of Cell Biology*, vol. 103, No. 1, Jul. 1, 1986, 171-187.

Houben, Josef et al., "Methoden der organischen Chemie (Houben-Weyl)", (German Version) Band V/1d, Publisher/Distributor: G. Thieme Publisher/Distributor City: Stuttgart Publisher/Distributor Country: Germany, 1972, 231-299.

Ishiguro, Takahiro et al., "Fluorescence detection of specific sequence of nucleic acids by oxazole yellow-linked oligonucleotides. Homogeneous quantitative monitoring of in vitro transcription", *Nucleic Acids Research*, vol. 24, No. 24, 1996, 4992-4997.

Izmail'Skii, V. A. et al., "Exomecular interaction and color VIII. Absorption spectra of molecular complexes of 9-(p-Deimethylaminostyryl)-acridine with 10-alkyl-9-methylacridinium salts", *Journal of General Chemistry of the USSR 29*, vol. 29, Jun. 9, 1958, 1813-1819.

Jensen, O. N. et al., "Mass Spectrometric Identification and Microcharacterization of Proteins from Electrophoretic Gels: Strategies and Applications", *Proteins Suppl*, 2, 1998, 74-89.

Johnson, I. D. et al., "Asymmetric Cyanine Dyes for Fluorescent Staining and Quantification of Nucleic Acids", *Biophysical Society/ASBMB Joint Meeting*, Poster # 1806, 1992.

Joshi, Saroj et al., "ATP Synthase Complex from Bovine Heart Mitochondria", *J. Biol. Chem.*, vol. 265(24), 1990, pp. 14518-14525.

JP08-514689, , Office action Mailed on Dec. 7, 2008.

JP08-514689, , Office Action Response, Application Serial No. Hei08-514689, filed Sep. 29, 2008, 11.

Jung, Stephanie M. et al., "Crosslinking of platelet glycoprotein Ib by N-succinimidyl(4-azidophenyldithio)propionate and 3,3'-dithiobis-(sulfosuccinimidyl propionate)", *Biochimica et Biophysica Acta*, vol. 761, Iss. 2, 1983, pp. 152-162.

Kaneshiro, Edna S. et al., "Reliability of Calcein Acetoxy Methyl Ester and Ethidium Homodimer or Propidium Iodide for Viability Assessment Microbes", *Journal of Mocrobiological Methods*, 17, 1993, 1-16.

Karlsson, H. J. et al., "Groove-binding unsymmetrical cyanine dyes for staining of DNA: syntheses and characterization of the DNA-binding", *Nucleic Acids Res.*, vol. 31(21), 2003, 6227-6234.

Karlsson, H. Jonas et al., "Synthesis and DNA Binding Studies of a New Asymmetric Cyanine Dye Binding in the Minor Groove of [poly(dA-dT)]2", *Bioorganic & Medicinal Chemistry*, vol. 11, 2003, 1035-1040.

Karlsson, H. Jonas et al., "Synthesis and DNA-binding Studies of a Series of Unsymmetrical Cyanine Dyes: Structural influence on the degree of minor groove binding to natural DNA", *Bioorganic & Medicinal Chemistry*, vol. 12, Issue 9, 2004, 2369-2384.

Kaufmann, Hitto et al., "Use of Antibodies for Detection of Phosphorylated Proteins Separated by Two-Dimensional Gel Electrophoresis", *Proteomics*, vol. 1, No. 2, 2001, 194-199.

Khanna, Ish K. et al., "Facile, Regioselective Synthesis of N-Alkylated 2,3-Diaminopyridines and Imidazo[4,5-b]pyridines", *J. Org. Chem.*, vol. 60, 1995, 960-965.

Kudinova, M. A. et al., "Pyrylocyanines 12. Unsymmetrical pyrylo-2-cyanines", *Chemical Abstracts*, vol. 93, No. 25, Abstract # 241188, 1980, 91.

Kudinova, M. A. et al., "Pyrylocyanines. 12. Unsymmetrical pyrylo-2-cyanines", *Institute of Organic Chemistry, Academy of Sciences of teh Ukrainian SSR*, vol. 16, No. 7 (Translated from Khimiya Geterotsiklicheskikh Soedinenii, pp. 903-908, Jul. 1980), 1981, 696-701.

Lee, Linda G. et al., "Thiazole Orange: A New Dye for Reticulocyte Analysis", *Cytometry*, 7, 1986, 508-517.

Loew, et al., "Charge-shift probes of membrane potential. Synthesis", *J. Org. Chem.*, 49, 1984, 2546.

Lowry, Oliver H. et al., "Protein Measurement with the Folin Phenol Reagent", *The Journal of Biological Chemistry*, vol. 193, No. 1, 1951, 265-275.

Makin, S. M. et al., "Synthesis and Investigation of Tricarbocynanines Containing Five-and-Six Membered Rings in the Chromophore", *Journal of Organic Chemistry*, vol. 13, No. 11 (Translated from original Zhurnal Organicheskoi Khimii article, pp. 2440-2443), Nov. 1977, 1977, 2269-2271.

Malone, James P. et al., "Practical aspects of fluorescent staining for proteomic applications.", *Electrophoresis*, vol. 22 No. 5, 2001, 919-32.

Markovits, et al., "Dynamic Structure of DNA Complexes. Fluorometric Measurement of Hydrogen-Deuterium Exchange Kinetics of DNA-bound Ethidium Dimer and Acridine-Ethidium Dimer", *Biochemistry*, vol. 22, No. 13, 1983, 3231-3237.

Markovits, et al., "Effect of B-Z transition and nucleic add structure on the conformational dynamics of bound ethidium dimer measured by hydrogen deuterium exchange kinetics", *Nucleic Acids Research*, vol. 13, No. 10, 1985, 3773-3788.

Markovits, et al., "Ethidium Dimer: A New Reagent for the Fluorimetric Determination of Nucleic Acids", *Analytical Biochemistry*, vol. 94, 1979, 259-269.

Marson, Charles M., "Reactions of Carbonyl Compounds with (Monohalo) Methyleniminium Salts (Vilsmeier Reagents)", *Tetrahedron*, vol. 48, No. 18: Tetrahedron Report No. 312, 1992, 3659-3726.

(56) References Cited

OTHER PUBLICATIONS

Matayoshi, et al., "Novel Fluoregenic Substrates for Assaying Retroviral Proteases by Resonance Energy Transfer", *Science*, vol. 247, Feb. 23, 1990, pp. 954-958.

Matselyukh, B. et al., "Interaction of cyanine dyes with nucleic acids : XXXI. using of polymethine cyanine dyes for the visualisation of DNA in agarose gels", *Journal of Biochemical and Biophysical Methods*, vol. 57, 2003, pp. 35-43.

Matsuyama, Tohey , "Staining of Living Bacteria with Rhodamine 123", *FEMS Microbiology Letters*, 21, 1984, 153-157.

McRae, E. G. et al., "The molecular exciton model", *Chemical Abstracts*, vol. 63, No. 3, Aug. 1965, 2525.

Morrison, Larry E. , "Detection of Energy Transfer and Fluorescence Quenching", *Nonisotopic DNA Probe Techniques*, L. Kricka, ed., 1992, 311-352.

Mushkalo, I. L. et al., "3,3'-Ethylenebis(benzothiazolium) salts and their biscyanine dyes", *Chemical Abstracts*, vol. 88, No. 4, Abstract #38941, 1978, 57.

Nouelry, Amine O. et al., "Two Proteins of a Plant DNA Virus Coordinate Nuclear and Plasmodesmal Transport", *Cell*, vol. 76, 1994, 925-932.

Park, Linda S. et al., "Characterization of the Cell Surface Receptor for a Multi-Lineage Colony-Stimulating Factor (CSF-2alpha)*", *J. Biol. Chem.*, vol. 261, No. 1, 1986, 205-210.

PCT/US04/40886,, PCT International Search Report for Application No. PCT/US04/40886, Aug. 18, 2005, 1-4.

Pennington, M. W. et al., "Synthesis of fluorogenic interleukin-1 beta converting enzyme substrate based on resonance energy transfer", *Pep. Res*, vol. 7, No. 2, 1994, 72-76.

Perkins, Thomas T. et al., "Direct Observation of Tube-Like Motion of a Single Polymer Chain", *Science* 264, 1994, 819-822.

Perkins, Thomas T. et al., "Relaxation of a Single DNA Molecule Observed by Optical Microscopy", Science 264, 1994, 822-825.

Petric, A et al., "Azido-Tetrazolo Isomerizations of Some Thiazolopyridines (1)", *J. Heterocyclin Chem.*, vol. 14, Oct. 1977, 1045-1047.

Przhiyalgovskaya, N. M. et al., "Carbocyanine Dyes with an O-hydroxyaryl Substituent in the Meso Position of the Polymethine Chain", *Translated from Khimiya Geterotsiklicheskikh Soedinenii*, No. 1, pp. 100-103, 1988, 83-86.

Rago, Randall et al., "DNA Fluorometric Assay in 96-Well Tissue Culture Plates Using Hoechst 33258 after Cell Lysis by Freezing in Distilled Water", *Analytical Biochemistry*, vol. 191, No. 31, 1990, 31-34.

Raju, B. et al., "A fluorescent indicator for measuring cytosolic free magnesium", *Am. J. Physiol.*, vol. 256, 1989, C540-C548.

Rye, H. et al., "High-sensitivity two-color detection of double-stranded DNA with a confocal fluorescence gel scanner using ethidium homodimer and thiazole orange", *Nucleic Acids Research*, vol. 19(2), 1990, pp. 327-333.

Rye, H. S. et al., "Stable Fluorescent Complexes of Double-Stranded DNA With Bis-Intercalating Asymmetric Cyanine Dyes: Properties and Applications", *Nucleic Acids Research*, vol. 20(11), 1992, pp. 2803-2812.

Rye, Hays S. et al., "Stable fluorescent complexes of double-stranded DNA with bis-intercalating asymmetric cyanine dyes: properties and applications.", *Chem. Abstracts*, vol. 117, No. 13, Abstract# 127607t, Sep. 28, 1992, 387.

Saikachi, Haruo et al., "Studies on Compounds Related to Pyrazine. III. Synthesis of 2-Substituted Thiazolo[b]duinozaline.", *Chem. & Pharm. Bull.*, vol. 9, No. 12, Dec. 1961, 941-944.

Saitoh, Yasushi et al., "Metaphase Chromosome Structure: Bands Arise from a Differential Folding Path of the Highly AT-Rich Scaffold", *Cell* 76, 1994, 609-622.

Sandler, Stanley R. et al., "Organic Functional Group Preparations", vol. 3, New York: *Academic Press*, 1972, 5-9.

Schlessinger, J et al., "Lateral transport of a lipid probe and labeled proteins on a cell membrane", *Science*, vol. 195, Jan. 1977, 307-309.

Schobel, Uwe et al., "New Donor-Acceptor Pair for Fluorescent Immunoassays by Energy Transfer", *Bioconjugate Chem.*, vol. 10, Oct. 9, 1999, 1107-1114.

Selvin, Paul R. , "Fluorescence Resonance Energy Transfer", *Methods in Enzymology*, vol. 246, 1995, 300-334.

Shevchenko, A. et al., "Mass Spectrometric Sequencing of Proteins Silver-Stained Polyacrylamide Gels", *Anal Chem* 68(5):, 1996, 850-8.

Simbera, J. et al., "Synthesis of polymethine dyes from 1-(3-chloro-2-tetrahydrofuryl)-4methylquinolinium chloride", *Chemical Abstracts*, vol. 89, No. 13, Abstract # 112299y, 1978, 151.

Singh, Tara et al., "Antimalarials. Distal Hydrazine derivatives of 7-chloroquinoline", *Journal of medicinal chemistry*, vol. 14, No. 6, 1971, 532-5.

Sizemore, Christine et al., "Quantitative analysis of Tn10 Tet repressor binding to a complete set of tet operator mutants", *Nucleic Acids Research*, vol. 18, No. 10, Oxford University Press, 1990, 2875-2880.

Sizemore, Ronald K. et al., "Alternate Gram Staining Technique Using a Fluorescent Lectin", *Applied and Environmental Microbiology*, vol. 56, No. 7, Jul. 1990, 2245-2247.

Smith, J. C. , "Potential-sensitive molecular probes in membranes of bioenergetic relevance", *Chemical Abstracts*, vol. 112, No. 19, Abstract# 174955m, 1990, 369.

Smith, J. C. , "Potential-sensitive molecular probes in membranes of bioenergetic relevance", *Biochimica et Niophysica Acta*, vol. 1016, No. 1, Mar. 15, 1990, 1-28.

Smith, Keith et al., "A Convenient Synthesis of 2-Substituted Thiazolo [4,5-b]pyridines via Directed Metalation", *Sulfur Letters*, vol. 18, No. 2 (not available online—BJC), 1995, 79-95.

Smith, Keith et al., "Convenient synthesis of 4-aminopyridine-3-thiol and several thiazolo[5,4-c]pyridines via direct ligation", *Chemistry and Industry*, vol. 9, May 2, 1988, 302-303.

Smith, Keith et al., "The synthesis of 2-substituted thiazolo[5,4-c]pyridines via directed methalation", *Sulfur Letters*, vol. 17, No. 4, 1994, 197-216.

Smith, P. K. et al., "Measurement of Protein Using Bicinchoninic Acid", *Analytical Biochemistry*, vol. 150, 1985, 76-85.

Spatola, et al., "Ch 5: Peptide Backbone Modifications: A Structure-Activity Analysis of Peptides Containing Amide Bond Surrogates, Conformational Constraints, and Rela", *Chemistry and Biochemistry of Amino Acids, Peptides and Proteins*, vol. 7, 1983, 267-357.

Staerk, Dan et al., "Bisintercalation of homodimeric thiazole orange dyes in DNA: Effect of modifying the linker", *Bioconjugate Chemistry*, vol. 8, No. 6, Nov. 1997, 869-877.

Steinberg, T. H. et al., "Rapid and Simple Single Nanogram Detection of Glycoproteins in Polycralamide Gels and on Electroblots", *Proteomics*, vol. 1, No. 7, 2001, 841-55.

Steinberg, Thomas H. et al., "Global Quantitative Phosphoprotein Analysis Using Multiplexed Proteomics Technology", *Proteomics*, vol. 3, Jul. 2003, 1128-1144.

Stetsenko, A. V. , "Benzimidocyanines", (*Ukrainian Version*) *Ukrainskii khimicheskii zhurnal* (*Ukrainian Chemistry Journal*), vol. 43, No. 1, Jan. 1977, 57-61.

Stevens, Anthony C. et al., "Synthesis of Protein-Reactive (Aminostyryl) pyridinium dyes", *Bioconjugate Chemistry*, vol. 4, 1993, 19-24.

Stezenko, A V. et al., "Cyanine Dyes, Derivatives", (*Ukrainian Version*) *Ukrainskii khimicheskii zhurnal* (*Ukrainian Chemistry Journal*), vol. 27, 1961, 237-240.

STN International, , "Accession No. 1959:5447", *CAPLUS Database*, Reg. Nos. 108519-76-2 and 109724-08-5, 2006.

Stratagene Catalog 1988, , "Stragagene Cloning Systems: Tools and Technology for Life Sciences", *Gene Characterization Kits*, Jan. 1, 1988, 39.

Strickland, R D. et al., "Dye-Binding Capacities of Eleven Electrophoretically Separated Serum Proteins", *Analytical Chemistry*, vol. 31, No. 8, Aug. 1959, 1408-1410.

Tijssen, J P. et al., "Localization of Polyphosphates in *Saccharomyces fragilis*, as Revealed by 4',6-Diamidino-2-Phenylindole Fluorescence", *Biochimica et Biophysica Acta*, vol. 721, Elsevier Biomedical Press, 1982, 394-398.

(56) References Cited

OTHER PUBLICATIONS

Timtcheva, I. et al., "Homodimeric monomethine cyanine dyes as fluorescent probes of biopolymers", *Journal of Photochemistry and Photobiology B: Biology*, vol. 58, No. 2-3, Nov. 2000, 130-135.

Turner, James A., "Regiospecific electrophilic substitution of aminopyridines: ortho lithiation of 2-, 3-, and 4-(pivaloylamino)pyridines", *Journal of Organic Chemistry*, vol. 48, 1983, 3401-3408.

Tyagi, et al., "Molecular Beacons: Probes that Fluoresce upon Hybridization", *Nature Biotechnology*, vol. 14, No. 3, Mar. 1996, 303-308.

Tyagi, Sanjay et al., "Multicolor molecular beacons for allele discrimination", *Nature Biotechnology*, vol. 16, 1998, 49-53.

Vahedi, et al., "An integrated method for mutation detection using on-chip sample preparation, single-stranded conformation polymorphism, and heteroduplex analysis", *Abstract of Electrophoresis* vol. 25(14), STN Accession No. 2004:652828, 2004, 2346-2356.

Vambutas, Vida et al., "Chloride-driven 3,3'-dipropylthiodicarbocyanine (DiSC3-(5)) and tetraphenylphosphonium cation (TPP+) uptake by thylakoids: inhibition of uptake by antibodies raised to the major polypeptides of the chloride efflux active particle(s)", *Biochimica et Biophysica Acta*, vol. 893, 1987, 69-74.

Vida, Thomas A. et al., "A New Vital Stain for Visualizing Vacular Membrane Dynamics and Endocytosis in Yeast", *The Journal of Cell Biology*, vol. 128, No 5, The Rockefeller University Press, Mar. 1, 1995, 779-792.

Visser, Nina V. et al., "Time-Resolved Fluorescence Investigations of the Interaction of the Voltage-Sensitive Probe RH421 with Lipid Membranes and Proteins", *Biochemistry*, vol. 34, American Chemical Society, 1995, 11777-11784.

Wang, Lijuan, "Synthesis of Hydroxyl Substituted Benzoxazol Hemicyanine and asym-Cyanine Dyes", *(Chinese Version) Journal of Wuhan Univ.*, No. 2, Feb. 1991, 73-77.

Wang, Q. M. et al., "Development of a conscious fluorescence assay for rhinovirus 14 3C protease using synthetic peptides", *Antiviral Chemistry & Chemotherapy*, vol. 8, No. 4, 1997, 303-310.

Watkins, T. I., "The Effect of Changing the Quarternary Grouping in Diminisium Bromide", *Trypanocides of the Phenanthridine Series.*, Part I., 1952, 3059-3064.

Wawzonek, Stanley, "Preparation and Proton Spectra of 1-Aryl-1,2-dihydro-2-Quinolones", *J. Heterocyclic Chem.*, 25, 1988, 381.

Weber, G et al., "Determination of the Absolute Quantum Yield of Fluorescent Solutions", *Transactions of the Faraday Society*, vol. 53, No. 1, Jan. 1957, 646-655.

Williams, Richard J. et al., "Comparison of Covalent and Noncovalent Labeling with Near-Infared Dyes for the High-Performance Liquid Chromatographic Determination of Human Serum Albumin", *Analytical Chemistry*, vol. 65, Mar. 1993, 601-605.

Wittung, Pernilla et al., "DNA-like double helix formed by peptide nucleic acid", *Nature*, 368, 1994, 561-563.

WO 1993/06482, PCT ISR, Jan. 11, 1993.

WO 1994/024213, PCT ISR, Aug. 4, 1994.

WO 1996/013552, PCT ISR, May 3, 1996.

WO 1996/036882, PCT ISR, Oct. 1, 1996.

WO 2000/066664, PCT International Search Report from PCT/US2000/011549, Sep. 7, 2000, 1-4.

WO 2005/056687, PCT ISR, Aug. 18, 2005.

WO 2005/056689, PCT ISR, Aug. 22, 2005.

WO 2005/083394, PCT ISR, Sep. 13, 2005.

WO 2006/124816, PCT ISR, Oct. 17, 2006.

Wu, Pengguang et al., "Resonance Energy Transfer: Methods and Applications", *Analytical Biochemistry*, vol. 218, No. 1, 1994, 1-13.

Yamana, Kazushige et al., "Bis-pyrene-labeled oligonucleotide: sequence specificity of excimer and monomer fluorescence changes upon hybridization with DNA", *Bioconjug Chem*, vol. 13, No. 6, 2002, 1266-73.

Yamana, Kazushige et al., "Fluorescence Detection of Specific RNA Sequence Using 2'-Pyrene-Modified Oligoribonucleotides", *Angewandte Chemie International Edition in English*, vol. 40 No. 6, 2001, 1104-1106.

Yan, J. X. et al., "Protein Phosphorylation: Technologies for the Identification of Phosphoamino Acids", *J. Chromatogr A*, vol. 808, 1998, 23-41.

Yoshimura, Akihiko et al., "Uncoating of Influenza Virus in Endosomes", *Journal of Virology*, vol. 51, No. 2, 1984, 497-504.

Zarling, David A. et al., "Mapping of Lymphocyte Surface Polypeptide Antigens by Chemical Cross-Linking with BSOCOES", *Journal of Immunology*, vol. 124 No. 2, 1980, 913-920.

Zipper, Hubert et al., "Investigations on DNA Intercalation and Surface Binding by SYBR Green I, its structure determination and methodological implications", *Nucleic Acids Research*, vol. 32(12), 2004, e103, 1-10.

* cited by examiner

FLUORESCENT CHEMICAL COMPOUNDS HAVING HIGH SELECTIVITY FOR DOUBLE STRANDED DNA, AND METHODS FOR THEIR USE

CROSS REFERENCE TO RELATED APPLICATIONS

The present application is a continuation of U.S. patent application Ser. No. 13/559,300, filed on Jul. 26, 2012, which is a continuation of U.S. patent application Ser. No. 13/104,413, filed on May 10, 2011, which is a continuation of U.S. patent application Ser. No. 12/573,809, filed on Oct. 5, 2009 (now U.S. Pat. No. 7,943,777), which is a continuation of U.S. patent application Ser. No. 11/432,814, filed May 11, 2006 (now U.S. Pat. No. 7,598,390), which claims priority to U.S. Provisional Patent Application Ser. No. 60/680,243, filed May 11, 2005, the contents of which are hereby incorporated herein by reference in their entirety.

FIELD OF THE INVENTION

The invention relates to stains that become fluorescent upon interaction with DNA. In particular, stains that exhibit higher fluorescence when contacted with double stranded DNA than when contacted with RNA and/or single stranded DNA, as well as various uses for the stains are disclosed.

DESCRIPTION OF RELATED ART

Stains and dyes are commonly used in chemical, biotechnological, and biomedical research. These two types of compounds are different in their properties, and in their intended uses.

Stains are chemical compounds that exhibit a detectable response when contacted with a particular target. In the absence of the target, a stain does not exhibit the detectable response. These properties make stains valuable in the detection of the presence or absence of a particular target in a sample. The detectable response can be qualitative or quantitative, depending on the compound, target, and assay parameters.

In comparison, dyes exhibit a detectable response regardless of the presence or absence of another material. Dyes are therefore useful to label a target. For example, an antibody can be labeled with a fluorescent dye molecule. The localization of the antibody in a cell or tissue can be monitored by fluorescence.

The detection and quantitation of DNA is a very common task in biotechnological research. Early chemical stains such as ethidium bromide are effective at staining DNA, but also stain RNA. DNA and RNA are often obtained together when isolated from natural sources. Stains that are not selective for DNA make quantitation of the isolated DNA difficult, requiring a purification step to be performed prior to quantitation. Stains find use in applications such as gel electrophoresis, PCR, real time PCR quantitation, DNA solution quantitation, microarrays, and RT-PCR.

Multiple nucleic acid stains are commercially available. The following is a representative listing of these materials.

Ethidium bromide is the most widely used nucleic acid stain, and is commercially available from a wide array of suppliers. Ethidium bromide is mutagenic, and its use requires significant care from the user to avoid contact with staining solutions.

PicoGreen is a stain selective for double stranded DNA (commercially available from Molecular Probes, Inc. (Eugene, Oreg.) since 1994). PicoGreen shows a greater than 1000 fold fluorescence enhancement upon binding to double stranded DNA, and much less enhancement upon binding to single stranded DNA or RNA.

OliGreen is a stain useful for the quantitation of single stranded DNA such as synthetic oligonucleotides. OliGreen has been commercially available from Molecular Probes, Inc. (Eugene, Oreg.) since 1994. Quantitation with OliGreen is about 10,000 times more sensitive than quantitation with UV absorbance methods, and at least 500 times more sensitive than detecting oligonucleotides on electrophoretic gels stained with ethidium bromide. This type of material is described in U.S. Pat. Nos. 5,436,134 and 5,658,751; Australian Patent Nos. 676,317 and 714,890; Canadian Patent No. 2,133,765; and European Patent Nos. 0,675,924 and 0,740,689.

RiboGreen is a stain that is useful for the quantitation of RNA in solution. RiboGreen has been commercially available from Molecular Probes, Inc. (Eugene, Oreg.) since 1997. This type of material is described in U.S. Pat. Nos. 5,658,751 and 5,863,753; Australian Patent No. 714,890; and European Patent No. 0,740,689.

SYBR Green I is stain selective for DNA (commercially available from Molecular Probes, Inc. (Eugene, Oreg.) since 1993). SYBR Green I has a fluorescence enhancement upon binding to DNA at least 10 fold greater than that of ethidium bromide, and a fluorescence quantum yield over five times greater than ethidium bromide (about 0.8 as compared to about 0.15). This type of material is described in U.S. Pat. Nos. 5,436,134 and 5,658,751; Australian Patent Nos. 676,317 and 714,890; Canadian Patent No. 2,133,765; and European Patent Nos. 0,675,924 and 0,740,689.

SYBR Safe is a nucleic acid stain that is at least twice as sensitive as ethidium bromide, yet exhibits reduced mutagenicity. SYBR Safe has been commercially available from Molecular Probes, Inc. (Eugene, Oreg.) since 2003. This type of material is described in U.S. Pat. Nos. 4,883,867, 4,957,870, 5,436,134, and 5,658,751; Australian Patent Nos. 676,317 and 714,890; Canadian Patent No. 2,133,765; and European Patent Nos. 0,675,924 and 0,740,689.

Hoechst 33258 (CAS 23491-45-4; Phenol, 4-[5-(4-methyl-1-piperazinyl)[2,5'-bi-1H-benzimidazol]-2'-yl]-, trihydrochloride) is a nuclear counterstain that emits blue fluorescence when bound to dsDNA. Hoechst 33258 has been commercially available from Molecular Probes, Inc. (Eugene, Oreg.) since 1992.

Dimeric cyanines TOTO-1, YOYO-1, and YO-PRO-1 are useful for the measurement of double stranded DNA, single stranded DNA, and RNA in solution. TOTO-1, YOYO-1, and YO-PRO-1 have been commercially available from Molecular Probes, Inc. (Eugene, Oreg.) since 1992. These types of materials are described in U.S. Pat. Nos. 5,321,130 and 5,582,977; Canadian Patent No. 2,119,126; and European Patent No. 0,605,655 B1.

Unsymmetrical cyanine dyes having similar spectral properties to intercalating cyanine dyes, but binding in the minor groove of DNA were reported in 2003 (Karlsson, H. J. et al., *Nucleic Acids Res.* 31(21): 6227-6234 (2003)). Compounds BEBO, BETO, and BOXTO were shown, and characterized using a variety of spectral measurements. Fluorescence quantum yield increased upon binding to DNA, but RNA binding results were not shown.

Despite the materials and methods that are currently available, there still exists a need for stains that are selective for double stranded DNA in the presence of RNA, single stranded DNA, or other biological materials.

SUMMARY OF THE INVENTION

Compounds are disclosed having high selectivity for double stranded DNA over RNA and single stranded DNA. The compounds act as fluorescent stains, where they exhibit fluorescent properties when illuminated in the presence of double stranded DNA, but exhibit reduced or no fluorescence in the presence of RNA, single stranded DNA, or in the absence of nucleic acids entirely. The compounds can contain the core structure of Compound (1A) or Compound (1B).

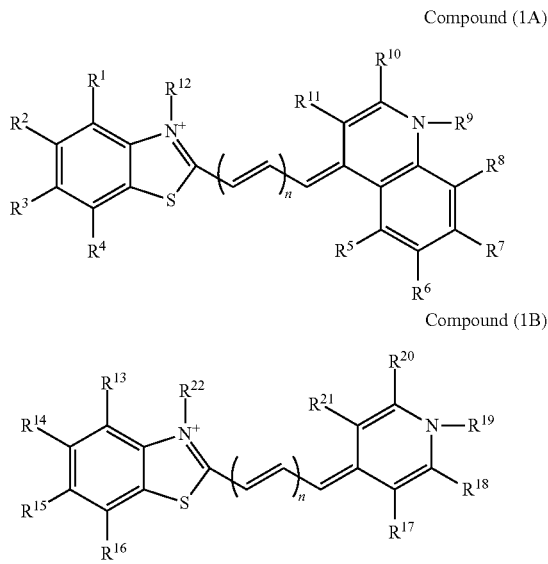

Compound (1A)

Compound (1B)

Also disclosed are methods for the preparation of the compounds, and methods for their use in detecting the presence or absence of double stranded DNA in a sample. The selectivity of the compounds for double stranded DNA over RNA and single stranded DNA enables detection of double stranded DNA in samples containing RNA and/or single stranded DNA.

DETAILED DESCRIPTION OF THE INVENTION

While compositions and methods are described in terms of "comprising" various components or steps (interpreted as meaning "including, but not limited to"), the compositions and methods can also "consist essentially of" or "consist of" the various components and steps, such terminology should be interpreted as defining essentially closed-member groups.

Compounds

A first embodiment of the invention is directed towards chemical compounds. The chemical compounds can be neutrally charged, positively charged, or negatively charged. When positively or negatively charged, the compound can include one or more counterions.

One embodiment of the invention is directed towards chemical compounds containing the core structure of Compound (1A).

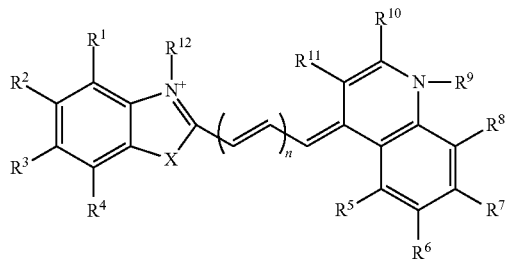

Compound (1A)

The double bond(s) in the center of Compound (1A) can be in either cis or trans configuration. For example, if X is nitrogen, the two nitrogens can be oriented on the same side of the central double bond (cis) or can be oriented across the central double bond (trans). Mixtures of both configurations are also possible in a sample of a particular compound.

The value n can be any non-negative integer. For example, n can be zero, 1, 2, 3, 4, 5, 6, 7, 8, and so on.

X can be oxygen or sulfur.

Groups $R^1$, $R^2$, $R^3$, $R^4$, $R^5$, $R^6$, $R^7$, $R^8$, $R^9$, $R^{10}$, and $R^{11}$ can independently comprise or be hydrogen (H), hydroxyl group (OH), alkoxy group (OR), thiol (SH), thioalkyl (SR), thioaryl (SAr), halogen (X), alkyl group, alkenyl group, alkynyl group, aromatic group, amine group (primary $NH_2$, secondary NHR, tertiary NR'R", or tertiary $NR'_2$), a reactive group, or a mixed group having combinations of two or more of these groups (for example, an alkyl group having thiol and amino substituents, an alkoxy group having amino substituents, and so on). Alternatively, one or more of these groups can be a linker group for covalently attaching Compound (1A) to another compound. Linking the linker group to another compound would afford a conjugate of Compound (1A).

In one embodiment, at least one of $R^1$, $R^2$, $R^3$, and $R^4$ comprises or is an aromatic group or an alkynyl group.

In one embodiment, $R^9$ comprises or is an aromatic group, alkyl-aromatic, or an alkynyl group.

In one embodiment, $R^{10}$ comprises or is an amine group.

In one embodiment, at least one of $R^1$, $R^2$, $R^3$, and $R^4$ comprises or is an aromatic group or an alkynyl group; and $R^9$ comprises or is an aromatic group, alkyl-aromatic, or an alkynyl group.

In one embodiment, at least one of $R^1$, $R^2$, $R^3$, and $R^4$ comprises or is an aromatic group or an alkynyl group; $R^9$ comprises or is an aromatic group, alkyl-aromatic group, or an alkynyl group; and $R^{10}$ comprises or is an amine group.

Group $R^{12}$ can be an alkyl group such as a $C_1$-$C_8$ alkyl group. The $C_1$-$C_8$ alkyl group can be a straight chain, branched, or cycloalkyl group. Examples of the $C_1$-$C_8$ alkyl group include methyl, ethyl, 1-propyl, 2-propyl, 1-butyl, 2-butyl, 1-pentyl, 1-hexyl, 1-heptyl, and 1-octyl. In a presently preferred embodiment, the $C_1$-$C_8$ alkyl group is a methyl group.

When Compound (1A) is a cationic or anionic structure, it can further comprise one or more appropriate counterions. For example, if Compound (1A) is cationic (positively charged), it can further comprise anions such as chloride, bromide, iodide, sulfate, and carbonate counterions. Alternatively, if Compound (1A) is anionic (negatively charged), it can further comprise cations such as potassium, sodium, ammonium, magnesium, and calcium.

An additional embodiment of the invention is directed towards chemical compounds containing the core structure of Compound (1B).

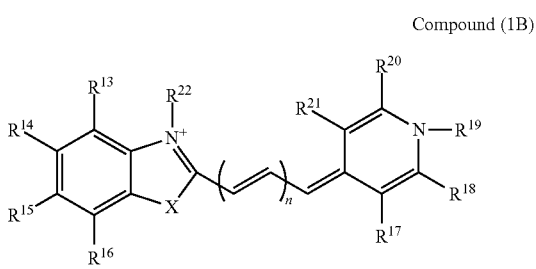

Compound (1B)

The double bond(s) in the center of Compound (1B) can be in either cis or trans configuration. For example, if X is nitrogen, the two nitrogens can be oriented on the same side of the central double bond (cis) or can be oriented across the central double bond (trans). Mixtures of both configurations are also possible in a sample of a particular compound.

The value n can be any non-negative integer. For example, n can be zero, 1, 2, 3, 4, 5, 6, 7, 8, and so on.

X can be oxygen or sulfur.

Groups $R^{13}$, $R^{14}$, $R^{15}$, $R^{16}$, $R^{17}$, $R^{18}$, $R^{19}$, $R^{20}$, and $R^{21}$ can independently comprise or be hydrogen (H), hydroxyl group (OH), alkoxy group (OR), thiol (SH), thioalkyl (SR), thioaryl (SAr), halogen (X), alkyl group, alkenyl group, alkynyl group, aromatic group, amine group (primary $NH_2$, secondary NHR, tertiary NR'R", or tertiary $NR'_2$), a reactive group, or a mixed group having combinations of two or more of these groups (for example, an alkyl group having thiol and amino substituents, an alkoxy group having amino substituents, and so on). Alternatively, one or more of these groups can be a linker group for covalently attaching Compound (1B) to another compound. Linking the linker group to another compound would afford a conjugate of Compound (1B).

In one embodiment, at least one of $R^{13}$, $R^{14}$, $R^{15}$, and $R^{16}$ comprises or is an aromatic group or an alkynyl group.

In one embodiment, $R^{19}$ comprises or is an aromatic group, alkyl-aromatic, or an alkynyl group.

In one embodiment, $R^{20}$ comprises or is an amine group.

In one embodiment, at least one of $R^{13}$, $R^{14}$, $R^{15}$, and $R^{16}$ comprises or is an aromatic group or an alkynyl group; and $R^{19}$ comprises or is an aromatic group, alkyl-aromatic, or an alkynyl group.

In one embodiment, at least one of $R^{13}$, $R^{14}$, $R^{15}$, and $R^{16}$ comprises or is an aromatic group or an alkynyl group; $R^{19}$ comprises or is an aromatic group, alkyl-aromatic, or an alkynyl group; and $R^{20}$ comprises or is an amine group.

Group $R^{22}$ can be an alkyl group such as a $C_1$-$C_8$ alkyl group. The $C_1$-$C_8$ alkyl group can be a straight chain, branched, or cycloalkyl group. Examples of the $C_1$-$C_8$ alkyl group include methyl, ethyl, 1-propyl, 2-propyl, 1-butyl, 2-butyl, 1-pentyl, 1-hexyl, 1-heptyl, and 1-octyl. In a presently preferred embodiment, the $C_1$-$C_8$ alkyl group is a methyl group.

When Compound (1B) is a cationic or anionic structure, it can further comprise one or more appropriate counterions. For example, if Compound (1A) is cationic (positively charged), it can further comprise anions such as chloride, bromide, iodide, sulfate, and carbonate counterions. Alternatively, if Compound (1A) is anionic (negatively charged), it can further comprise cations such as potassium, sodium, ammonium, magnesium, and calcium.

Substituents

The alkoxy group can generally be any unsubstituted alkoxy group or substituted alkoxy group. Unsubstituted alkoxy groups contain an oxygen connected to an alkyl group. Substituted alkoxy groups contain an oxygen connected to a substituted alkyl group. Examples of unsubstituted alkoxy groups include methoxy ($OCH_3$), ethoxy ($OCH_2CH_3$), propoxy ($OCH_2CH_2CH_3$), and higher straight chain alkoxy groups. Unsubstituted alkoxy groups also include branched or cyclic alkoxy groups. Examples of branched alkoxy groups include 2-propoxy ($OCH(CH_3)_2$), 2-butoxy ($OCH(CH_3)CH_2CH_3$), and higher branched alkoxy groups. Cyclic alkoxy groups have an oxygen connected to a cyclic group. Examples of cyclic alkoxy groups include cyclopropoxy (oxygen connected to a cyclopropane ring), cyclobutoxy (oxygen connected to a cyclobutane ring), cyclopentoxy (oxygen connected to a cyclopentane ring), cyclohexoxy (oxygen connected to a cyclohexane ring), and higher cyclic alkoxy groups.

The halogen can generally be any halogen. Halogen groups include chloro, fluoro, bromo, and iodo groups.

Alkyl groups can generally be any unsubstituted or substituted alkyl group. Unsubstituted alkyl groups contain only carbon and hydrogen atoms. Substituted alkyl groups can contain one or more non-carbon and non-hydrogen atoms such as oxygen, nitrogen, sulfur, halogens, and phosphorus.

Alkenyl groups can generally be any alkenyl group containing at least one carbon-carbon double bond. The most simple alkenyl group is a vinyl group ($-CH=CH_2$). Higher alkenyl groups include 1-propenyl ($-CH=CH_2CH_3$), 1-butenyl ($-CH=CH_2CH_2CH_3$), 2-butenyl ($-CH_2-CH=CHCH_3$), and 3-butenyl ($-CH_2CH_2CH=CH_2$). Substituted alkenyl groups can contain one or more non-carbon and non-hydrogen atoms such as oxygen, nitrogen, sulfur, halogens, and phosphorus.

Alkynyl groups can generally be any alkynyl group containing at least one carbon-carbon triple bond. The most simple alkynyl group is an ethynyl group ($-CCH$). Higher alkynyl groups include propargyl ($-CH_2CCH$), 2-butynyl ($-CH_2CCCH_3$), and 3-butynyl ($-CH_2CH_2CCH$).

A simple example of an aryl group is a phenyl group. The aryl group can be a simple unsubstituted aryl group containing carbon and hydrogen, or it can be a substituted aryl group. Aryl groups can include one or more aromatic rings. The aryl group can be a polycyclic aromatic hydrocarbon, or can be a heteroaryl group. Examples of aryl and heteroaryl groups include phenyl, 1-naphthyl, 2-naphthyl, 4-biphenyl, anthracenyl, acenaphthalenyl, acenaphthenyl, benzo[a]pyrenyl, benz[a]anthracenyl, 1-pyrrolyl, 2-pyrrolyl, 3-pyrrolyl, 3-pyrazolyl, 2 imidazolyl, 4-imidazolyl, pyrazinyl, 2-oxazolyl, 4-oxazolyl, 2-phenyl-4-oxazolyl, 5 oxazolyl, 3-isoxazolyl, 4-isoxazolyl, 5-isoxazolyl, 2-thiazolyl, 4-thiazolyl, 5-thiazolyl, 2 furyl, 3-furyl, 2-thienyl, 3-thienyl, 2-pyridyl, 3-pyridyl, 4-pyridyl, 2-pyrimidyl, 4 pyrimidyl, 5-benzothiazolyl, purinyl, 2-benzimidazolyl, 5-indolyl, 1-isoquinolyl, 5 isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl, and 6-quinolyl. Heteroatoms in the heteroaryl group can include one or more of nitrogen (N), oxygen (O), sulfur (S), and phosphorus (P).

Aryl groups can be connected to the central core structure Compound (1A) or Compound (1B), either directly by a covalent bond, or indirectly through one or more atoms. For example, N, O, P, or S atoms can be used to link the aryl group to Compound (1A) or Compound (1B). Examples of this include phenylamino ($NHC_6H_5$), diphenylamino ($N(C_6H_5)_2$), phenoxy ($OC_6H_5$), and thiophenyl ($SC_6H_5$). Alternatively, alkyl groups can be used to link the aryl group to Compound (1A) or Compound (1B). An example of this would be a benzyl group ($CH_2C_6H_5$; where a methylene $CH_2$ group connects the phenyl group to Compound (1A) or Compound (1B)), or a styrene group (CH=CH—C$_6$H$_5$).

Amine or amino groups can include NH$_2$, NHR, NR$_2$, and NR'R" groups. The R, R', and R" groups can be unsubstituted alkyl groups, substituted alkyl groups, unsubstituted alkenyl groups, substituted alkenyl groups, unsubstituted alkynyl groups, substituted alkynyl groups, unsubstituted aromatic groups, or substituted aromatic groups.

The chemical compound can comprise at least one reactive group capable of reacting with another species, such as an atom or chemical group to form a covalent bond, that is, a group that is covalently reactive under suitable reaction conditions, and generally represents a point of attachment for another substance, for example, a carrier molecule or a substrate. For example, the reactive group on a disclosed compound is a moiety, such as carboxylic acid or succinimidyl ester, on the compounds that can chemically react with a functional group on a different compound to form a covalent linkage. Reactive groups generally include nucleophiles, electrophiles and photoactivatable groups.

The reactive group can be covalently attached directly to the Compound (1A) core structure, or can be covalently attached to at least one of the R$^1$, R$^2$, R$^3$, R$^4$, R$^5$, R$^6$, R$^7$, R$^8$, R$^9$, R$^{10}$, and R$^{11}$ groups. The reactive group can be covalently attached directly to the Compound (1B) core structure, or can be covalently attached to at least one of the R$^{13}$, R$^{14}$, R$^{15}$, R$^{16}$, R$^{17}$, R$^{18}$, R$^{19}$, R$^{20}$, and R$^{21}$ groups Exemplary reactive groups include, but are not limited to, olefins, acetylenes, alcohols, phenols, ethers, oxides, halides, aldehydes, ketones, carboxylic acids, esters, amines, amides, cyanates, isocyanates, thiocyanates, isothiocyanates, hydrazines, hydrazones, hydrazides, diazo groups, diazonium groups, nitro groups, nitriles, mercaptans, sulfides, disulfides, sulfoxides, sulfones, sulfonic acid groups, sulfinic acid groups, acetals, ketals, anhydrides, sulfates, sulfenic acid groups, isonitriles, amidines, imides, imidates, nitrones, hydroxylamines, oximes, hydroxamic acid groups, thiohydroxamic acid groups, allenes, ortho esters, sulfites, enamines, ynamines, ureas, pseudoureas, semicarbazides, carbodiimides, carbamates, imines, azides, azo groups, azoxy groups, and nitroso groups. Reactive functional groups also include those used to prepare bioconjugates, for example, N-hydroxysuccinimide esters, maleimides, and the like. Methods to prepare each of these functional groups are well known in the art and their application to or modification for a particular purpose is within the ability of one of skill in the art (see, for example, Sandler and Karo, eds., Organic Functional Group Preparations, Academic Press, San Diego, 1989). Reactive groups include those shown in the following table.

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |

-continued

| Electrophilic Group | Nucleophilic Group | Resulting Covalent Linkage |
|---|---|---|
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula COΩ, where Ω is a good leaving group (e.g., succinimidyloxy (—OC$_4$H$_4$O$_2$) sulfosuccinimidyloxy (—OC$_4$H$_3$O$_2$—SO$_3$H), 1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$_a$, or —OCNR$_a$NHR$_b$, where R$_a$ and R$_b$, which may be the same or different, are C$_1$-C$_6$ alkyl, C$_1$-C$_6$ perfluoroalkyl, or C$_1$-C$_6$ alkoxy; or cyclohexyl, 3 dimethylaminopropyl, or N morpholinoethyl).
**Acyl azides can also rearrange to isocyanates Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327 (issued Feb. 3, 1998).

Where the reactive group is an activated ester of a carboxylic acid, such as a succinimidyl ester of a carboxylic acid, a sulfonyl halide, a tetrafluorophenyl ester, a pentafluorophenyl ester, or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

The reactive group can be a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

The reactive group can be a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. The reactive group can be a succinimidyl ester of a carboxylic acid, a maleimide, an iodoacetamide, or a silyl halide. The reactive group can be a succinimidyl ester of a carboxylic acid, a sulfonyl halide, a tetrafluorophenyl ester, an iosothiocyanates or a maleimide.

The selection of a covalent linkage to attach the compound to the carrier molecule or solid support typically depends on the chemically reactive group on the component to be conjugated. Examples of reactive groups include amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the component (typical for polysaccharides), or a variety of sites may occur (e.g. amines, thiols, alcohols, phenols), as is typical for proteins. A carrier molecule or solid support may be conjugated to more than one reporter molecule, which may be the same or different, or to a substance that is additionally modified by a hapten.

In an alternative embodiment, the present compound is covalently bound to a carrier molecule. If the compound has a reactive group, then the carrier molecule can alternatively be linked to the compound through the reactive group. The reactive group may contain both a reactive functional moiety and a linker, or only the reactive functional moiety.

A variety of carrier molecules exist. Examples of carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers.

The carrier molecule can comprise an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. Alternatively, the carrier molecule can be a hapten, a nucleotide, an oligonucleotide, a nucleic acid polymer, a protein, a peptide or a polysaccharide. The carrier molecule can be an amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. Alternatively, the carrier molecule is an antibody or fragment thereof, an antigen, an avidin or streptavidin, a biotin, a dextran, an antibody binding protein, a fluorescent protein, agarose, and a non-biological microparticle. The carrier molecule can be an antibody, an antibody fragment, antibody-binding proteins, avidin, streptavidin, a toxin, a lectin, or a growth factor. Examples of haptens include biotin, digoxigenin and fluorophores.

Antibody binding proteins include protein A, protein G, soluble Fc receptor, protein L, lectins, anti-IgG, anti-IgA, anti-IgM, anti-IgD, anti-IgE or a fragment thereof.

The chemical compound can be covalently bonded to another molecule such as an antibody, protein, peptide, polypeptide, amino acid, enzyme, nucleic acid, lipid, polysaccharide, drug, a bead, a solid support (such as glass or plastic), and so on.

The chemical compounds preferably exhibit little or no fluorescence when in the absence of nucleic acids. Fluorescence can be determined by illuminating the chemical compound with an appropriate wavelength, and monitoring emitted fluorescence. The chemical compounds preferably exhibit greater fluorescence when in the presence of DNA than when in the presence of RNA. The fluorescence in the presence of DNA to the fluorescence in the presence of RNA is determined using a fixed concentration of chemical compound, and a fixed concentration of DNA and RNA. Higher DNA/RNA fluorescence ratios are preferred for the detection of DNA in the presence of RNA. The DNA/RNA ratio is preferably greater than about 1. More preferred ratios are greater than about 2, greater than about 3, greater than about 4, greater than about 5, greater than about 6, greater than about 7, greater than about 8, greater than about 9, greater than about 10, greater than about 15, greater than about 20, greater than about 25, greater than about 30, greater than about 35, greater than about 40, greater than about 45, greater than about 50, greater than about 55, greater than about 60, greater than about 65, greater than about 70, greater than about 75, greater than about 80, greater than about 85, greater than about 90, greater than about 95, greater than about 100, greater than about 150, greater than about 200, and ranges between any two of these values.

The chemical compounds can also be characterized by their excitation and emission maxima wavelengths. For example, the excitation maximum can be about 450 nm to about 650 nm. Excitation maxima between these values can include about 450 nm, about 475 nm, about 500 nm, about 525 nm, about 550 nm, about 575 nm, about 600 nm, about 625 nm, about 650 nm, and ranges between any two of these values. For example, the emission maximum can be about 500 nm to about 675 nm. Emission maxima between these values can include about 500 nm, about 525 nm, about 550 nm, about 575 nm, about 600 nm, about 625 nm, about 650 nm, about 675 nm, and ranges between any two of these values.

Specific examples of chemical compounds include Compounds 16-35, 38-39, 43-53, 55-58, 60, 62, 64-81, 83, 85-89, 91-97, 99-106, and 109-112.

Compositions

An additional embodiment of the invention is directed towards compositions comprising one or more of the above described compounds. The compositions can comprise, consist essentially of, or consist of one or more of the above described compounds.

The compositions can comprise one, two, three, four, or more of the above described compounds. The compositions can further comprise a solvent. The solvent can be aqueous, non-aqueous, or a mixed aqueous/non-aqueous solvent system. Examples of solvents include water, methanol, ethanol, dimethylsulfoxide ("DMSO"), dimethylformamide ("DMF"), dimethylacetamide, and N-methylpyrrolidinone ("NMP"). The compositions can further comprise one or more salts or buffers.

The above described compounds can individually be present in the composition at a particular concentration. In one embodiment, the compound is present in a substantially pure form without other materials present (sometimes referred to as "neat"). Alternatively, the compounds can be present in a dry mixture or dissolved in a solvent or solvent system. When dissolved, the compound can generally be present at any concentration. The compound can be dissolved in a concentrated solution, or in a final "working" solution. For example, a compound can be present in a working solution at about 1 µM to about 10 µM. The concentrated solution can have the compound at a higher concentration such as about 10 µM, about 50 µM, about 100 µM, about 500 µM, about 1 mM, and ranges between any two of these values.

Kits

One embodiment of the invention is directed towards kits comprising one or more of the above described compounds. The kits can comprise one, two, three, four, or more of the above described compounds. The kit preferably comprises at least one container comprising at least one of the above described compounds. The kit can comprise multiple containers, such as a first container, a second container, a third container, and so on. The kit can comprise pipettes, droppers, or other sample handling devices. The kit can comprise a cuvette, microwell plate, or other test container suitable for use in an instrument that detects emitted fluorescent energy.

The kit can comprise positive and/or negative samples. Positive samples can comprise DNA, and/or DNA in the presence of RNA. Negative samples can comprise RNA without DNA, or samples lacking nucleic acids entirely. The kit can comprise DNA, RNA, or both DNA and RNA.

The kit can comprise one or more additional dyes or stains. For example, the kit can contain a total nucleic acid stain. The kit can contain a cell impermeant nucleic acid stain to aid in distinguishing live cells from dead cells.

The kits can further comprise an instruction protocol for their use. The kit can further comprise water, a buffer, a buffer salt, surfactants, detergents, salts, polysaccharides, or other materials commonly used in assaying biological systems. The kit can comprise solvents such as aqueous, non-aqueous, or a mixed aqueous/non-aqueous solvent systems.

Methods of Preparation

An additional embodiment of the invention is directed towards methods for the preparation of the above described compounds. Illustrative examples of these methods are described in the Examples below.

Additional embodiments of the invention include synthetic intermediates. Many synthetic intermediates are shown in the Examples section below. Examples of such intermediates include Compounds 2-15, 36-37, 40-42, 54, 59, 61, 63, 82, 84, 90, and 98.

Methods of Use

An additional embodiment of the invention is directed towards methods of using the above described compounds.

The above described compounds can be used in methods to detect the presence or absence of double stranded DNA in a sample. The method can comprise providing a sample suspected of containing double stranded DNA; contacting the sample with at least one of the above described chemical compounds to prepare a test sample; and illuminating the test sample with energy. The method can further comprise detecting emission of energy from the test sample after the illuminating step. The detecting step can be qualitative or quantitative. The method can further comprise calculating the concentration of double stranded DNA in the sample after the detecting step. The calculating step can comprise correlating the emitted fluorescent energy with the concentration of double stranded DNA in the sample.

The presence of an emitted fluorescent energy (or an increase in emitted fluorescent energy relative to a control) is indicative of the presence of double stranded DNA in the sample, while the absence of emitted fluorescent energy (or no increase or no change relative to a control) is indicative of the absence of DNA in the sample.

The methods can also be performed on "blank" or "control" samples. The blank or control samples can contain RNA but lack double stranded DNA, or can lack nucleic acids altogether.

The sample can generally be any type of sample. For example, the sample can be a cell or group of cells, an organism, cell lysates, a cell culture medium, a bioreactor sample, and so on. Alternatively, the sample can be a non-biological sample. The cells can be any type of cell, such as bacterial cells, fungal cells, insect cells, and mammalian cells. The sample can be a solid, a liquid, or a suspension. The sample can be a biological fluid such as blood, plasma, or urine. The sample can be a material immobilized in a gel, on a membrane, bound to a bead or beads, arranged in an array, and so on. The sample can be a partially or fully purified nucleic acid preparation in a buffer or in water.

The contacting step can be performed at any suitable temperature, and for any suitable length of time. Typically, the temperature will be ambient or room temperature, or at an elevated temperature such as 37° C. Examples of temperatures include about 20° C., about 25° C., about 30° C., about 35° C., about 37° C., about 40° C., about 42° C., and ranges between any two of these values. Temperatures higher than about 42° C., and temperatures lower than about 20° C. are also possible, depending on the sample tested. The length of time can generally be any length of time suitable for detection of a change in fluorescence. Examples of lengths of time include about 10 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes, about 180 minutes, about 240 minutes, about 300 minutes, about 360 minutes, about 420 minutes, about 480 minutes, about 540 minutes, about 600 minutes, and ranges between any two of these values. Further extended lengths of time are also possible, depending on the sample tested. The contacting step is preferably performed with the test sample protected from light.

The compound or compounds can be used at generally any concentration suitable to produce a detectable emitted fluorescent energy signal in the presence of double stranded DNA. Example concentration ranges include about 10 nM to about 1 mM. Examples of concentrations include about 10 nM, about 100 nM, about 1 µM, about 2 µM, about 3 µM, about 4 µM, about 5 µM, about 6 µM, about 7 µM, about 8 µM, about 9 µM, about 10 µM, about 100 µM, about 1 mM, and ranges between any two of these values.

The excitation energy can be applied to the test sample in a variety of ways during the illuminating step. Suitable equipment includes hand-held ultraviolet lamps, mercury arc lamps, xenon lamps, lasers (such as argon and YAG lasers), and laser diodes. These illumination sources are typically optically integrated into laser scanners, fluorescence microplate readers or standard or microfluorometers.

The detecting step can be performed by visual inspection, or by the use of a variety of instruments. Examples of such instruments include CCD cameras, video cameras, photographic film, laser scanning devices, fluorometers, photodiodes, quantum counters, epifluorescence microscopes, scanning microscopes, flow cytometers, fluorescence microplate readers, or by amplification devices such as photomultiplier tubes.

The detecting step can be performed at a single point in time, can be performed at multiple points in time, or can be performed continuously.

The methods can be used in conjunction with experimental systems such as DNA minipreps, flow cytometry, fluorescence microscopy, real time PCR, double stranded DNA quantitation, microarray hybridizations, double stranded DNA detection in gels, and so on.

The following examples are included to demonstrate preferred embodiments of the invention. It should be appreciated by those of skill in the art that the techniques disclosed in the examples which follow represent techniques discovered by the inventor(s) to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Preparation of Compound (2)

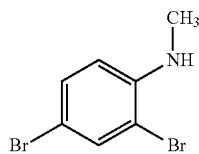

To 10 g of N-methylaniline in 200 mL acetic acid at room temperature 11.3 mL bromine was added and the mixture was stirred for several hours. Volatile components were evaporated under reduced pressure and the residue was dissolved in chloroform and washed with saturated solutions of NaHCO$_3$ and Na$_2$S$_2$O$_3$. The crude was purified on a silica gel column with ethyl acetate and hexanes.

Example 2

Preparation of Compound (3)

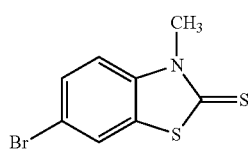

To 3.5 g of NaH (60% by weight in dispersion oil and washed with hexanes) in 200 mL of DMF 18.5 g of Compound (2) was added, followed by 6.2 mL of CS$_2$. The mixture was heated at 100° C. for 4 hours. Water was added and the solid was filtered and purified by silica gel column with ethyl acetate and hexanes.

Example 3

Preparation of Compound (4)

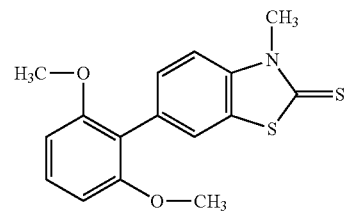 [SMILES: COc1cccc(OC)c1-c1ccc2c(c1)sc(=S)n2C]

To 9.5 g of Compound (3), 10 g of 2,6-dimethoxyphenylboronic acid and 1 g of triphenylphosphine in 300 mL of isopropyl alcohol and 50 mL of toluene was added a solution of 6 g of K$_2$CO$_3$ in 40 mL of water and 0.25 g of palladium (II)acetate. The resulting mixture was heated at 100° C. for 5 hours. The solvent was removed and the residue was dissolved in CHCl$_3$ and washed with water. The crude product was purified on a silica gel column with ethyl acetate and hexanes.

Example 4

Preparation of Compound (5)

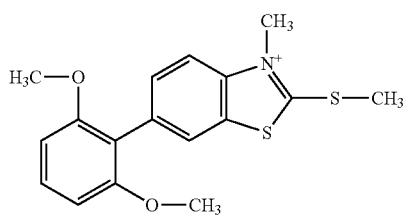

Compound (3) was coupled with 2,6-dimethoxyphenylboronic acid as described in Example 3 (Preparation of compound (4)). This was followed by quarternization with methyl tosylate at about 130° C. for 1.5 hours.

Example 5

Preparation of Compound (6)

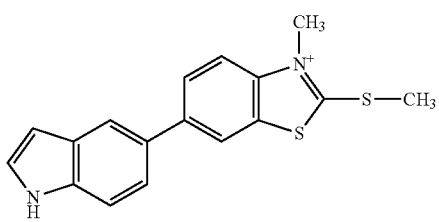 [SMILES: CSc1sc2cc(-c3ccc4[nH]ccc4c3)ccc2[n+]1C]

Compound (3) was coupled with 5-indolylboronic acid using the conditions described in Example 3 (Preparation of compound (4)). This was followed by quarternization with methyl tosylate at about 130° C. for 1.5 hours.

Example 6

Preparation of Compound (7)

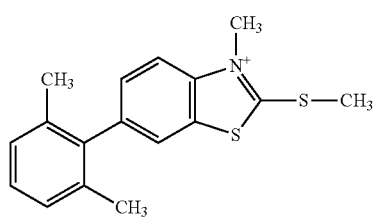 [SMILES: CSc1sc2cc(-c3c(C)cccc3C)ccc2[n+]1C]

Compound (3) was coupled with 2,6-dimethylphenylboronic acid using the conditions described in Example 3 (Preparation of compound (4)). This was followed by quarternization with methyl tosylate at about 130° C. for 1.5 hours.

Example 7

Preparation of Compound (8)

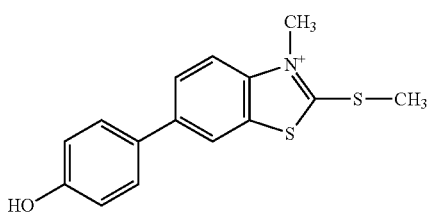 [SMILES: CSc1sc2cc(-c3ccc(O)cc3)ccc2[n+]1C]

Compound (3) was coupled with 4-hydroxyphenylboronic acid using the conditions described in Example 3 (Preparation of compound (4)). This was followed by quarternization with methyl tosylate at about 130° C. for 1.5 hours.

Example 8

Preparation of Compound (9)

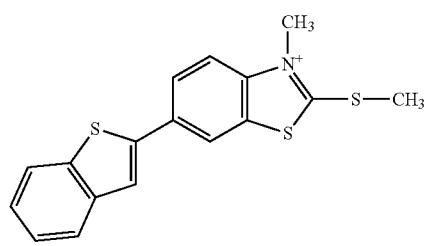 [SMILES: CSc1sc2cc(-c3cc4ccccc4s3)ccc2[n+]1C]

Compound (3) was coupled with benzothiaphen-2-yl boronic acid using the conditions described in Example 3 (Preparation of compound (4)). This was followed by quarternization with methyl tosylate at about 130° C. for 1.5 hours.

Example 9

Preparation of Compound (10)

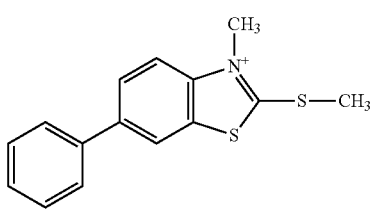 [SMILES: CSc1sc2cc(-c3ccccc3)ccc2[n+]1C]

Compound (3) was coupled with phenylboronic acid using the conditions described in Example 3 (Preparation of compound (4)). This was followed by quarternization with methyl tosylate at about 130° C. for 1.5 hours.

Example 10

Preparation of Compound (11)

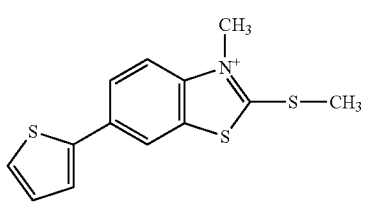 [SMILES: CSc1sc2cc(-c3cccs3)ccc2[n+]1C]

Compound (3) was coupled with thiophene-2-boronic acid using the conditions described in Example 3 (Preparation of compound (4)). This was followed by quarternization with methyl tosylate at about 130° C. for 1.5 hours.

Example 11

Preparation of Compound (12)

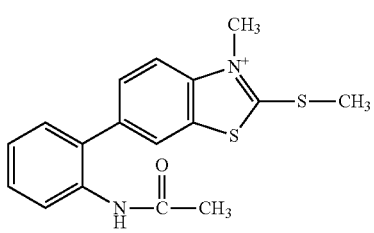 [SMILES: CSc1sc2cc(-c3ccccc3NC(C)=O)ccc2[n+]1C]

Compound (3) was coupled with 2-acetamidobenzeneboronic acid using the conditions described in Example 3

(Preparation of compound (4)). This was followed by quarternization with methyl tosylate at about 130° C. for 1.5 hours.

Example 12

Preparation of Compound (13)

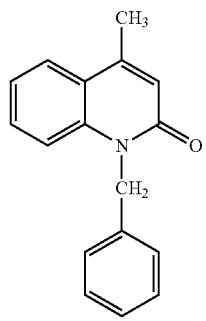 [SMILES: Cc1cc(=O)n(Cc2ccccc2)c2ccccc12]

To 1.5 g NaH (60% in dispersion oil and washed with hexanes) in 50 ml DMF 1.5 g of 2-hydroxyl-4-methylquinoline was added followed by 4.5 mL of benzyl bromide. The mixture was stirred at room temperature for 2 hours. Solvent was removed under reduced pressure and the residue was dissolved in CHCl$_3$ and washed with water. The product was obtained by silica gel column purification with ethyl acetate and hexanes.

Example 13

Preparation of Compound (14)

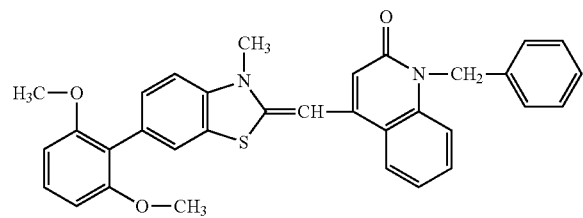 [SMILES: COc1cccc(OC)c1-c1ccc2c(c1)SC(=Cc1cc(=O)n(Cc3ccccc3)c3ccccc13)N2C]

To 0.5 g of Compound (5), 0.25 g of Compound (13) in 10 mL of methylene chloride, 0.7 mL of diisopropylethylamine and 0.9 mL of trimethylsilyl trifluoromethanesulfonate were added, and the resulting mixture was heated at reflux for 1 hour. The mixture was washed with water, and the product was purified on a silica gel column with ethyl acetate and hexanes.

Example 14

Preparation of Compound (15)

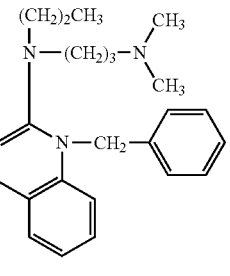

A mixture of 0.1 g of Compound (14) and 0.06 mL of phosphorus oxychloride was refluxed in 3 mL of dichloroethane for 5 hours. The mixture was washed with water and the solvent was removed. The residue was stirred in ethyl acetate and filtered to obtain the product.

Example 15

Preparation of Compound (16)

A mixture of 0.1 g of Compound (15) and 0.3 mL N,N-dimethyl-N'-propyl-1,3-propanediamine was heated at 55° C. in 3 mL of 1,2-dichloroethane for 3 hours. The solvent was removed and the product was purified on a silica gel column with chloroform and methanol.

Example 16

Preparation of Compound (17)

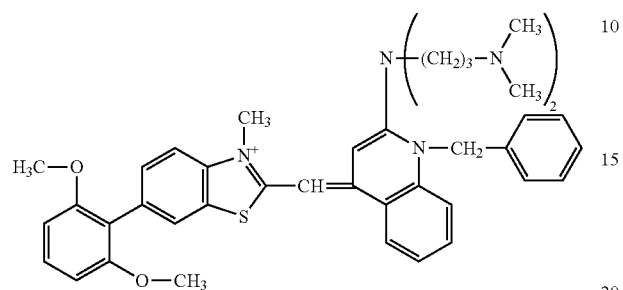

Compound (17) was prepared by following the same procedure used to prepare Compound (16), substituting 3,3'-iminobis(N,N-dimethyl propylamine) for N,N-dimethyl-N'-propyl-1,3-propanediamine.

Example 17

Preparation of Compound (18)

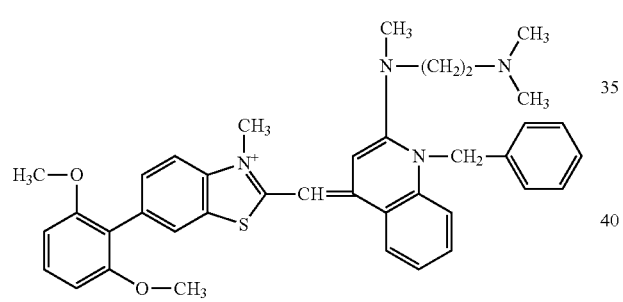

Compound (18) was prepared by following the same procedure used to prepare Compound (16), substituting N,N,N'-trimethylethanediamine for N,N-dimethyl-N'-propyl-1,3-propanediamine.

Example 18

Preparation of Compound (19)

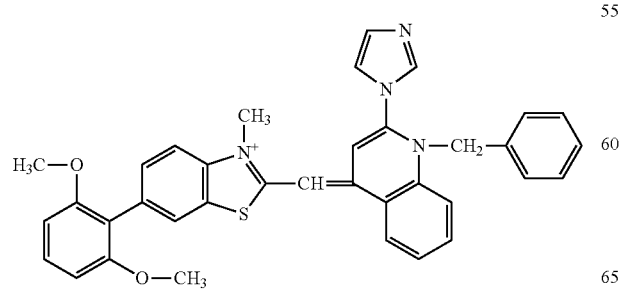

A mixture of 12 mg of Compound (15) and 2 mg of imidazole was stirred at room temperature in 2 mL of methylene chloride for 2 hours. At the end of the period, 2 mL of ethyl acetate was added and stirring was continued overnight. The product was obtained by centrifugation.

Example 19

Preparation of Compound (20)

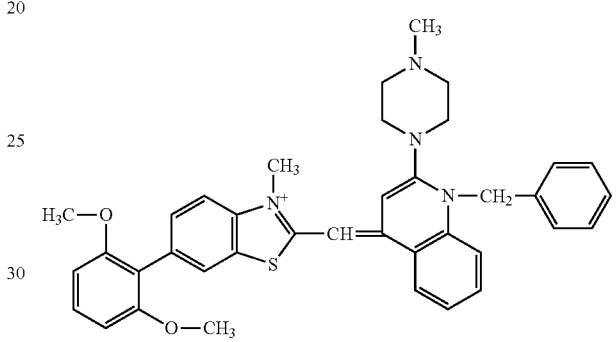

Compound (20) was prepared by following the same procedure used to prepare Compound (16), substituting 1-methyl-piperazine for N,N-dimethyl-N'-propyl-1,3-propanediamine.

Example 20

Preparation of Compound (21)

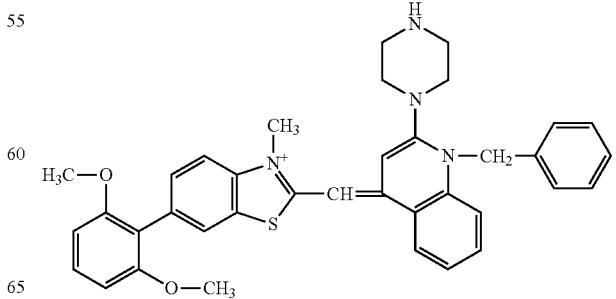

Compound (21) was prepared by following the same procedure used to prepare Compound (16), substituting piperazine for N,N-dimethyl-N'-propyl-1,3-propanediamine.

Example 21

Preparation of Compound (22)

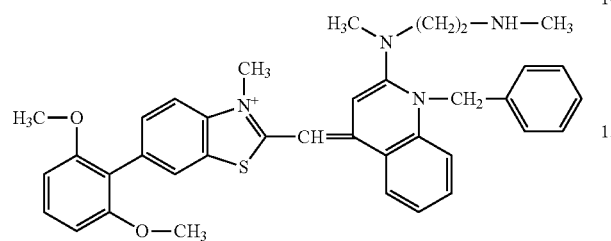

Compound (22) was prepared by following the same procedure used to prepare Compound (16), substituting N,N'-dimethylethanediamine for N,N-dimethyl-N'-propyl-1,3-propanediamine.

Example 22

Preparation of Compound (23)

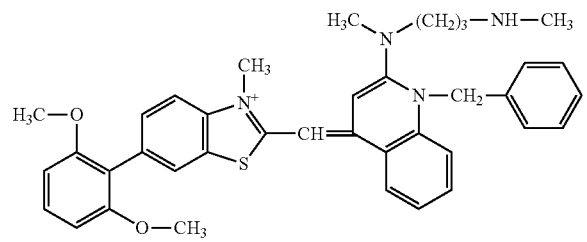

Compound (23) was prepared by following the same procedure used to prepare Compound (16), substituting N,N'-dimethylpropanediamine for N,N-dimethyl-N'-propyl-1,3-propanediamine.

Example 23

Preparation of Compound (24)

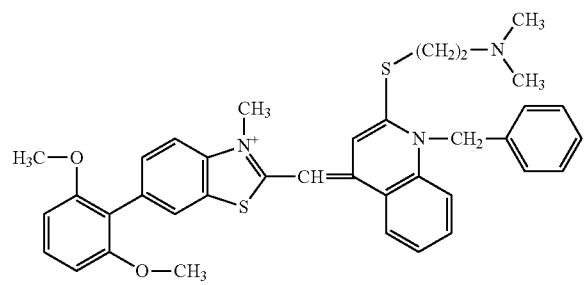

A mixture of 18 mg of Compound (15), 5 mg of 2-N,N-dimethylaminoethanethiol hydrochloride, and 9 uL of triethylamine in 5 mL of methylene chloride was stirred at room temperature for 1.5 hours. All volatile components were removed under reduced pressure and the crude was purified on a silica gel column using chloroform and methanol.

Example 24

Preparation of Compound (25)

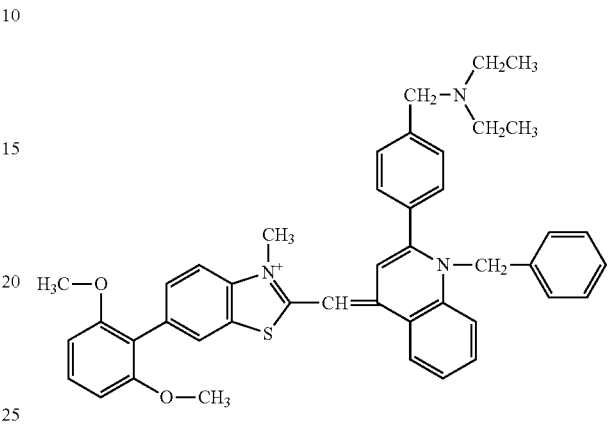

To 0.35 g of 4-diethylaminomethyl-bromobenzene in 4 mL dry THF at −78° C. under nitrogen, 0.32 mL of a 2.5 M n-butyllithium was introduced followed by 0.1 g of Compound (13) in 2 mL THF. The reaction was stirred at the low temperature for 1 hour before the addition of 1 mL acetic acid. The mixture was stirred at room temperature for another hour and the solvent was removed and the residue was further pumped for an hour. To the residue, 0.2 g of Compound (5), 2 mL of dichloroethane and 0.35 mL of triethylamine were added and stirred at room temperature for one hour. The resulting mixture was washed with dilute sodium hydroxide and purified on a silica gel column chromatography using chloroform and methanol.

Example 25

Preparation of Compound (26)

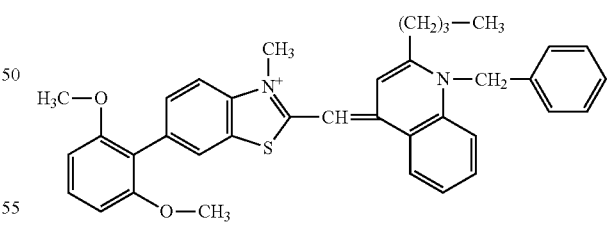

To 50 mg of Compound (13) in 5 mL of THF at −78° C. under nitrogen, 0.16 mL of a 2.5 M n-butyllithium was added. After 30 minutes at the low temperature, 0.5 mL of acetic acid was added and the resulting mixture was stirred at room temperature for 1 hour. Volatile components were evaporated under reduced pressure and the residue further pumped in vacuo for 30 minutes. To the resulting residue in 10 mL of methylene chloride, 50 mg of Compound (5) and 84 uL of triethylamine were added and the mixture was stirred at room temperature for several hours. The organic layer was washed with dilute HCl and NaCl and the crude was purified on silica gel using ethyl acetate, chloroform and methanol.

Example 26

Preparation of Compound (27)

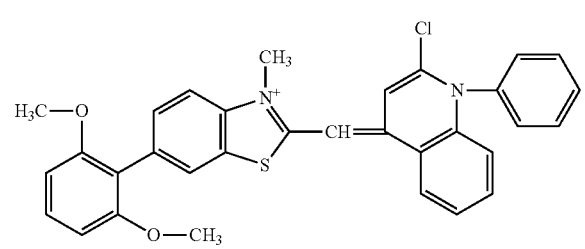 [SMILES: COc1cccc(OC)c1-c1ccc2c(c1)sc(C=C1C=C(Cl)N(c3ccccc3)c3ccccc31)[n+]2C]

Compound (27) was prepared by following the same procedure used to prepare Compound (15), using 4-methyl-1-phenyl-2(H)-quinolone as the starting material.

Example 27

Preparation of Compound (28)

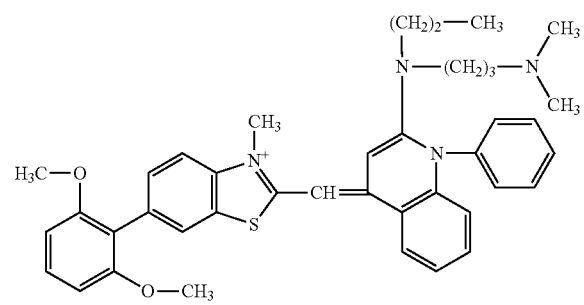

Compound (28) was prepared by following the same procedure used to prepare Compound (16), using Compound (27) as the starting material.

Example 28

Preparation of Compound (29)

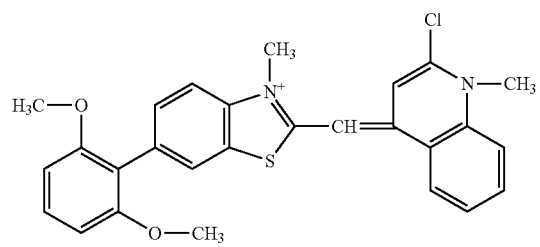

Compound (29) was prepared by following the same procedure used to prepare Compound (15), using 1,4-dimethyl-2(H)-quinolinone as the starting material.

Example 29

Preparation of Compound (30)

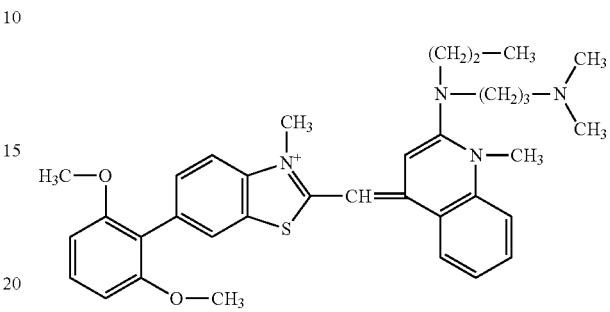

Compound (30) was prepared by following the same procedure used to prepare Compound (16), using Compound (29) as the starting material.

Example 30

Preparation of Compound (31)

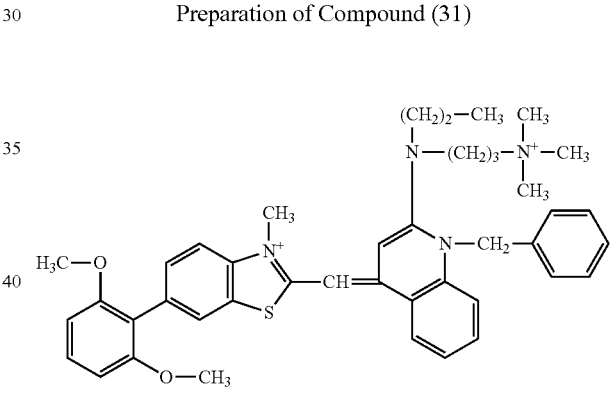

A mixture of 4 mg of Compound (16) and 0.05 mL of methyl iodide in 0.5 mL DMF was heated at 60° C. overnight. The solvent was removed and the product was purified on a LH-20 column with water.

Example 31

Preparation of Compound (32)

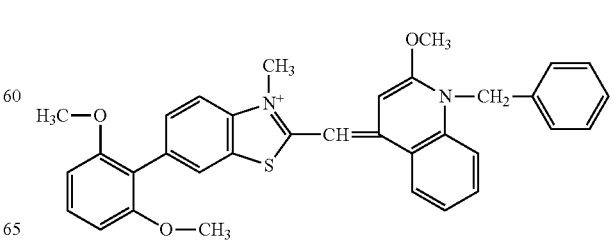

A mixture of 20 mg of Compound (15) and 0.05 mL triethylamine in 2 mL methanol was heated at 60° C. for 1 day. The product was precipitated out by the addition of ethyl acetate.

Example 32

Preparation of Compound (33)

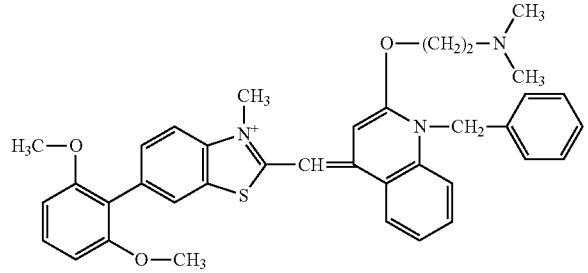

Compound (33) was prepared by following the same procedure used to prepare Compound (32), using 2-dimethylaminoethanol instead of methanol.

Example 33

Preparation of Compound (34)

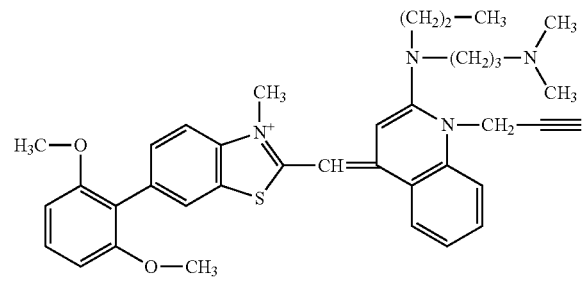

Compound (34) was prepared by following the same procedure used to prepare Compound (16) using 4-methyl-1-propargyl-2(H)-quinolinone as the starting material to generate the intermediate 2-chloro derivative, which in turn was reacted with N,N-dimethyl-N'-propylpropanediamine to generate the target.

Example 34

Preparation of Compound (35)

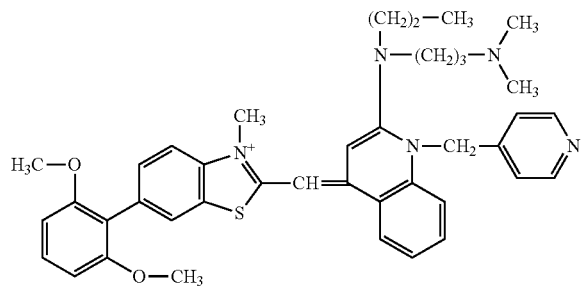

Compound (35) was prepared by following the same procedure used to prepare Compound (16), using Compound (41) as the starting material.

Example 35

Preparation of Compound (36)

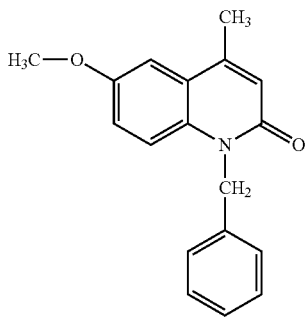 [SMILES: COc1ccc2c(c1)c(C)cc(=O)n2Cc1ccccc1]

To 1 g of N-benzyl-4-methoxyaniline in 10 mL of toluene was added 0.72 mL of diketene. The mixture was stirred overnight and the solvent was removed under reduced pressure. To the residue, 8 mL of a 1:1 v/v mix of $H_2SO_4$:HOAc was added and heated at 50° C. overnight. The mixture was poured onto ice water and extracted with ethyl acetate. The crude material was purified on silica gel using ethyl acetate and hexanes.

Example 36

Preparation of Compound (37)

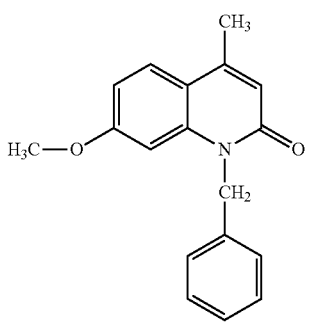 [SMILES: COc1ccc2c(C)cc(=O)n(Cc3ccccc3)c2c1]

Compound (37) was prepared by following the same procedure used to prepare Compound (36), using N-benzyl-3-methoxyaniline in place of N-benzyl-4-methoxyaniline

Example 37

Preparation of Compound (38)

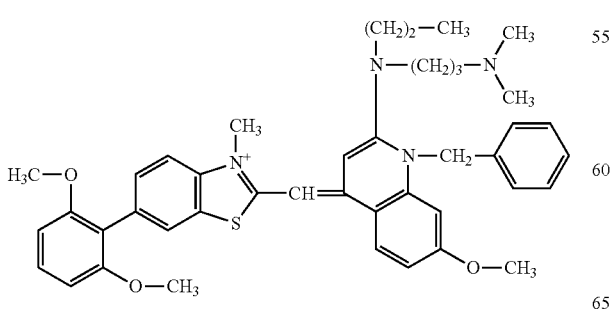

Compound (38) was prepared by following the same procedure used to prepare Compound (16), using Compound (37) as the starting material.

Example 38

Preparation of Compound (39)

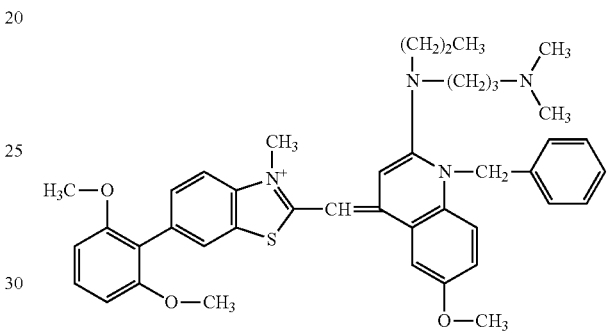

Compound (38) was prepared by following the same procedure used to prepare Compound (16), using Compound (36) as the starting material.

Example 39

Preparation of Compound (40)

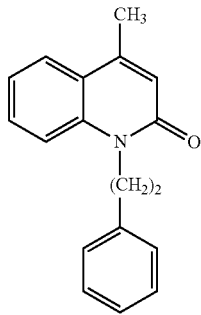

Compound (40) was prepared by following the same procedure used to prepare Compound (13), using bromoethylbenzene as the starting material.

Example 40

Preparation of Compound (41)

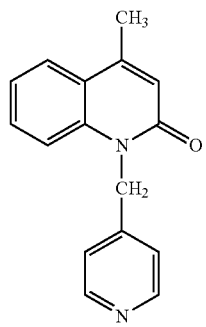 [SMILES: Cc1cc(=O)n(Cc2ccncc2)c2ccccc12]

Compound (41) was prepared by following the same procedure used to prepare Compound (13), using bromoethylpyridine as the starting material.

Example 41

Preparation of Compound (42)

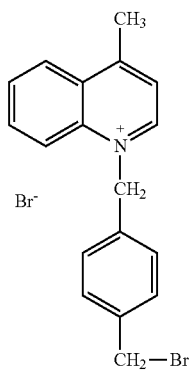

A mixture of 0.5 g of lepidine and 2.76 g of p-xylylene dibromide was refluxed in 10 mL of ethyl acetate for 1 hour. The product was obtained by filtration.

Example 42

Preparation of Compound (43)

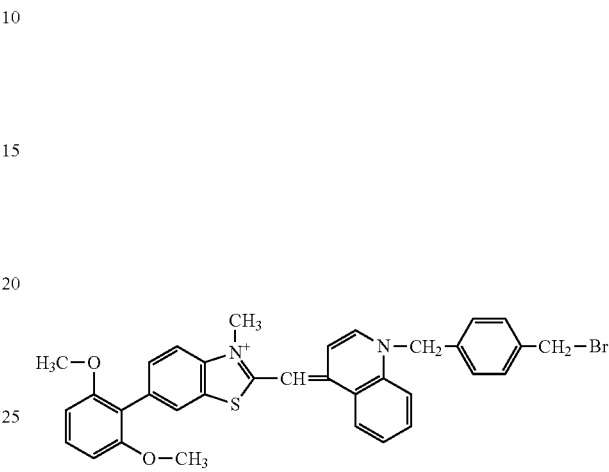

A mixture of 0.32 g of Compound (5), 0.26 g of Compound (42), 0.4 g of N-ethylmaleimde, and 0.16 mL of diisopropylethylamine was stirred in 5 mL of methylene chloride at 0° C. for 1 hour. Next, 20 mL of ethyl acetate was added, and the product was collected by filtration.

Example 43

Preparation of Compound (44)

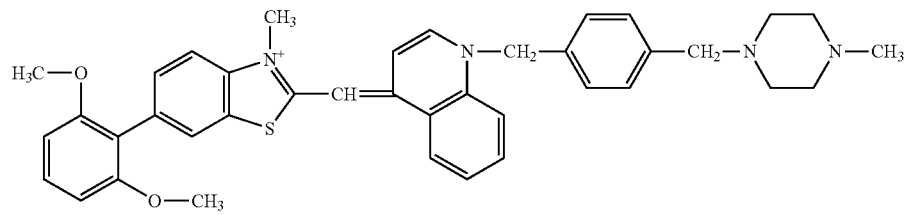

The compound was obtained by reacting Compound (43) with an excess amount of N-methylpiperazine in DMF at room temperature for 3 hours.

Example 44

Preparation of Compound (45)

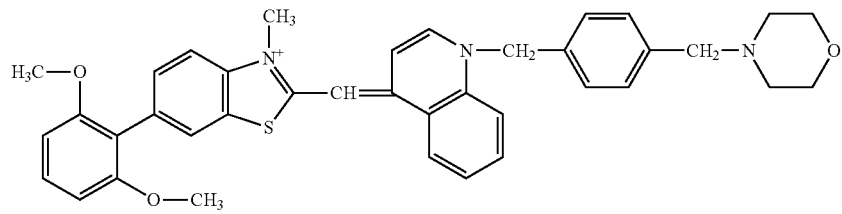 [SMILES: COc1cccc(OC)c1-c1ccc2c(c1)sc(C=C1C=CN(Cc3ccc(CN4CCOCC4)cc3)c3ccccc31)[n+]2C]

The compound was obtained by reacting Compound (43) with an excess amount of morpholine in DMF at room temperature for 3 hours.

Example 45

Preparation of Compound (46)

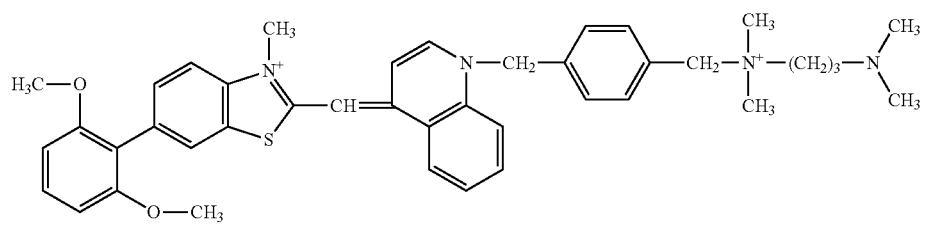

The compound was obtained by reacting Compound (43) with an excess amount of N,N,N',N'-tetramethylpropanediamine in DMF at 50° C. for 4 hours.

Example 46

Preparation of Compound (47)

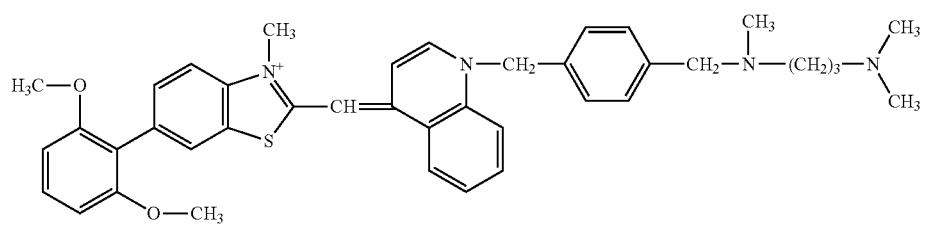

The compound was obtained by reacting Compound (43) with an excess amount of N,N,N'-trimethylpropanediamine in DMF at 50° C. for 2 hours.

Example 47

Preparation of Compound (48)

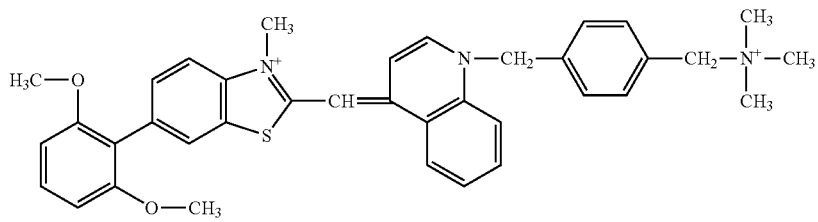

The compound was obtained by reacting Compound (43) with an excess amount of trimethylamine in DMF at 50° C. for 4 hours.

Example 48

Preparation of Compound (49)

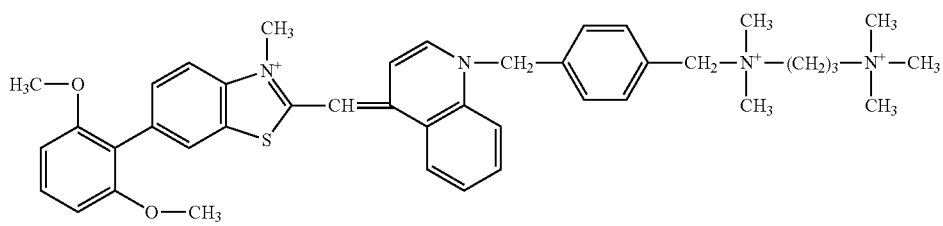

The compound was obtained by reacting Compound (46) with an excess amount of methyl iodide in DMF at room temperature overnight.

Example 49

Preparation of Compound (50)

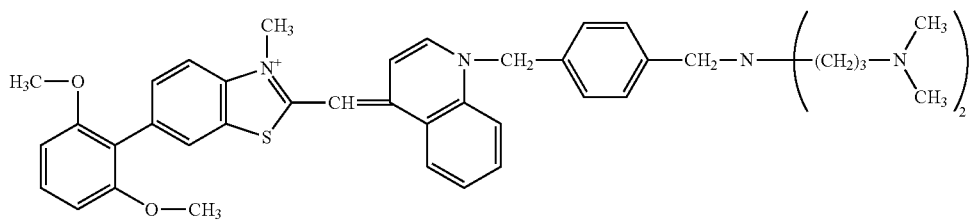

The compound was obtained by reacting Compound (46) with an excess amount of 3,3'-iminobis(N,N-dimethylpropylamine) in DMF at room temperature for 4 hours.

Example 50

Preparation of Compound (51)

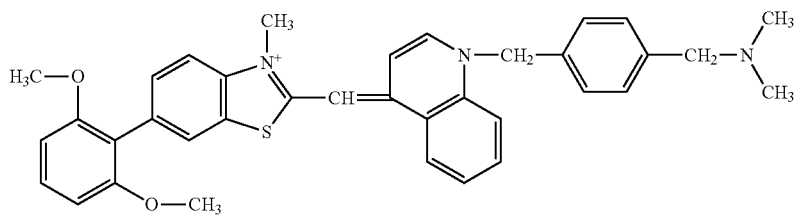

The compound was obtained by reacting Compound (46) with an excess amount of dimethylamine in DMF at 60° C. for 1 hour.

Example 51

Preparation of Compound (52)

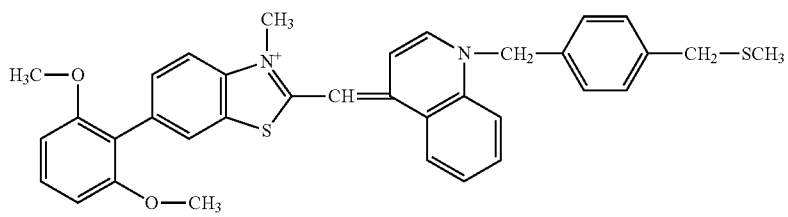 [SMILES: COc1cccc(OC)c1-c1ccc2c(c1)sc(C=C1C=CN(Cc3ccc(CSC)cc3)c3ccccc31)[n+]2C]

A mixture of 0.2 g of Compound (5), 0.16 g of Compound (42), and 0.2 mL of triethylamine was stirred in 10 mL of dichloroethane at room temperature for 1 hour. The reaction mixture was washed with water and brine, and the crude material was purified using HPLC with chloroform and methanol.

Example 52

Preparation of Compound (53)

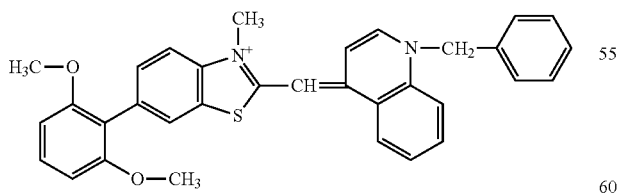

A mixture of 10 mg of Compound (5), 7 mg of 1-benzyl-4-methylquinolinium bromide, and 0.1 mL of triethylamine was stirred in 1 mL of methanol for 2 hours. Volatile components were removed under reduced pressure, and the crude was purified using silica gel chromatography with chloroform and methanol.

Example 53

Preparation of Compound (54)

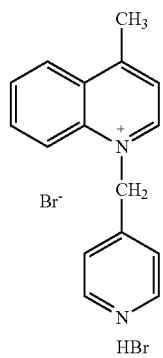

A mixture of 4-bromomethylpyridine HBr and 2 equivalents of lepidine was heated at 120° C. for one hour, and followed by stirring in ethyl acetate for several hours. The product was collected by filtration.

Example 54

Preparation of Compound (55)

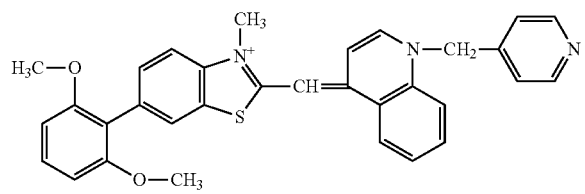 [SMILES: COc1cccc(OC)c1-c1ccc2c(c1)sc(C=C1C=CN(Cc3ccncc3)c3ccccc31)[n+]2C]

A mixture of 10 mg of Compound (5), 5 equivalents of Compound (54) and 0.1 mL of triethylamine was stirred in 0.5 mL of DMF for 1 hour. Volatile components were removed under reduced pressure, and the crude material was purified using silica gel chromatography with chloroform and methanol.

Example 55

Preparation of Compound (56)

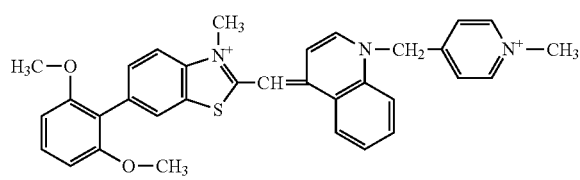

A mixture of 3 mg of Compound (55) and about 0.2 mL of iodomethane was stirred at room temperature overnight in 1 mL of DMF. Ethyl acetate (4 mL) was added and after stirring for an additional hour, the product was filtered.

Example 56

Preparation of Compound (57)

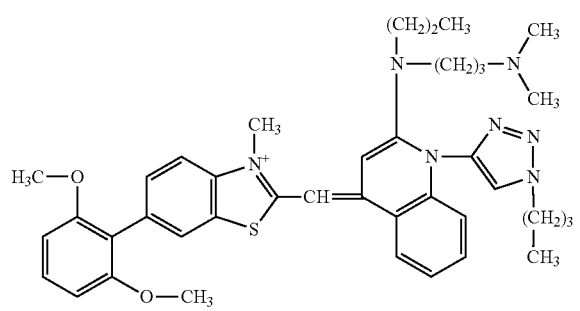

A mixture of 1.7 mg of Compound (34), 1 mg of Cu(I)I, 50 uL of diisopropylethylamine, and about 5 equivalents of propylazide was stirred at room temperature in 1 mL of methanol overnight. Volatile components were removed under reduced pressure, and the crude material was purified using silica gel chromatography with chloroform and methanol.

Example 57

Preparation of Compound (58)

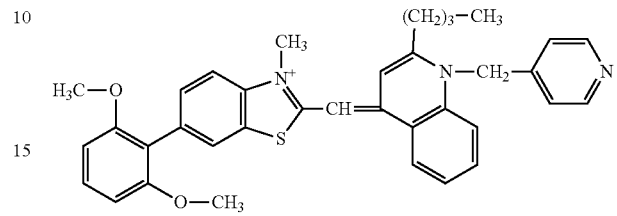

To 0.1 g of Compound (41) in 5 mL of THF at −78° C., 0.32 mL of a 2.5 M n-butyllithium was added and stirred at −78° C. for 1 hour. Next, 0.5 mL of acetic acid was added and stirred at room temperature for 1 hour. Volatile components were evaporated and the residue pumped in vacuo. To the dark residue in several mL of methylene chloride, 243 mg of Compound (5) and 0.2 mL of triethylamine were added and stirred at room temperature for 1 hour. The organic layer was washed with water and brine, and dried over magnesium sulfate. The crude material was purified using silica gel chromatography with ethyl acetate, chloroform and methanol.

Example 58

Preparation of Compound (59)

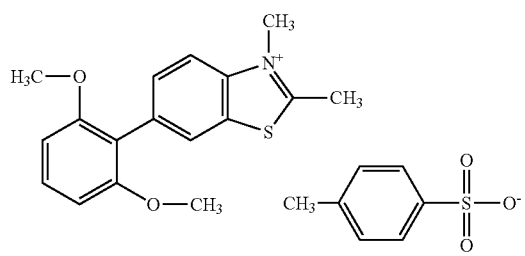

A mixture of 1.26 g of 5-(2,6-dimethoxyphenyl)-2-methylbenzothiazole and 0.99 g of methyl tosylate was heated at 130° C. for 1 hour. The crude material was stirred in about 30 mL of ethyl acetate and filtered to obtain the product.

Example 59

Preparation of Compound (60)

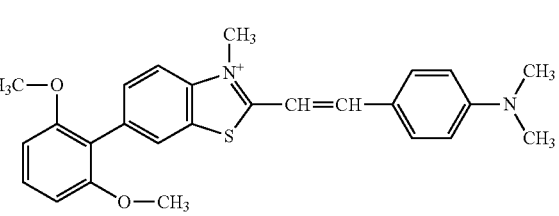

A mixture of 0.1 g of Compound (59), 32 mg of 4-dimethylaminobenzaldehyde and 21 uL of piperidine was heated at 40° C. in 10 mL of ethanol for 1.5 hours. Volatile components were removed under reduced pressure, and the residue was dissolved in chloroform and washed with water and brine. The crude material was purified using silica gel chromatography with chloroform and methanol.

Example 60

Preparation of Compound (61)

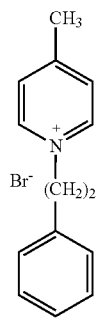

A mixture of 1 g of lepidine and 1 mL of (2-bromoethyl)benzene was heated at 90° C. for 2 hours. About 30 mL of ethyl acetate was added and refluxed for 15 minutes. The product was collected by filtration.

Example 61

Preparation of Compound (62)

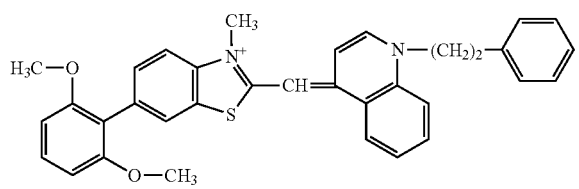

A mixture of 0.1 g of Compound (5), 67 mg of Compound (61), and 86 uL of triethylamine in 10 mL of dichloroethane was stirred at room temperature for 1 hour. Volatile components were evaporated under reduced pressure, and the residue was stirred in about 30 mL of ethyl acetate at room temperature overnight. The product was collected by filtration.

Example 62

Preparation of Compound (63)

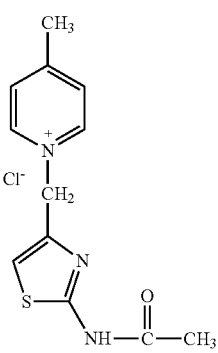

A mixture of 40 uL of lepidine and 57 mg of 2-(acetamido)-4-(chloromethyl)-thiazole was heated at 90° C. for 2 hours. The crude material was stirred in about 20 mL of ethyl acetate for several hours, and filtered to obtain the product.

Example 63

Preparation of Compound (64)

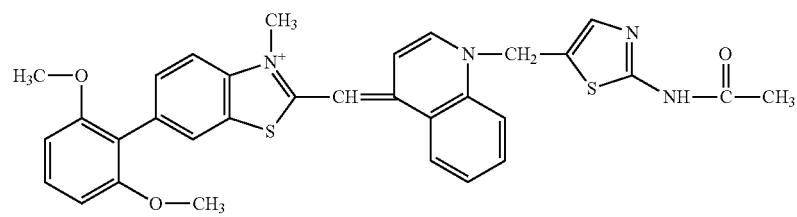 [SMILES: COc1cccc(OC)c1-c1ccc2c(c1)sc(C=C1C=CN(Cc3cnc(NC(C)=O)s3)c3ccccc31)[n+]2C]

A mixture of 0.13 g of Compound (5), 0.26 mmole of Compound (63), and 0.11 mL of triethylamine was stirred in 10 mL of dichloroethane at room temperature for 1 hour. The crude product was purified using silica gel chromatography with chloroform and methanol.

Example 64

Preparation of Compound (65)

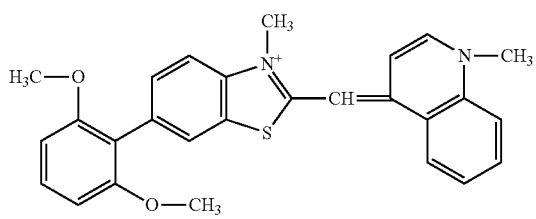

A mixture of 0.1 g of Compound (5), 58 mg of 1,4-dimethylquinolinium iodide, and 86 uL of triethylamine was stirred in 10 mL of dichloroethane at room temperature for 1 hour. Volatile components were evaporated under reduced pressure, and the residue was stirred in about 50 mL of ethyl acetate for 30 minutes. The product was collected by filtration.

Example 65

Preparation of Compound (66)

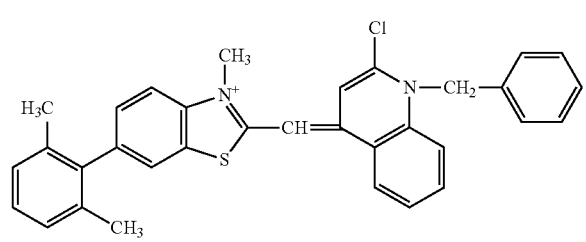 [SMILES: Cc1cccc(C)c1-c1ccc2c(c1)sc(C=C1C=C(Cl)N(Cc3ccccc3)c3ccccc31)[n+]2C]

Compound (66) was prepared by following the same procedure used to prepare Compound (15), using Compounds (7) and (13) as the starting materials.

Example 66

Preparation of Compound (67)

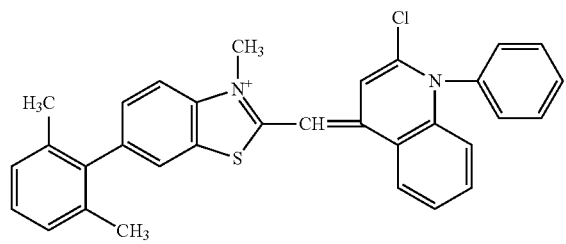 [SMILES: Cc1cccc(C)c1-c1ccc2c(c1)sc(C=C1C=C(Cl)N(c3ccccc3)c3ccccc31)[n+]2C]

Compound (67) was prepared by following the same procedure used to prepare Compound (15), using Compound (7) and 4-methyl-1-phenyl-2(H)-quinolone as the starting materials.

Example 67

Preparation of Compound (68)

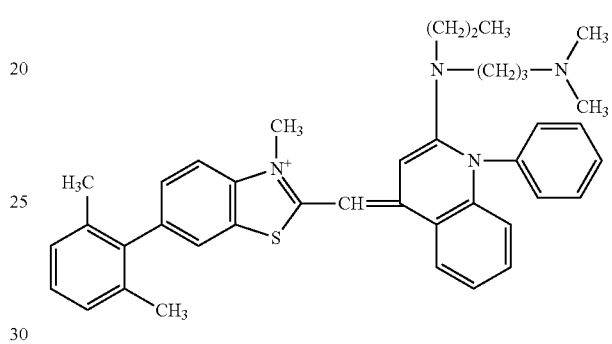

Compound (68) was prepared by following the same procedure used to prepare Compound (16), using Compound (67) and N,N-dimethyl-N'-propyl-propanediamine as the starting materials.

Example 68

Preparation of Compound (69)

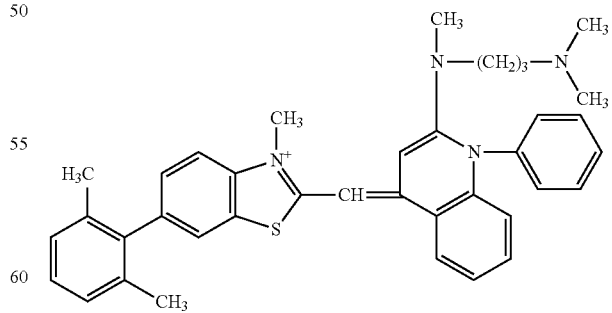

Compound (69) was prepared by following the same procedure used to prepare Compound (16), using Compound (67) and N,N,N'-trimethylpropanediamine as the starting materials.

Example 69

Preparation of Compound (70)

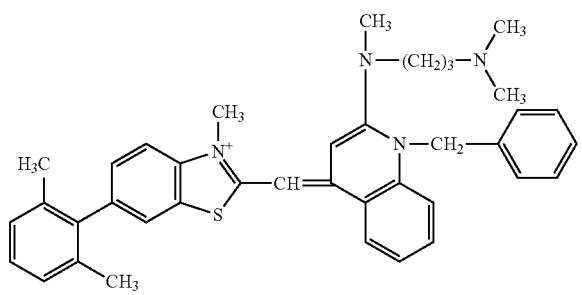

Compound (70) was prepared by following the same procedure used to prepare Compound (16), using Compound (66) and N,N,N'-trimethylpropanediamine as the starting materials.

Example 70

Preparation of Compound (71)

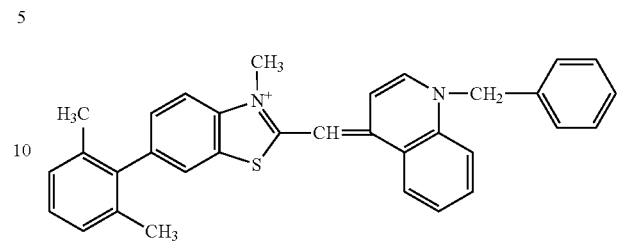

A mixture of 20 mg of Compound (7), 13 mg of 1-benzyl-4-methylquinolinium bromide, and 50 uL of triethylamine was stirred in 1 mL of methanol at room temperature for 1 hour. Volatile components were evaporated under reduced pressure, and the crude material was purified using silica gel column chromatography with chloroform and methanol.

Example 71

Preparation of Compound (72)

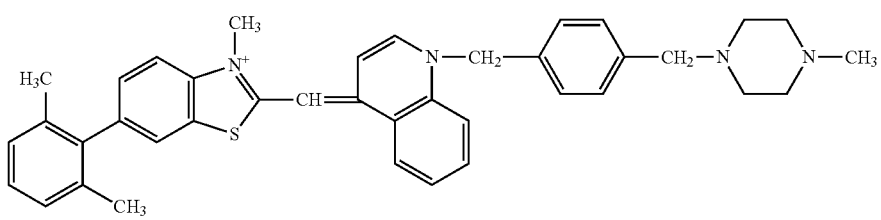 [SMILES: Cc1cccc(C)c1-c1ccc2c(c1)sc(C=C1C=CN(Cc3ccc(CN4CCN(C)CC4)cc3)c3ccccc31)[n+]2C]

A mixture of 20 mg of Compound (7), 17 mg of Compound (42), and 50 uL of triethylamine was stirred at room temperature in 1 mL of DMF for 1 hour. This was followed by the addition of about 100 uL of 1-methylpiperazine, and the mixture was stirred overnight. Volatile components were evaporated under reduced pressure, and the product was purified using silica gel chromatography with chloroform and methanol.

Example 72

Preparation of Compound (73)

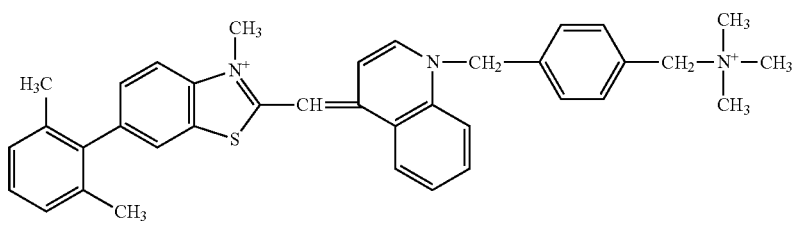 [SMILES: Cc1cccc(C)c1-c1ccc2c(c1)sc(C=C1C=CN(Cc3ccc(C[N+](C)(C)C)cc3)c3ccccc31)[n+]2C]

A mixture of 8 mg of Compound (7), 8 mg of Compound (42) and 0.5 mL of trimethylamine (25% in methanol) was stirred at room temperature in 1 mL of DMF for 4 hours. Volatile components were evaporated under reduced pressure, and then pumped in vacuo. The crude material was purified using silica gel chromatography with chloroform and methanol.

Example 73

Preparation of Compound (74)

A mixture of 20 mg of Compound (7), 5 equivalents of Compound (54), and 50 uL of triethylamine was stirred in 1 mL of DMF at room temperature for 1 hour. Volatile components were evaporated under reduced pressure. The crude material was purified using silica gel column chromatography with chloroform and methanol.

Example 74

Preparation of Compound (75)

A mixture of about 3 mg of Compound (74) and 0.2 mL of iodomethane was stirred at room temperature overnight in 1 mL of DMF. The product was precipitated by addition of 4 mL of ethyl acetate.

Example 75

Preparation of Compound (76)

Compound (76) was prepared by following the same procedure used to prepare Compound (15), using Compound (6) and 4-methyl-1-phenyl-2(H)-quinolone as the starting materials.

Example 76

Preparation of Compound (77)

Compound (77) was prepared by following the same procedure used to prepare Compound (16), using Compound (15) and N,N-dimethyl-N'-propylpropanediamine.

Example 77

Preparation of Compound (78)

A mixture of about 35 mg of Compound (6), 30 mg of Compound (42), and 17 uL of diisopropylethylamine was stirred in 5 mL of a 1:4 v/v DMF/methylene chloride solvent at room temperature overnight. Volatile components were evaporated under reduced pressure, and the crude product was purified using silica gel column chromatography with ethyl acetate, chloroform and methanol.

Example 78

Preparation of Compound (79)

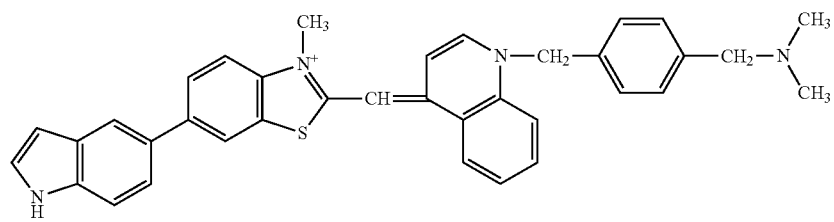 [SMILES: CN(C)Cc1ccc(CN2C=CC(=Cc3sc4cc(-c5ccc6[nH]ccc6c5)ccc4[n+]3C)c3ccccc32)cc1]

A mixture of about 5 mg of Compound (78) and 3 mL of a 2 M solution of dimethylamine in THF was heated in 10 mL of methanol at room temperature for 3 days. Volatile components were removed under reduced pressure, and the crude product was purified using silica gel column chromatography with chloroform, methanol and triethylamine.

Example 79

Preparation of Compound (80)

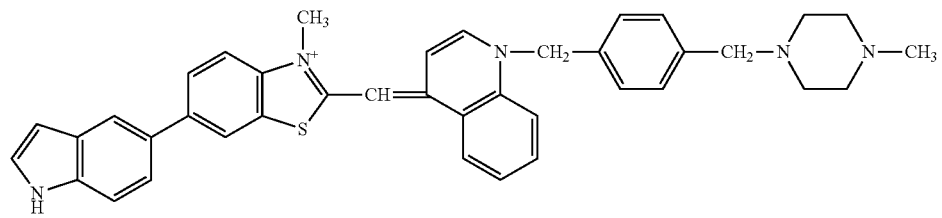 [SMILES: CN1CCN(Cc2ccc(CN3C=CC(=Cc4sc5cc(-c6ccc7[nH]ccc7c6)ccc5[n+]4C)c4ccccc43)cc2)CC1]

A mixture of about 5 mg of Compound (78) and 30 mg of 1-methylpiperazine was stirred at 35° C. for 4 days. Volatile components were evaporated under reduced pressure, and the product was purified on a preparatory TLC plate.

Example 80

Preparation of Compound (81)

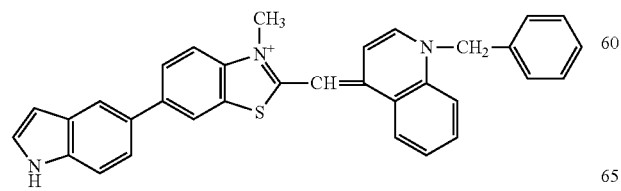

A mixture of 20 mg of Compound (6), 20 mg of 1-benzyl-4-methylquinolinium bromide, and 0.1 mL triethylamine was stirred in 0.5 mL of methylene chloride at room temperature for 1 hour. Volatile components were evaporated under reduced pressure, and the crude material was purified using silica gel column chromatography with methanol and chloroform.

Example 81

Preparation of Compound (82)

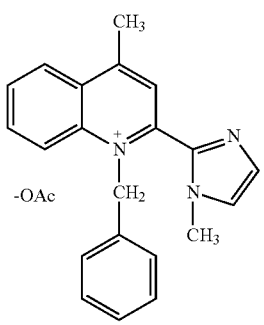

To 1.3 g of 1-methylimidazole in 20 mL of THF at −78° C. under nitrogen, 2.8 mL of a 2.5 M n-butyllithium was introduced. After 45 minutes at the low temperature, 1.25 g of 1-benzyl-4-methyl-2(H)-quinolone (in 10 mL of THF) was added and the resulting mixture was further stirred at −78° C. for 1 hour, at 0° C. for 2 hours and room temperature for another 30 minutes. Acetic acid (0.5 mL) was added and stirred for 30 minutes. Volatile components were removed under reduced pressure. The resulting material was presumably 1-benzyl-4-methyl-2-(1-methylimidazoyl)-quinolinium acetate.

Example 82

Preparation of Compound (83)

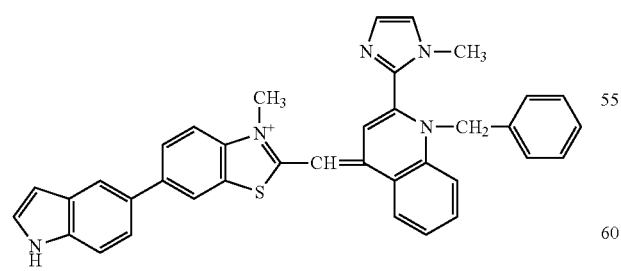

To a mixture of 20 mg of Compound (6) and 0.01 mmole of Compound (82) in 1 mL of methanol, 50 uL of triethylamine was added and stirred at room temperature for 1 hour. Volatile components were evaporated. The crude material was purified using silica gel column chromatography with chloroform and methanol, and then on a LH-20 column with water to obtain the pure product.

Example 83

Preparation of Compound (84)

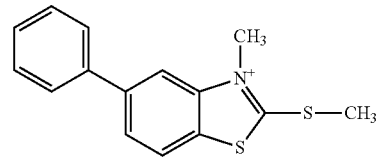 [SMILES: CSc1sc2ccc(-c3ccccc3)cc2[n+]1C]

The compound was prepared from the commercially available 5-phenyl-2-mercapto-benzothiazole (Aldrich Chemical; St. Louis, Mo.) by first converting the mercapto into a methylthio with potassium carbonate and methyl tosylate, and further quarternization of the benzothiazole under neat condition with methyl tosylate to generate the desired compound.

Example 84

Preparation of Compound (85)

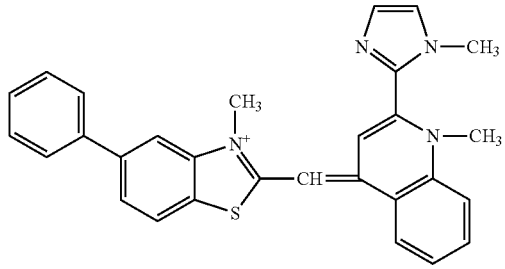 [SMILES: CN1C(c2nccn2C)=CC(=Cc2sc3ccc(-c4ccccc4)cc3[n+]2C)c2ccccc21]

A mixture of 60 mg of Compound (84), one molar equivalent of 1,4-dimethyl-2-(1-methylimidazoyl)-quinolinium acetate (prepared by similar protocol to that of Compound (82) using 1,4-dimethyl-2(H)-quinolone as the starting material), and 0.1 mL of triethylamine was stirred in 1 mL of methanol at room temperature for 1 hour. The crude material was purified on a LH-20 column eluting with water.

Example 85

Preparation of Compound (86)

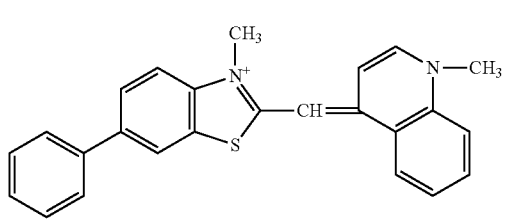 [SMILES: CN1C=CC(=Cc2sc3cc(-c4ccccc4)ccc3[n+]2C)c2ccccc21]

A mixture of 15 mg of Compound (10) and 9.6 mg of 1,4-dimethylquinolinium iodide in 1 mL of methylene chloride was stirred at room temperature for 1 hour. The product was obtained by filtration.

Example 86

Preparation of Compound (87)

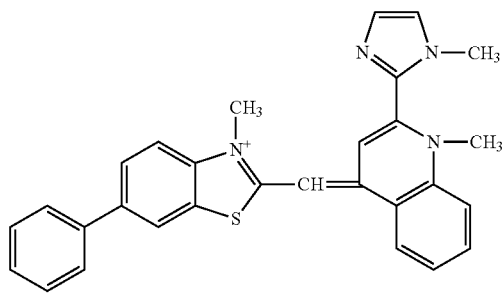 [SMILES: CN1C(c2nccn2C)=CC(=Cc2sc3cc(-c4ccccc4)ccc3[n+]2C)c2ccccc21]

A mixture of 27 mg of Compound (10), 0.067 mmole of 1,4-dimethyl-2-(1-methylimidazoyl)-quinolinium acetate (prepared by similar protocol to that of Compound (82) using 1,4-dimethyl-2(H)-quinolone as the starting material), and 0.1 mL of triethylamine was stirred in 1 mL of methylene chloride for 1 hour. Volatile components were evaporated, and the crude product was purified on a LH-20 column.

Example 87

Preparation of Compound (88)

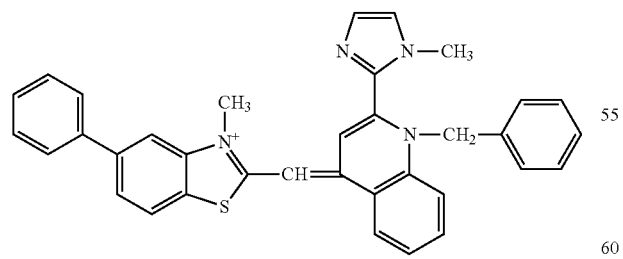

To a mixture of 8 mg of Compound (84) and one equivalent of Compound (82) in 1 mL of methanol, 50 uL of triethylamine was added and stirred at room temperature for 1 hour. Volatile components were evaporated, and the crude material was purified first by silica gel column chromatography with chloroform and methanol and second on a LH-20 column with water to obtain the pure product.

Example 88

Preparation of Compound (89)

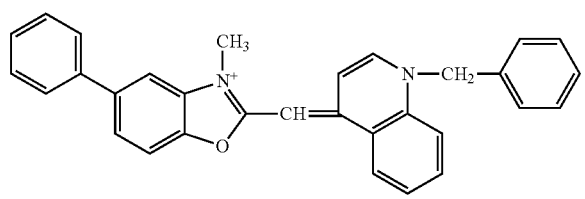 [SMILES: C[n+]1c(C=C2C=CN(Cc3ccccc3)c3ccccc32)oc2ccc(-c3ccccc3)cc21]

A mixture of 43 mg of 5-phenyl-3-methyl-2-methylthiobenzoxazolium tosylate, 39 mg of 1-benzyl-4-methylquinolinium bromide, and 0.1 mL of triethylamine was stirred in 1 mL of methylene chloride for 1 hour. The product was collected by filtration.

Example 89

Preparation of Compound (90)

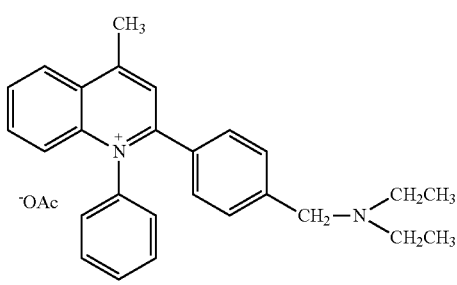

To 0.36 g of 4-diethylaminomethyl-bromobenzene in 4 mL dry THF at −78° C. under nitrogen, 0.48 mL of a 2.5 M n-butyllithium was introduced followed by 0.235 g of 4-methyl-1-phenyl-2(H)-quinolone (in 10 mL THF). The reaction was stirred at the low temperature for 1 hour before the addition of 1 mL acetic acid. The mixture was stirred at room temperature for another hour, and the solvent was removed and the residue was further pumped for an hour. The crude product 2-(4-diethylaminomethyl)-4-methyl-1-phenylquinolinium acetate was used without further purification.

Example 90

Preparation of Compound (91)

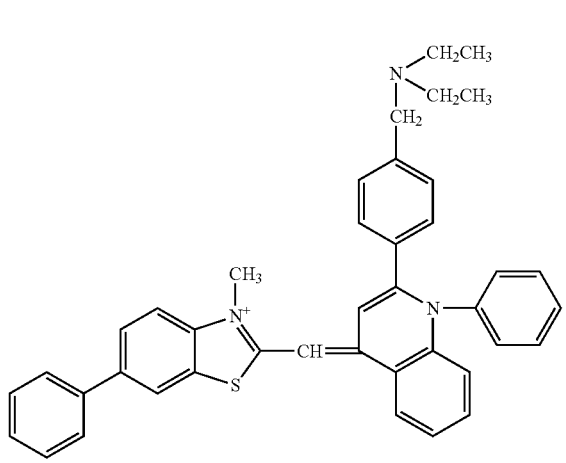 [SMILES: CCN(CC)Cc1ccc(C2=CC(=Cc3sc4cc(-c5ccccc5)ccc4[n+]3C)c3ccccc3N2c2ccccc2)cc1]

A mixture of 20 mg of Compound (10), one equivalent of Compound (90), and 50 uL of triethylamine was stirred in 1 mL of methylene chloride at room temperature for 1 hour. Volatile components were removed, and the crude material was purified using silica gel column chromatography with chloroform and methanol.

Example 91

Preparation of Compound (92)

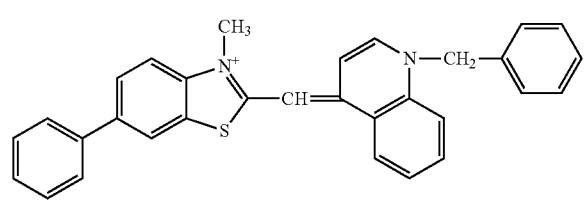 [SMILES: C[n+]1c(C=C2C=CN(Cc3ccccc3)c3ccccc32)sc2cc(-c3ccccc3)ccc21]

A mixture of 12 mg of Compound (10), 10 mg of 1-benzyl-4-methylpyridinium bromide, and 0.1 mL of triethylamine in 1 mL of methylene chloride was refluxed for two hours. Volatile components were removed under reduced pressure, and the crude material was stirred in about 2 mL of methylene chloride for 1 hour. The product was collected by filtration.

Example 92

Preparation of Compound (93)

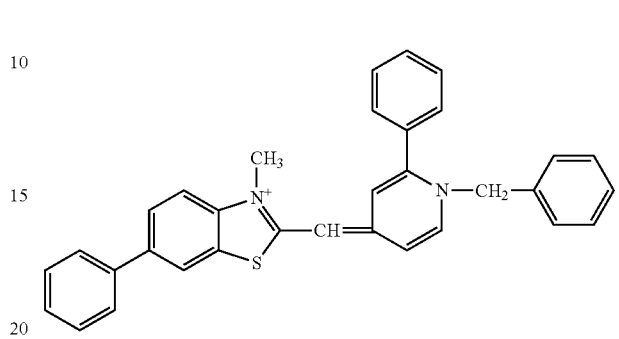

A mixture of 8 mg of Compound (10), 8.8 mg of 1-benzyl-4-methyl-2-phenylquinolinium bromide, and 50 uL of triethylamine was refluxed in 2 mL of methylene chloride for 3 hours. The crude material was purified using silica gel chromatography with chloroform and methanol.

Example 93

Preparation of Compound (94)

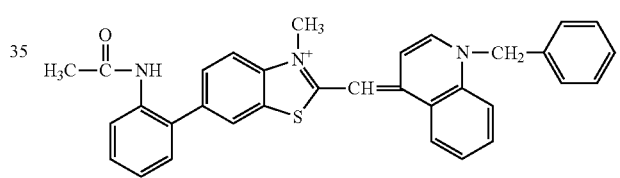

A mixture of 22 mg of Compound (12), 10 mg of 1-benzyl-4-methylquinolinium bromide, and 50 uL of triethylamine was stirred in 1 mL of methanol at room temperature for one hour. The crude material was purified using silica gel chromatography with chloroform and methanol.

Example 94

Preparation of Compound (95)

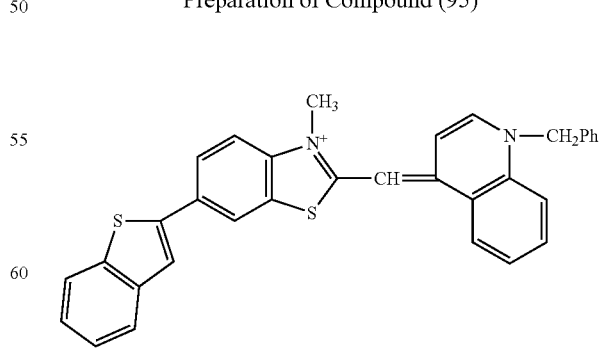

A mixture of 6.5 mg of Compound (9), 4 mg of 1-benzyl-4-methylquinolinium bromide, and 50 uL of triethylamine was stirred in 1 mL of methanol at room temperature for 3

Example 95

Preparation of Compound (96)

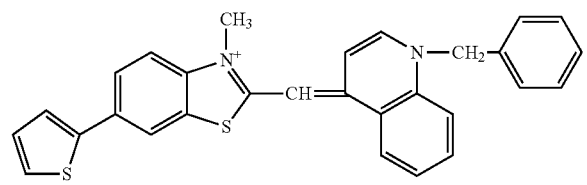 [SMILES: C[n+]1c(C=C2C=CN(Cc3ccccc3)c3ccccc32)sc2cc(-c3cccs3)ccc21]

A mixture of 6.8 mg of Compound (11), 4.7 mg of 1-benzyl-4-methylquinolinium bromide, and 50 uL of triethylamine was stirred in 1 mL of methylene chloride at room temperature for 1 hour. The crude material was purified using silica gel column chromatography with chloroform and methanol.

Example 96

Preparation of Compound (97)

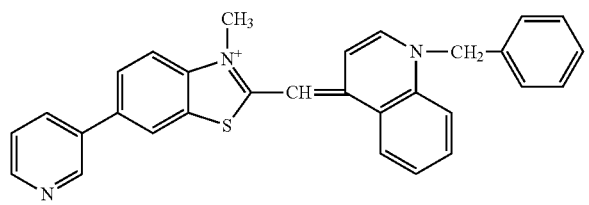 [SMILES: C[n+]1c(C=C2C=CN(Cc3ccccc3)c3ccccc32)sc2cc(-c3cccnc3)ccc21]

A mixture of 18 mg of 3-methyl-6-pyridyl-1,3-benzothiazole-2-thione, 22 mg of 1-benzyl-4-methylquinolinium bromide, 14 mg of methyl tosylate, and 0.1 mL of diisopropylethylamine was heated at 100° C. for 30 minutes. Volatile components were removed under reduced pressure, and the crude product was purified by preparative TLC plate.

Example 97

Preparation of Compound (98)

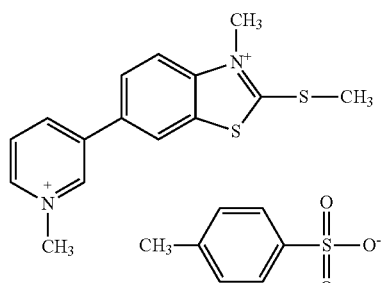

A mixture of 23 mg of 3-methyl-6-pyridyl-1,3-benzolthiazole-2-thione and 330 mg of methyl tosylate was heated at 130° C. for 1 hour. Next, 10 mL of ethyl acetate was added and refluxed for 15 minutes. The product was collected by filtration.

Example 98

Preparation of Compound (99)

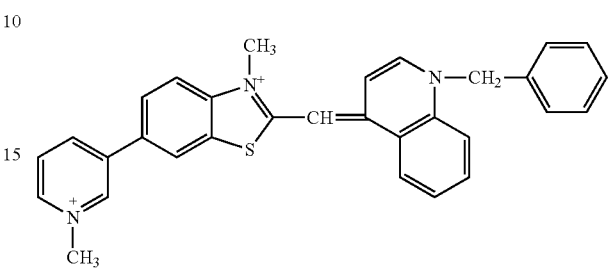

A mixture of 27 mg of 1-benzyl-4-methylquinolinium bromide, one equivalent of Compound (98), and 0.2 mL of triethylamine was stirred in 2 mL of DMF at room temperature. The product was collected by filtration.

Example 99

Preparation of Compound (100)

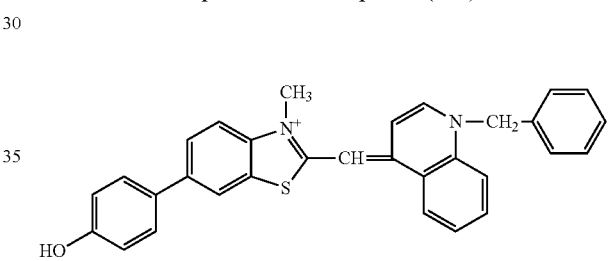

A mixture of 50 mg of Compound (8), 1.2 equivalent of 1-benzyl-4-methylquinolinium bromide, and 45 uL of triethylamine was stirred in a mixed solvent of dichloroethane/DMF (v/v, 1:1, 4 mL) at room temperature for 3 hours. The reaction mixture was diluted with chloroform, washed with water, and dried over magnesium sulfate. The product precipitated out from the chloroform later as the volume was reduced.

Example 100

Preparation of Compound (101)

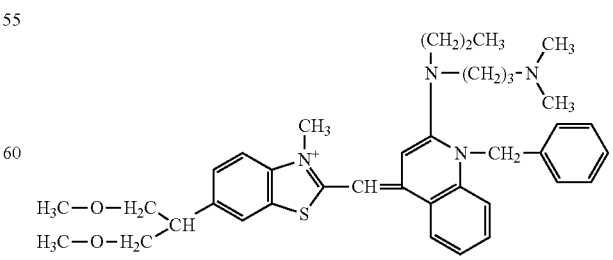

Compound (101) was prepared by following the same procedure used to prepare Compound (16), using 6-(bis-(1,3- dimethoxy)-prop-2-yl)-3-methyl-2-methylthio-benzothiazolium tosylate and Compound (13) as the starting materials.

Example 101

Preparation of Compound (102)

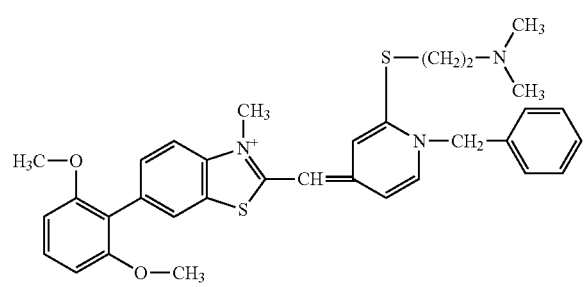

Compound (102) was prepared by following the same procedure used to prepare Compound (24), using Compound (5) and 1-benzyl-4-methyl-pyridin-2-one as the starting materials.

Example 102

Preparation of Compound (103)

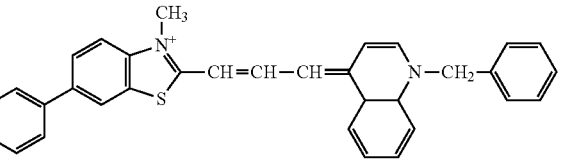

Acetic anhydride (0.1 mL) was added to a mixture of 0.127 mg of 2-(2-anilinovinyl)-3-methyl-6-phenylquinolinium tosylate, one equivalent of 1-benzyl-4-methylquinolinium bromide, and 40 uL of triethylamine in 2 mL of dichloroethane at room temperature. The mixture was stirred for 2 hours. The reaction was diluted with chloroform and washed with water and brine. The crude material was purified by recrystallizing from methanol and ethyl acetate.

Example 103

Preparation of Compound (104)

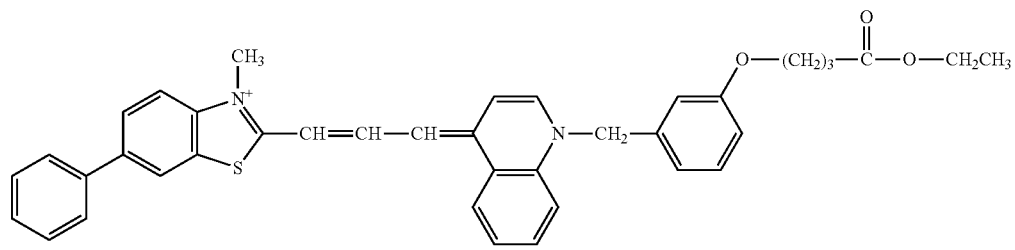

Acetic anhydride (90 uL) was added to a mixture of 0.107 mg of 2-(2-anilinovinyl)-3-methyl-6-phenylquinolinium tosylate, one equivalent of 1-((3-ethoxycarbonyl-1-propoxy)phenylmethyl)-4-methylquinolinium chloride, and 40 uL of triethylamine in 5 mL of dichloroethane at room temperature. The mixture was stirred for 2 hours. The reaction mixture was diluted with chloroform and washed with water and brine. The crude material was purified using silica gel column chromatography with chloroform and methanol.

Example 104

Preparation of Compound (105)

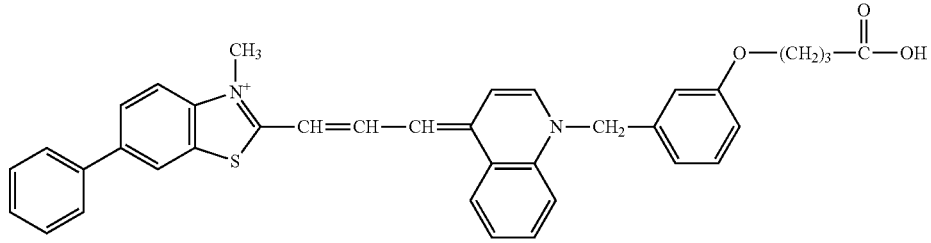

Water (0.5 mL) and 40 uL of 10% sodium hydroxide was added to 59 mg of Compound (107) in 5 mL of methanol. The mixture was stirred at room temperature for several hours. The reaction was diluted with about 30 mL of water, acidified with 1 N HCl, and filtered to recover the product.

Example 105

Preparation of Compound (106)

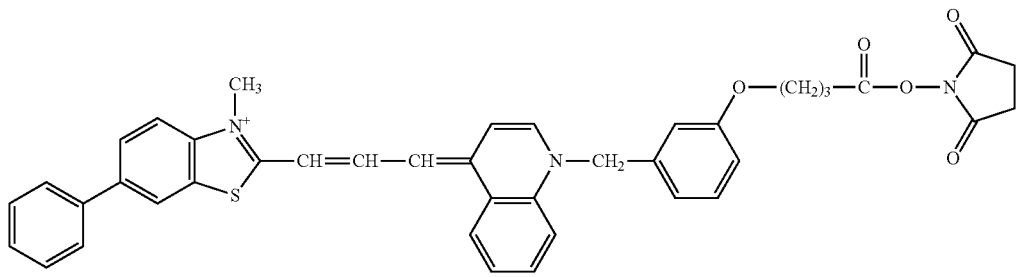

O—(N-succinimidyl)-N,N,N',N'-tetramethyluronium tetrafluoroborate (8.2 mg) was added to 11.3 mg of Compound (105) in 2 mL of DMF and 8 uL of triethylamine in 2 mL of DMF. The mixture was stirred overnight at room temperature. About 6 mL of ethyl acetate was added to precipitate the product, and the product was obtained by filtration.

Example 106

Preparation of Compound (107)

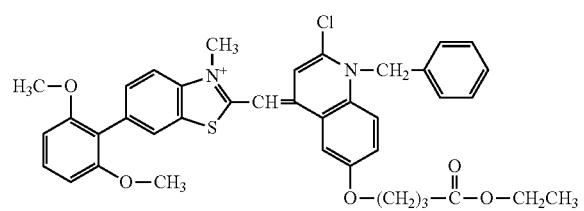

Compound (107) was prepared by following the same procedure used to prepare Compound (15), using Compound (5) and 1-benzyl-6-(3-ethoxycarbonyl-1-propoxy)-4-methyl-2 (H)-quinolone as the starting materials.

Example 107

Preparation of Compound (108)

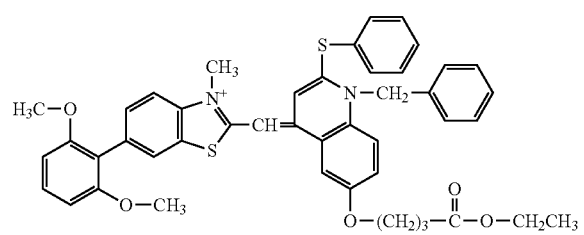

A mixture of 0.314 g of Compound (107), 0.13 mL of thiophenol, and 0.3 mL of triethylamine was stirred in 5 mL of dichloroethane at 60° C. for several hours. The product was purified using silica gel column chromatography with chloroform and methane.

Example 108

Preparation of Compound (109)

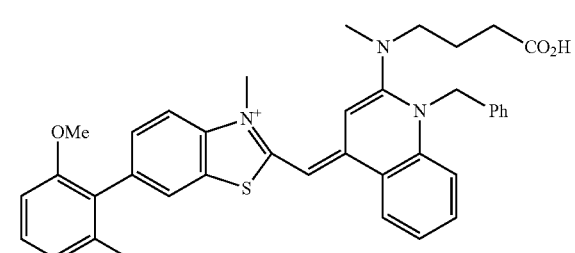

4-N-methylaminobutyric acid (39 mg) and 107 uL of triethylamine was dissolved in a mixture of 1.5 mL of isopropyl alcohol and several drops of water. This mixture was added to a solution of 30 mg of Compound (15) in 3 mL of dichloroethane and the resulting mixture was heated at 60° C. for 1 hour. The crude material was diluted with additional chloroform and washed with diluted aqueous HCl. The product was purified on a silica gel column with chloroform and methanol.

Example 109

Preparation of Compound (110)

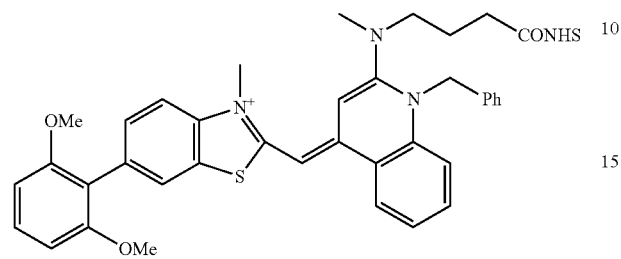

O—(N-succinimidyl)-N,N,N',N'-tetramethyluronium tetrafluoroborate (7.4 mg) was added to a mixture of 11 mg of B36-13-LY and 5 uL of triethylamine in 2 mL of DMF. After 30 minutes stirring at room temperature, the crude material was purified on a silica gel column eluting with chloroform and acetone.

Example 110

Preparation of Compound (111)

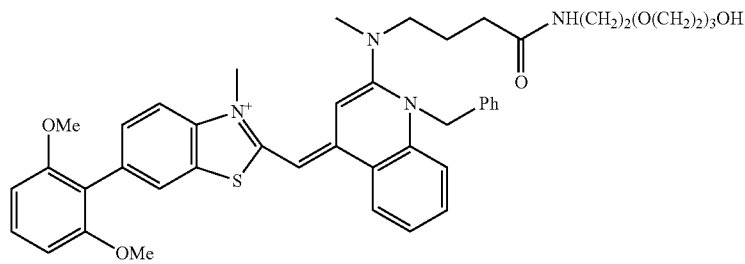

Amino-dPEG4-alcohol (3.0 mg; Quanta Biodesign, Ltd.; Powell, Ohio) was added to a mixture of about 5 mg of Compound (110) and 2 equivalents of triethylamine. The mixture was stirred for 30 minutes. The mixture was concentrated and several mL of ethyl acetate was added and stirred briefly and filtered to obtain the product.

Example 111

Preparation of Compound (112)

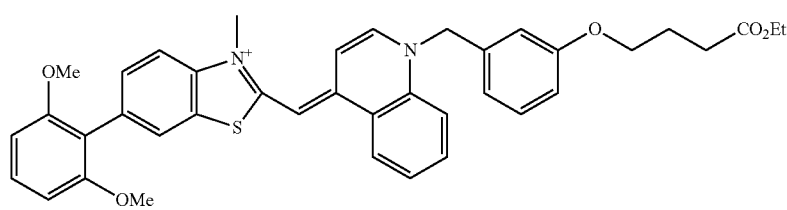 [SMILES: CCOC(=O)CCCOc1cccc(CN2C=C/C(=C\c3sc4cc(-c5c(OC)cccc5OC)ccc4[n+]3C)c3ccccc32)c1]

Triethylamine (61 uL) was added to a mixture of 59 mg of 1-((3-ethoxycarbonyl-1-propoxy)phenylmethyl)-4-methylquinolinium chloride and 74 mg of Compound (5) in 3 mL of methylene chloride. The mixture was stirred for 5 minutes. The mixture was then diluted with chloroform and washed with 1:1 mixture of water/brine to yield the product.

Example 112

Method for Determination of DNA/RNA Fluorescence Ratios

The tested compound was dissolved as a stock solution in DMSO at a concentration of about 0.1-1.0 mg/mL. The exact concentration is not critical. Three tubes are prepared, each containing the same 1-20 uL of stock solution. The first tube contained 10 mM Tris, 1 mM EDTA (pH 7.5) buffer; the second tube contained buffer and 65 ug/mL calf thymus double stranded DNA; and the third tube contained buffer and 65 ug/mL ribosomal RNA. The tubes were incubated at room temperature for 10-15 minutes with protection from light.

Fluorescence scans of the three solutions were performed in disposable cuvettes, with the excitation wavelength corresponding to the absorption maximum for the compound bound to DNA (or RNA if the values were significantly different). In some cases, it was necessary to dilute the sample to keep the fluorescence signal on-scale. In these cases, all three samples were diluted to the same degree. The ratio of the fluorescence of the compound in the presence of DNA and RNA was determined.

Example 113

DNA/RNA Fluorescence Ratios for Prepared Compounds

The following compounds were selected as representative of the inventive class of compounds. The fluorescence values in the presence of DNA and RNA were determined as described in the previous Example. The following table shows the DNA/RNA fluorescence ratios, where higher values indicate a selectivity for DNA. A ratio of 1 would indicate no selectivity. Excitation and emission values are in nm.

| Compound | ex/em | DNA/RNA (fluorescence ratio) |
|---|---|---|
| Thiazole orange | 510/530 | 1 |
| Compound 16 | 504/532 | 15.2 |
| Compound 17 | 508/536 | 4.8 |
| Compound 18 | 505/533 | 3.5 |
| Compound 19 | 525/553 | 7.3 |
| Compound 20 | 510/536 | 4 |
| Compound 21 | 510/534 | 5.4 |
| Compound 22 | 505/534 | 4.7 |
| Compound 23 | 500/529 | 3.8 |
| Compound 24 | 520/570 | 4.6 |
| Compound 25 | 518/559 | 9 |
| Compound 26 | 505/541 | 36 |
| Compound 28 | 497/527 | 6.5 |
| Compound 30 | 495/527 | 5.7 |
| Compound 31 | 505/534 | 10.5 |
| Compound 32 | 498/517 | 36 |
| Compound 34 | 503/532 | 5.8 |
| Compound 38 | 497522 | 13 |
| Compound 39 | 507/536 | 6.1 |
| Compound 44 | 510/540 | 22 |
| Compound 45 | 511/541 | 13.2 |
| Compound 46 | 512/542 | 11.5 |
| Compound 47 | 512/541 | 8.6 |
| Compound 48 | 513/540 | 7.3 |
| Compound 49 | 520/542 | 18 |
| Compound 50 | 512/541 | 9.7 |
| Compound 53 | 510/540 | 60 |
| Compound 55 | 513/541 | 10.9 |
| Compound 56 | 515/545 | 3.7 |
| Compound 57 | 506/536 | 3.8 |
| Compound 62 | 510/539 | 48 |
| Compound 65 | 506-536 | 11.3 |
| Compound 68 | 498/523 | 7 |
| Compound 69 | 494/523 | 3.2 |
| Compound 70 | 501/524 | 2.7 |
| Compound 89 | 485/512 | 1.8 |
| Compound 91 | 522/563 | 1.5 |
| Compound 92 | 458/501 | 1 |
| Compound 93 | 466/514 | 1.5 |
| Compound 94 | 513/530 | 2.1 |
| Compound 95 | 550/591 | 1.9 |
| Compound 96 | 527/555 | 8 |
| Compound 97 | 513/538 | 3.7 |
| Compound 99 | 511/534 | 1.3 |
| Compound 100 | 513/551 | 8.1 |
| Compound 101 | 503/527 | 3 |
| Compound 102 | 475/515 | 3.3 |
| Compound 103 | 507/537 | 3.1 |
| Compound 104 | 652/666 | 9 |
| Compound 109 | 496/525 | 121 |
| Compound 111 | 497/527 | 64 |
| Compound 112 | 500/541 | 191 |

Example 114

Evaluation of Compound (24)

This compound has a 520 nm excitation maximum, and can effectively be excited with either a 488 nm line (blue laser) or a 532 nm (green laser) line. The compound has an emission maximum of 569 nm (orange).

Example 115

Use of Compound (20) in Flow Cytometry

Live Jurkat cells (human T-lymphocyte) were suspended at $1 \times 10^6$ cells/ml in RPMI media with 10% Fetal Bovine Serum (FBS). 5 µM Compound (20) was added to one mL cell suspension, and incubated at 37° C. for 60 minutes protected from light. Cells were processed using a Becton Dickinson (BD) LSRII Flow Cytometer. A Forward Scatter (FS) vs Side Scatter (SS) dual parameter plot was used to gate main cell population. On gated cells, a dual-parameter plot of Fluorescence-Width vs Fluorescence-Area was used for single cell discrimination gating. Single color fluorescence was collected at 530/30 bandpass using the 488 nm excitation laser, collecting 30,000 events at flow rate of about 200 events/second. The data was further analyzed using ModFit LT Flow Cytometry Modeling Software from Verity Software House, Inc. to determine the ratio of G2/G1 and the CV of G1 phase.

Typical cell cycle histograms were demonstrated showing G0G1 phase, S phase, and G2M phase. This was obtained on the live cell gate. Further analysis using ModFit Software showed that G1-phase is 47.08% with peak CV of 6.92%, S-phase is 46.67%, G2-phase is 6.25% and the G2/G1 ratio is 1.83. This demonstrated that the compound stains live cells for cell cycle where the CV of G1-phase<8%, and the observed ratio indicated linearity of staining.

Example 116

Use of Compound (24) in Flow Cytometry

Live Jurkat cells were treated with colcemid for 2 hours, to arrest cell cycle at mitosis, thus resulting in a larger more defined G2M-phase. The cells were suspended at $1 \times 10^6$ cells/ml in RPMI media with 10% Fetal Bovine Serum (FBS). 10 µM Compound (24) was added to one mL cell suspension, incubated at 37° C. for 30 minutes protected from light. Cells were processed using the Becton Dickinson (BD) LSRII Flow Cytometer. Forward Scatter (FS) vs Side Scatter (SS) dual parameter plot was used to gate main cell population. On gated cells, a dual-parameter plot of Fluorescence-Width vs Fluorescence-Area was used for single cell discrimination gating. Single color fluorescence was collected at 585/42 bandpass using the 488 nm excitation laser, and also collected at the same 585/42 bandpass using the 532 nm excitation laser, collecting 30,000 events at flow rate of about 200 events/second. The data was further analyzed using ModFit LT Flow Cytometry Modeling Software from Verity Software House, Inc. to determine the ratio of G2/G1 and the CV of G1 phase.

Typical cell cycle histograms were demonstrated showing G0G1 phase, S phase, and G2M phase. This was obtained on the live cell gate. Further analysis using ModFit Software showed typical cell cycle staining. This demonstrated that the compound stains live cells for cell cycle where the CV of G1-phase<8%, and the observed ratio indicated linearity of staining.

Example 117

Use of Compound (20) in Flow Cytometry

Live HL60 cells (human promyeloblasts) were suspended at $1 \times 10^6$ cells/ml in Iscove's Dulbecco's complete Media with 20% Fetal Bovine Serum (FBS). 5 µM Compound (20) is added to one mL cell suspension, and incubated at 37° C. for 30 minutes protected from light. Cells were processed using the Becton Dickinson (BD) LSRII Flow Cytometer. Forward Scatter (FS) vs Side Scatter (SS) dual parameter plot was used to gate main cell population. On gated cells, a dual-parameter plot of Fluorescence-Width vs Fluorescence-Area was used for single cell discrimination gating. Single color fluorescence was collected at 530/30 bandpass using the 488 nm excitation laser, collecting 30,000 events at flow rate of about 200 events/second. The data was further analyzed using ModFit LT Flow Cytometry Modeling Software from Verity Software House, Inc. to determine the ratio of G2/G1 and the CV of G1 phase.

Typical cell cycle histograms were demonstrated showing G0G1 phase, S phase, and G2M phase. This was obtained on the live cell gate. Further analysis using ModFit Software showed typical cell cycle staining. This demonstrated that the compound stained live cells for cell cycle where the CV of G1-phase<8%, and the observed ratio indicated linearity of staining.

Example 118

Use of Compound (24) in Flow Cytometry

HL60 cells were suspended at $1\times10^6$ cells/ml in Hanks Balanced Salt Solution (HBSS). 10 µM Compound (24) was added to one mL cell suspension, and incubated at room temperature for 30 minutes protected from light. Cells were processed using the Becton Dickinson (BD) LSRII Flow Cytometer. Forward Scatter (FS) vs Side Scatter (SS) dual parameter plot was used to gate main cell population. On gated cells, a dual-parameter plot of Fluorescence-Width vs Fluorescence-Area was used for single cell discrimination gating. Single color fluorescence was collected at 585/42 bandpass using the 488 nm excitation laser, and also at the same 585/42 bandpass using the 532 nm excitation laser, collecting 30,000 events at flow rate of about 200 events/second. The data was further analyzed using ModFit LT Flow Cytometry Modeling Software from Verity Software House, Inc. to determine the ratio of G2/G1 and the CV of G1 phase.

Typical cell cycle histograms were demonstrated showing G0G1 phase, S phase, and G2M phase. This was obtained on the live cell gate. Further analysis using ModFit Software showed typical cell cycle staining. This demonstrated that the compound stained live cells for cell cycle where the CV of G1-phase<8%, and the observed ratio indicated linearity of staining.

Example 119

Use of Compound (24) in Flow Cytometry with Fixed Cells

HL60 cells were fixed with 70% ethanol and stored at −20° C. until use. The fixed cells were washed once in Hanks Balanced Salt Solution (HBSS) and were then suspended at $1\times10^6$ cells/ml in HBSS. 5 µM Compound (24) was added to one mL cell suspension, and incubated at 37° C. for 5 minutes protected from light. Cells were processed using the Becton Dickinson (BD) LSRII Flow Cytometer. Forward Scatter (FS) vs Side Scatter (SS) dual parameter plot was used to gate main cell population. On gated cells, a dual-parameter plot of Fluorescence-Width vs Fluorescence-Area was used for single cell discrimination gating. Single color fluorescence was collected at 585/42 bandpass using the 488 nm excitation laser, and also collected at the same 585/42 bandpass using the 532 nm excitation laser, collecting 30,000 events at flow rate of about 200 events/second. The data was further analyzed using ModFit LT Flow Cytometry Modeling Software from Verity Software House, Inc. to determine the ratio of G2/G1 and the CV of G1 phase.

Typical cell cycle histograms were demonstrated showing G0G1 phase, S phase, and G2M phase. Further analysis using ModFit Software showed typical cell cycle staining. This demonstrated that the compound stained live cells for cell cycle where the CV of G1-phase<8%, and the observed ratio indicated linearity of staining.

Example 120

Use of Compound (20) for Flow Cytometry with Fixed Cells

Live Jurkat cells were treated with colcemid for 2 hours, to arrest cell cycle at mitosis, thus resulting in a larger more defined G2M-phase. The cells were fixed with 70% ethanol and stored at −20° C. until use. The fixed cells were washed once in Hanks Balanced Salt Solution (HBSS) and were then suspended at $1\times10^6$ cells/ml in HBSS. 5 µM Compound (20) was added to one mL cell suspension, and incubated at 37° C. for 5 minutes protected from light. Cells were processed using the Becton Dickinson (BD) LSRII Flow Cytometer. Forward Scatter (FS) vs Side Scatter (SS) dual parameter plot was used to gate main cell population. On gated cells, a dual-parameter plot of Fluorescence-Width vs Fluorescence-Area was used for single cell discrimination gating. Single color fluorescence was collected at 530/30 bandpass using the 488 nm excitation laser, collecting 30,000 events at flow rate of about 200 events/second. The data was further analyzed using ModFit LT Flow Cytometry Modeling Software from Verity Software House, Inc. to determine the ratio of G2/G1 and the CV of G1 phase.

Typical cell cycle histograms were demonstrated showing G0G1 phase, S phase, and G2M phase. Further analysis using ModFit Software showed typical cell cycle staining. This demonstrated that the compound stained live cells for cell cycle where the CV of G1-phase<8%, and the observed ratio indicated linearity of staining.

Example 121

Use of Compound (24) for Flow Cytometry with Induced Apoptosis Cells

Live Jurkat cells were split into 13 samples and each cell split was suspended in complete RMPI/10% FBS. Samples was treated with 10 µM Camptothecin in DMSO to induce apoptosis, or treated with DMSO alone to act as a control. Treatment and control time was 1, 2, 3, 4, 5, and 6 hours, and a time zero point. The cell suspensions were then incubated at 37° C./5% $CO_2$ for a designated time. This type of experiment is sometimes called an "apoptosis time course". Each split was washed once in complete RPMI media/10% Fetal Bovine Serum (FBS) and resuspended at $1\times10^6$ cells/mL in complete RPMI media with 10% FBS. Flow tubes were made up by adding one mL designated cell suspension to which 10 µM compound (24) was added to one mL cell suspension, incubated at 37° C. for 30 minutes protected from light, and the SYTOX® Blue dead cell stain (SYTOX is a registered trademark of Molecular Probes, Inc.; Eugene, Oreg.) was added as a dead cell discriminator. Cells were processed using the Becton Dickinson LSRII Flow Cytometer. A SYTOX® Blue stain vs compound (24) stain plot was made and a gate was made on compound (24) stain positive and SYTOX® Blue stain negative cells to gate out dead cells, and to ensure only live cells were analyzed. Fluorescence from the SYTOX® Blue stain was collected using 405 nm excitation laser with 450/50 bandpass and compound (24) stain fluorescence was collected at 585/42 bandpass using the 488 nm excitation laser as well as collected at the same 585/42 bandpass using the 532 nm excitation laser. Collection of 30,000 events occurred at a flow rate of about 200 events/second. The data was further analyzed using ModFit LT Flow Cytometry Modeling Software from Verity Software House, Inc. to look at ratio of G2/G1 and the CV of G1 phase and the percent sub-G0 population (apoptotic population).

Typical cell cycle histograms were demonstrated showing G0G1 phase, S phase, and G2M phase for each control time point with no sub-G0 population identified. Cell cycle histograms for the cells treated with Camptothecin demonstrated a population of cells at the sub-G0 location which begin to show at 3 hours induction and continue to increase throughout the time course at each time point afterwards. Further analysis using ModFit Software with an apoptotic model, showed typical cell cycle staining for control cells and growing sub-G0 population with the induced cells. This demonstrated that compound (24) stains live cells for identification of a sub-G0 population in apoptotic cells which increases with time of induction. Similar results were obtained with 532 nm excitation.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

What is claimed is:

1. A chemical compound having the structure:

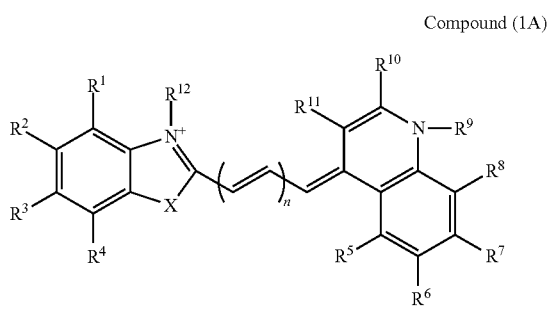

Compound (1A)

wherein:
n is 0;
X is oxygen;
$R^1, R^2, R^3, R^4, R^5, R^6, R^7, R^8, R^{10}$, and $R^{11}$ independently comprise hydrogen, a hydroxyl group, an alkoxy group, a thiol, a thioalkyl, a thioaryl, a halogen, an alkyl group, an alkenyl group, an alkynyl group, an aromatic group, a primary amine group, a secondary amine group, a tertiary amine group, a reactive group, or combinations thereof, wherein at least one of $R^1, R^2, R^3$, and $R^4$ comprises an aromatic group or an alkynyl group;
$R^9$ comprises an aromatic group or alkyl-aromatic group; and
$R^{12}$ is an alkyl group.

2. The chemical compound of claim 1, wherein:
$R^1, R^2, R^3, R^4, R^5, R^6, R^7, R^8, R^{10}$, and $R^{11}$ are independently hydrogen, a hydroxyl group, an alkoxy group, a thiol, a thioalkyl, a thioaryl, a halogen, an alkyl group, an alkenyl group, an alkynyl group, an aromatic group, a primary amine group, a secondary amine group, a tertiary amine group, a reactive group, or combinations thereof, wherein at least one of $R^1, R^2, R^3$, and $R^4$ comprises an aromatic group or an alkynyl group.

3. The chemical compound of claim 1, wherein $R^{10}$ is an amine group.

4. The chemical compound of claim 1, wherein:
at least one of $R^1, R^2, R^3$, and $R^4$ comprises an aromatic group or an alkynyl group;
$R^9$ comprises an aromatic group or alkyl-aromatic group; and
$R^{10}$ comprises an amine group.

5. The chemical compound of claim 1, wherein $R^{12}$ is a $C_1$-$C_8$ alkyl group.

6. The chemical compound of claim 1, wherein $R^{12}$ is a methyl group.

7. The chemical compound of claim 1, further comprising one or more cations or anions.

8. A kit comprising:
DNA, RNA, or both DNA and RNA; and
a chemical compound having the structure:

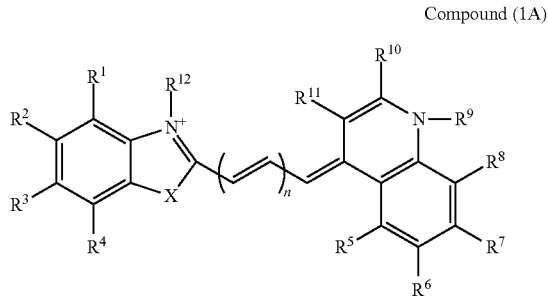

Compound (1A)

wherein:
n is 0;
X is oxygen;
$R^1, R^2, R^3, R^4, R^5, R^6, R^7, R^8, R^{10}$, and $R^{11}$ independently comprise hydrogen, a hydroxyl group, an alkoxy group, a thiol, a thioalkyl, a thioaryl, a halogen, an alkyl group, an alkenyl group, an alkynyl group, an aromatic group, a primary amine group, a secondary amine group, a tertiary amine group, a reactive group, or combinations thereof, wherein at least one of $R^1, R^2, R^3$, and $R^4$ comprises an aromatic group or an alkynyl group;
$R^9$ comprises an aromatic group or alkyl-aromatic group; and
$R^{12}$ is an alkyl group.

9. The compound of claim 1, wherein the compound is:

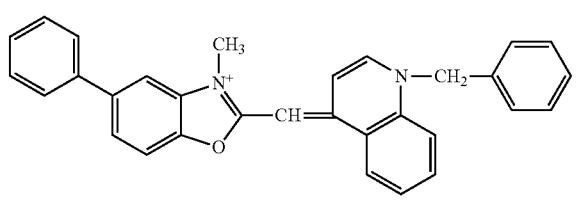 [SMILES: C[n+]1c(C=C2C=CN(Cc3ccccc3)c3ccccc32)oc2ccc(-c3ccccc3)cc21]

* * * * *